United States Patent
Taylor

(10) Patent No.: US 11,707,449 B2
(45) Date of Patent: Jul. 25, 2023

(54) METHODS AND FORMULATIONS FOR TREATMENT OF SPINOBULBAR MUSCULAR ATROPHY

(71) Applicant: ST. JUDE CHILDREN'S RESEARCH HOSPITAL, INC., Memphis, TN (US)

(72) Inventor: Joseph Paul Taylor, Memphis, TN (US)

(73) Assignee: ST. JUDE CHILDREN'S RESEARCH HOSPITAL, INC., Memphis, TN (US)

( * ) Notice: Subject to any disclaimer, the term of this patent is extended or adjusted under 35 U.S.C. 154(b) by 231 days.

(21) Appl. No.: 16/759,715

(22) PCT Filed: Oct. 26, 2018

(86) PCT No.: PCT/US2018/057656
§ 371 (c)(1),
(2) Date: Apr. 27, 2020

(87) PCT Pub. No.: WO2019/084365
PCT Pub. Date: May 2, 2019

(65) Prior Publication Data
US 2022/0226289 A1      Jul. 21, 2022

Related U.S. Application Data

(60) Provisional application No. 62/578,084, filed on Oct. 27, 2017.

(51) Int. Cl.
*A61K 31/4184* (2006.01)
*A61P 21/00* (2006.01)

(52) U.S. Cl.
CPC .......... *A61K 31/4184* (2013.01); *A61P 21/00* (2018.01)

(58) Field of Classification Search
CPC ............................................... A61K 31/4184
See application file for complete search history.

(56) References Cited

U.S. PATENT DOCUMENTS

| 8,202,905 B2 * | 6/2012 | Shih ........................ A61P 25/00 514/541 |
| 2011/0077221 A1 | 3/2011 | Dalton et al. |
| 2015/0284725 A1 * | 10/2015 | Hung ...................... A61P 21/00 514/44 A |

OTHER PUBLICATIONS

PubChem CID 3114779, National Center for Biotechnology Information. PubChem Compound Summary for CID 3114779. https://pubchem.ncbi.nlm.nih.gov/compound/3114779. Accessed May 27, 2022, create date Aug. 9, 2005. (Year: 2005).*
Baniahmad, Journal of Molecular Neuroscience, 2016, 58(3), pp. 343-347. (Year: 2016).*
International Search Report dated Jan. 7, 2019.
Lack et al. 'Targeting the Binding Function 3 (BF3) Site of the Human Androgen Receptor through Virtual Screening', Journal of Medicinal Chemistry, 2011, vol. 54, pp. 8563-8573. p. 8564, col. 1, para 2-3; p. 8566, Table 1; p. 8570, Figure 8.
Munuganti et al. 'Targeting the binding function 3 (BF3) site of the Androgen Receptor through Virtual Screening. 2. Development of 2-(2-(phenoxyethyl)thio-1H-(benizmidazole) derivatives', Journal of Medicinal Chemistry, 2013, vol. 56, pp. 1136-1148. Entire Document.

* cited by examiner

*Primary Examiner* — Laura L Stockton
(74) *Attorney, Agent, or Firm* — Innovators Legal

(57) ABSTRACT

Methods and formulations are provided for treating spinobulbar muscular atrophy in a subject in need thereof. By administering a therapeutically effective amount of a selective androgen receptor modulator or a small molecule such as 1-[2-(4-methylphenoxy)ethyl]-2-[(2-phenoxyethyl)sulfanyl]-1H-benzimidazole or a derivative, prodrug, or pharmaceutically acceptable salt thereof, one or more symptoms of spinobulbar muscular atrophy can be ameliorated. The effective amount can be effective to prevent or delay loss of body weight, a loss of mobility, and/or a loss of physical strength in the subject; to prevent or delay neurogenic atrophy and/or to prevent a loss of spinal cord motor neurons in the subject; to restore the frequency of type I myofibers to normal levels for a healthy subject; and/or to reverse testicular atrophy in the subject.

19 Claims, 70 Drawing Sheets

METHODS AND FORMULATIONS FOR TREATMENT OF SPINOBULBAR MUSCULAR ATROPHY

CROSS-REFERENCE TO RELATED APPLICATIONS

This application is the 35 U.S.C. § 371 national stage application of PCT Application No. PCT/US2018/057656, filed Oct. 26, 2018, which claims priority to, and the benefit of, U.S. provisional application entitled "METHODS AND FORMULATIONS FOR TREATMENT OF SPINOBULBAR MUSCULAR ATROPHY" having Ser. No. 62/578,084, filed Oct. 27, 2017, both of which are herein incorporated by reference in their entireties.

STATEMENT REGARDING FEDERALLY SPONSORED RESEARCH OR DEVELOPMENT

This invention was made with government support under award NS053825 awarded by the National Institutes of Health. The government has certain rights in the invention.

TECHNICAL FIELD

The present disclosure generally relates to formulations and methods of treatment for spinobulbar muscular atrophy.

BACKGROUND

Spinal bulbar muscular atrophy (SBMA), or Kennedy's disease, is a progressive neurodegenerative disease affecting approximately 1 in 40,000 men worldwide[1]; however, this number is likely underestimated due to common misdiagnoses (e.g., limb girdle muscular dystrophy and amyotrophic lateral sclerosis [ALS])[2]. Although SBMA is not typically fatal, the quality of life is profoundly affected as patients experience bulbar dysfunction, limb weakness loss of ambulation, and partial androgen insensitivity that often leads to feminization, testicular atrophy and fertility problems. Neuromuscular symptoms generally first appear as muscle spasms and weakness in the extremities, mouth, and throat, which progress to muscle wasting due to loss of motor neurons. There is currently no known cure for SBMA, and treatment is symptomatic, usually entailing physical therapy and rehabilitation. Patients with SBMA frequently become confined to a wheelchair later in life and require assistance with common daily tasks, such as eating[2].

There remains a need for methods and treatments of SBMA that overcome the aforementioned deficiencies.

SUMMARY

In various aspects described herein, pharmaceutical compositions and methods are provided for treating and/or alleviating one or more symptoms associated with spinal bulbar muscular atrophy in a subject in need thereof. In some aspects, the subject is a mammal, and in particular a human. In some aspects, the methods and the uses of the formulations are effective to prevent or delay loss of body weight, a loss of mobility, and/or a loss of physical strength in the subject. In some aspects, the methods and the uses of the formulations are effective to prevent or delay neurogenic atrophy and/or to prevent a loss of spinal cord motor neurons in the subject. In some aspects, the methods and the uses of the formulations are effective to restore the frequency of type I myofibers to normal levels for a healthy subject. In some aspects, the methods and the uses of the formulations are effective to reverse testicular atrophy in the subject.

In some aspects, pharmaceutical formulations and methods of use thereof are provided where the pharmaceutical formulation includes a therapeutically effective amount of a small molecule, a derivative thereof, a prodrug thereof, or a salt thereof; wherein the small molecule has a structure according to the following formula

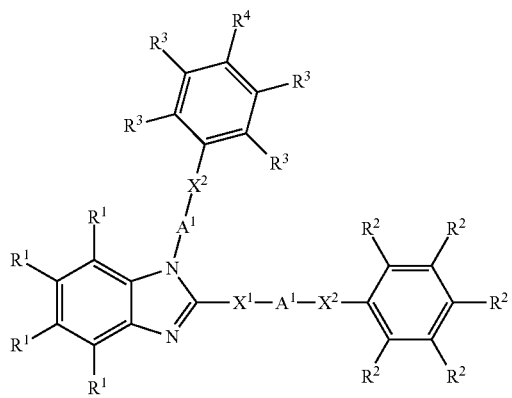

wherein each occurrence of $R^1$, $R^2$, $R^3$, and $R^4$ is independently a hydrogen, a hydroxyl, a halogen, or a substituted or unsubstituted $C_1$-$C_6$ alkyl or alkoxy; wherein each occurrence of $X^1$ and $X^2$ is independently O or S; wherein each occurrence of Al is independently none or a substituted or unsubstituted $C_1$-$C_6$ alkyl diradical; and wherein the therapeutically effective amount is effective to ameliorate one or more symptoms of spinobulbar muscular atrophy in the subject.

In some aspects, the small molecule is 1-[2-(4-methylphenoxy)ethyl]-2-[(2-phenoxyethyl)sulfanyl]-1H-benzimidazole having a structure according to the following formula

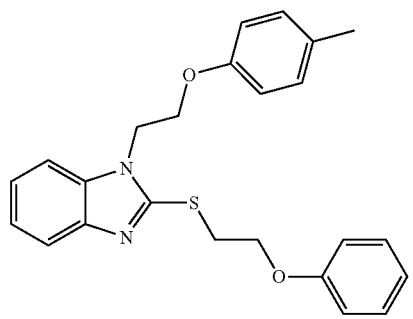

In some aspects, pharmaceutical formulations and methods of use thereof are provided where the pharmaceutical formulation includes a therapeutically effective amount of a selective androgen receptor modulator, wherein the therapeutically effective amount is effective to ameliorate one or more symptoms of spinobulbar muscular atrophy in the subject. In some aspects, the selective androgen receptor modulator alters a co-regulator binding to the activation function-2 (AF2) domain of the androgen receptor. In some aspects, the selective androgen receptor selectively binds to the binding function-3 (BF3) domain of the androgen receptor.

Other systems, methods, features, and advantages of pharmaceutical methods and compositions will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 1A is a structural depiction of the androgen receptor (AR) ligand-binding domain (LBD) in complex with tolfenamic acid (TA) or 1-[2-(4-methylphenoxy)ethyl]-2-[(2-phenoxyethyl)sulfanyl]-1H-benzimidazole (MEPB). The binding function-3 (BF3) domain and the core AF2 domain are indicated in the BF3 unbound structure. The TA and MEPB binding are depicted by the shaded regions in the central and far right structures respectively. The modeled FXXLF or LXXLL motifs are labelled. FIG. 1B is a bar graph of the viability of flies expressing human AR52Q in pan-neuronal tissues in the presence of vehicle (far left, white bar), and 1 mM DHT with varying amounts of TA (black bars) ranging, left to right, from 0 μM to 400 μM TA; n=50 adult flies/treatment group. FIG. 1C is a bar graph of the viability of flies expressing human AR52Q in pan-neuronal tissues in the presence of vehicle (far left, white bar), and 1 mM DHT with varying amounts of MEPB (black bars) ranging, left to right, from 0 μM to 400 μM MEPB; n=50 adult flies/treatment group. FIG. 1D depicts representative traces of the walking pattern of adult flies expressing AR52Q, AR52Q-K720A, or AR66Q-E897K in motor neurons for 90 sec in a well of a 12-well tissue culture plate. Adult flies were reared on food containing 1% ethanol+0.1% DMSO, 1 mM DHT+0.1% DMSO, 1 mM DHT+100 μM TA, or 1 mM DHT+100 μM MEPB. FIG. 1E is a bar graph quantifying the mean distance walked by adult SBMA flies, determined from 15 individual tracing patterns per genotype or treatment group. FIG. 1F is a bar graph quantifying the mean velocity of adult SBMA flies, determined from 15 individual tracing patterns per genotype or treatment group. FIG. 1G is an image of staining and quantification of neuromuscular junctions of larval SBMA flies. Arrowheads indicate satellite boutons. FIG. 1H is a bar graph of the mean satellite boutons quantified for 2-3 muscle segments from 12 dissected larval pelts per treatment group. FIG. 1I is a bar graph of the mean neuromuscular junction branches quantified for 2-3 muscle segments from 12 dissected larval pelts per treatment group. Data shown in FIGS. 1B-1C were evaluated by Chi-square analysis; comparisons between the actual population frequencies of each treatment group and the predicted population frequency were based on the DHT+DMSO group. Data shown in FIGS. 1E-1F and FIGS. 1H-1I were evaluated by one-way ANOVA, and Dunnett posthoc analysis was used for pairwise comparisons between each treatment group and the DHT+DMSO group. *P≤0.05, **P≤0.01. All error bars represent s.e.m.

FIG. 2A-2D are graphs of phenotypic measures of SBMA degeneration in NTG (diamonds) and AR121Q mice (squares), in addition to sham-operated (triangles) and castrated (circles) AR121Q mice. FIG. 2A is a graph of the mean body weight. FIG. 2B is a graph of the mean rotarod activity. FIG. 2C is a graph of the mean grip strength. FIG. 2D is a graph of the survival. All data points in FIGS. 2A-2D are for n=5 mice per group, *P<0.001 by two-way ANOVA and Dunnett multiple comparison test (FIGS. 2A-2C) or Kaplan-Meier estimation (log-rank test) (FIG. 2D). FIGS. 2E-2F are images of representative spinal cord (FIG. 2E) and skeletal muscle (FIG. 2F) sections from 7-week-old NTG and AR121Q mice. Sections were stained with hematoxylin and eosin (H&E) stain for assessment of morphology, in addition to AR (N20) and ubiquitin antibodies. White arrowheads indicate ubiquitin-positive nuclear inclusions in the spinal cord. Dotted lines trace around representative myofibers, demonstrating differences in myofiber size. Arrow indicates atrophied myofibers. Arrowheads indicate myofibers containing centralized nuclei. FIG. 2G is images of PolyQ (5TF1-1C2) and ubiquitin costaining in spinal cord of NTG and AR121Q mice. FIGS. 2H-2K are bar graphs quantifying the mean muscle fiber diameter of gastrocnemius/soleus myofibers (FIG. 2H), mean type I and type II hindlimb muscle fiber staining (FIG. 2I), and ChAT-positive motor neurons in the anterior horn of the thoracic spinal cord (FIGS. 2J-2K) of NTG and AR121Q mice. n=3 mice per genotype, P<0.01, *P<0.05 by Student t-test. FIG. 2L is images of the immunofluorescence with antibodies against NCAM and PSA-NCAM in skeletal muscle tissues of NTG and AR121Q mice. Scale bars represent 50 μm. All error bars represent s.e.m.

FIG. 3A is a graph of the mean body weight of AR121Q mice from 4 weeks until 8 weeks of age. FIG. 3B is a graph of the mean rotarod performance of AR121Q mice from 5 weeks until 7 weeks of age. FIG. 3C is a graph of the mean grip strength (measured as grams force) of all four paws of AR121Q mice. Data shown in FIGS. 3A-3C were evaluated by one-way ANOVA with repeated measures followed by Tukey posthoc analysis for all pairwise comparisons. *P≤0.05 vs NTG. FIG. 3D is a graph of the Kaplan-Meier survival estimation of AR121Q mice (log-rank test). FIGS. 3E-3F are bar graphs quantifying footprint/gait analysis of AR121Q mice. Average stride length (FIG. 3E) and forepaw and hindpaw overlap (FIG. 3F) are depicted. n=1-3 NTG mice per drug group, n=3-5 AR121Q mice per drug group. Two-way ANOVA followed by Tukey multiple comparison test. *P≤0.05, **P≤0.01 vs NTG. All error bars represent s.e.m. FIG. 3G is a set of video stills of clasping behavior in representative NTG and AR121Q mice. FIG. 3H is images of representative spinal cord sections from AR121Q mice treated with vehicle, TA, or MEPB. Sections were stained with AR (N20), ubiquitin, or polyQ (5TF1-1C2) antibodies. Arrowheads indicate the presence of ubiquitin-positive nuclear inclusions. FIG. 3I is images of representative skeletal muscle sections (gastrocnemius/soleus) from AR121Q mice treated with vehicle, TA, or MEPB. Sections were stained with H&E or Gomori trichrome stain for muscle morphology, in addition to ubiquitin antibody. Dotted lines trace around representative myofibers, demonstrating differences in myofiber size. Arrows indicate atrophied myofibers. Arrowheads indicate myofibers containing centralized nuclei. Vehicle is 1% DMSO in corn oil administered three times per week; TA is 50 mg/kg administered three times per week; and MEPB is 50 mg/kg administered three times per week. Scale bars represent 50 μm.

FIGS. 4A-4F are graphs for each phenotypic assay (mean body weight in FIGS. 4A-4B, mean rotarod activity in FIGS. 4C-4D, mean grip strength in FIGS. 3E-4F) are depicted using identical scales to allow comparison between NTG mice (FIGS. 4A, 4C, and 4E) and AR121Q mice (FIGS. 4B, 4D, and 4F). Mice were treated with vehicle (squares; 1% DMSO in corn oil), low-dose MEPB (circles; 50 mg/kg, three times per week), or high-dose MEPB (triangles; 100 mg/kg, three times per week). Arrows indicate last graphed data point for each treatment group due to attrition of animal numbers (<3 mice/group) from loss of >10% body weight or limb paralysis/paresis. *P≤0.05, **P≤0.01. All error bars represent s.e.m. FIGS. 4G-4I are bar graphs depicting side-by-side comparisons of phenotypic assays (mean body weight (FIG. 4G), mean rotarod activity (FIG. 4H), and mean grip strength (FIG. 4I) in vehicle-, low-dose MEPB-, and high-dose MEPB-treated AR121Q mice for time points in which ≥3 mice per treatment group were assayed. Data shown in FIGS. 4G-4I were evaluated up to 8 or 9 weeks of age by one-way ANOVA with repeated measures followed by Tukey posthoc analysis for all pairwise comparisons. *P≤0.05, **P≤0.01. FIG. 4J is a graph of a Kaplan-Meier survival estimation in treated (vehicle, low-dose, and high-dose) NTG and AR121Q mice (log-rank test). FIG. 4K is a graph of QOL score of AR121Q mice from each treatment group from 6 to 8 weeks of age. In all panels, mice were treated with vehicle (1% DMSO in corn oil), low-dose MEPB (50 mg/kg, three times per week), or high-dose MEPB (100 mg/kg, three times per week). A mixed-effect model was applied with SAS software to determine statistical significance. All error bars represent s.e.m.

FIG. 5A is images of representative spinal cord sections from AR121Q mice treated with vehicle (1% DMSO in corn oil) or high-dose MEPB (100 mg/kg, three times per week). Sections were stained with H&E and toluidine blue to assess spinal cord morphology. Sections were also stained with AR (N20), polyQ (5TF1-1C2), and ubiquitin antibodies. White arrowheads indicate ubiquitin-positive nuclear inclusions. Scale bars represent 200 μm. FIG. 5B is a bar graph quantifying the mean relative number of cells in the spinal cord ventral horn containing positive polyQ (white) or ubiquitin (black) staining in AR121Q mice. Quantification was performed from 2-4 fields/mouse, 3 mice/treatment group. FIG. 5C is images of representative skeletal muscle (gastrocnemius/soleus) sections from AR121Q mice treated with either vehicle or high-dose MEPB. Sections were stained with H&E and Gomori trichrome to evaluate morphology, in addition to AR, polyQ, and ubiquitin antibodies. Dotted lines trace around representative myofibers, demonstrating differences in myofiber size. Arrows indicate atrophied myofibers. Arrowhead indicates myofibers containing centralized nuclei. Scale bars represent 200 μm. FIG. 5D is a bar graph quantifying the mean muscle fiber diameter of gastrocnemius/soleus myofibers of NTG (white) and AR121Q mice (black). Quantification was performed from 2-4 fields/mouse, 3 mice/treatment group. Data shown in FIG. 5B and FIG. 5D were evaluated by two-way ANOVA followed by Dunnett posthoc analysis for pairwise comparisons between each MEPB treatment group and vehicle. *P≤0.05. FIG. 5E is representative images of skeletal muscle stained with antibodies against NCAM and PSA-NCAM in AR121Q mice treated with vehicle (1% DMSO in corn oil), low-dose MEPB (50 mg/kg, three times per week), or high-dose MEPB (100 mg/kg, three times per week). Scale bars represent 50 μm. FIG. 5F is a bar graph of PSA-NCAM/NCAM colocalized regions. Data were evaluated by two-way ANOVA followed by Tukey multiple comparison test. ***P≤0.001. FIG. 5G is a bar graph of the area of testis were measured in 3 to 4 sections per mouse, in 2 to 3 mice per group. Data were evaluated by one-way ANOVA and Dunnett posthoc analysis for comparison between each AR121Q treatment group and NTG vehicle. *P≤0.05. All error bars represent s.e.m.

FIG. 6A is representative immunofluorescence of HEK293T cells transiently transfected with AR65Q for 48 h in culture media devoid of steroid hormones. Cells were treated for 24 h with vehicle, 10 nM DHT, or 10 nM DHT+10 μM bicalutamide (Bic), TA, or MEPB prior to staining (n=3) with AR (D6F11) and DAPI. Scale bars represent 10 μm. FIG. 6B is an image of third instar larvae expressing GFP-AR52Q in motor neurons were dissected and stained for nuclear membrane and DAPI FIG. 6C is a bar graph of the AR transcriptional activity reporter assay. HEK293T cells were transiently transfected with AR24Q or AR65Q in addition to an ARE-luciferase reporter prior to treatment with Bic, TA, or MEPB. Four independent biological replicates were performed on different days with three sample replicates for each treatment group. FIG. 6D is a bar graph of the digital PCR assay to access the impact of MEPB on AR target gene expression. FIG. 6E is a bar graph of the mammalian two-hybrid assay to assess binding between the AR LBD and the corepressors NCoR or SMRT in the presence of TA or MEPB. Two independent biological replicates were performed on different days with three sample replicates for each treatment group. Data shown in FIG. 6C were evaluated by two-way ANOVA followed by Dunnett posthoc analysis for pairwise comparisons between each treatment group and the DHT+DMSO group. Data shown in FIG. 6D were evaluated by ordinary one-way ANOVA followed by Tukey posthoc analysis for all pairwise comparisons. Data shown in FIG. 6E were evaluated by two-way ANOVA followed by Tukey posthoc analysis for all pairwise comparisons. *P≤0.05, P≤0.01, *P≤0.001. All error bars represent s.e.m.

FIG. 7A is a bar graph of mean viability of SBMA flies (AR52Q) reared on food containing vehicle (EtOH), DHT, or DHT in addition to the AF2 modulators described by Estebanez-Perpina et al. (2007)[19]. FIG. 7B is a bar graph of mean viability of SBMA flies reared on food containing vehicle, DHT, or DHT in addition to the AF2 modulators described by Lack et al. (2011)[21]. FIG. 7C is a bar graph of mean viability of transgenic flies expressing AR52Q (ELAV>UAS-AR52Q) reared on food containing vehicle or DHT and transgenic flies expressing AR52Q-K720A or AR66Q-E897K reared on food containing DHT. FIG. 7D is a bar graph of mean viability of SBMA flies (ELAV>UAS-AR52Q) reared on food containing MEPB in the absence of DHT. FIG. 7E is a bar graph of mean viability of SBMA flies (ELAV>UAS-AR52Q) reared on food containing DHT and bicalutamide. FIG. 7F is a bar graph of mean viability of SBMA flies (ELAV>UAS-AR52Q) reared on food containing DHT and ibuprofen. All data were evaluated by Chi-square analysis; n=50 adult flies/treatment group for all experiments. Comparisons of data shown in FIG. 7A, FIG. 7B, FIG. 7C, and FIG. 7E were made between the actual population frequencies of each treatment group and the predicted population frequency determined by the sum of all treatment groups of AR52Q flies. In FIG. 7D, the predicted population frequency of each treatment group was determined by the ethanol+DMSO group. In FIG. 7F, the predicted population frequency of each treatment group was determined by the DHT+1 µM ibuprofen group. *P≤0.05. All error bars represent s.e.m.

FIG. 8A is representative images of SBMA fly eyes reared on food containing vehicle (EtOH), DHT, or DHT+bicalutamide (Bic), dimethylcurcumin (DMC), TA, or MEPB. Images were captured from four flies for each treatment group. FIG. 8B is images of representative immunoblot of AR expression in SBMA fly heads. FIG. 8C is a bar graph quantifying protein levels from three immunoblots, as depicted in FIG. 8B. Data shown in FIG. 8C were evaluated by one-way ANOVA followed by Dunnett posthoc analysis for pairwise comparisons between each treatment group and the DHT-only group. *P≤0.05. All error bars represent s.e.m. FIG. 8D depicts flies expressing AR52Q in eyes were fed with drugs in their adult stage for 4 days. FIG. 8E depicts flies expressing AR52Q were raised on food containing drugs during their development from their embryonic stage. Enclosed adults were immediately collected and processed. Three heads for each treatment were used to detect aggregation.

FIG. 9A is a schematic depicting the cDNA construct used to generate transgenic SBMA mice. FIG. 9B is an image of fluorescence in situ hybridization of an AR121Q-specific probe and a general marker of chromosome 17 in chromosome spreads isolated from lungs of AR121Q mice. FIG. 9C is an image of western blot analysis of spinal cord and muscle expression of transgenic human AR in AR121Q mice and a previously published SBMA mouse model (AR97Q). FIG. 9D is a bar graph quantifying the levels of transgenic human AR compared with that of endogenous mouse AR in AR121Q and AR97Q mice. n=3 mice per group, *P<0.05 by Student t-test. FIGS. 9E-9G depict representative brain (FIG. 9E), testis (FIG. 9F) and liver (FIG. 9G) sections from 7-week-old NTG and AR121Q mice. Sections were stained with H&E for assessment of morphology, in addition to AR (N20) and ubiquitin antibodies. Scale bars represent 100 µm. FIG. 9H is images of PolyQ and ubiquitin costaining in skeletal muscle of NTG and AR121Q mice. FIG. 9I is bar graphs quantifying fibers with centralized nuclei in lower and upper hindlimb muscles. n=2 to 3 mice per group, one-way ANOVA. FIG. 9J is representative images of testis from NTG, AR121Q and AR121Q treated with 100 mg/kg of MEPB mice. Scale bars represent 500 µm. All error bars represent s.e.m.

FIG. 10A is graphs of MEPB concentrations in plasma, liver, muscle, testes, brain, and spinal cord were measured at multiple time points (5 min to 48 h) following a single intraperitoneal injection of 100 mg/kg body weight MEPB. MEPB half-life ($T_{1/2}$) was calculated for each tissue. Each square indicates one collected sample. FIG. 10B is a graph of TA concentrations in plasma, liver, muscle, testes, brain, and spinal cord measured at multiple time points (1-48 h) following a single intraperitoneal injection of 50 mg/kg body weight TA.

FIG. 11A is images of representative footprint/ gait analysis of 8-week-old AR121Q mice treated with MEPB. Hindpaws were painted blue and forepaws were painted red. FIG. 11B is video stills of clasping behavior in representative NTG and AR121Q mice. FIG. 11C and FIG. 11D are bar graphs quantifying the number (FIG. 11C) and size (FIG. 11D) of ChAT-positive motor neurons in the anterior horn of the thoracic spinal cord of NTG and AR121Q mice treated with vehicle, 50 mg/kg MEPB, or 100 mg/kg MEPB; n=2 to 3 mice per treatment group. *P≤0.05 by one way ANOVA and Dunnett posthoc analysis for pairwise comparing between each AR121Q treatment group and the NTG vehicle group. FIG. 11E and FIG. 11F are bar graphs quantifying mean type I and type II hindlimb muscle fiber staining in NTG and AR121Q mice, n=3 mice per treatment group. *P≤0.05 by two-way ANOVA and Dunnett posthoc analysis for pairwise comparisons between each treatment group and their corresponding NTG control group. FIG. 11G is a bar graph quantifying mean blood concentrations of metabolites, electrolytes, enzymes, and other molecules associated with kidney and liver function from NTG and AR121Q mice. Mean concentrations were normalized to vehicle-treated NTG mice in order to allow depiction of all chemistries on one graph, n=2 mice per treatment group. Data were analyzed by two-way ANOVA FIG. 11H and FIG. 11I are bar graphs quantifying mean blood concentrations of serum creatine kinase (FIG. 11H) and serum testosterone (FIG. 11I) in NTG and AR121Q mice treated with vehicle, 50 mg/kg MEPB, or 100 mg/kg MEPB; n=3 mice per treatment group. Data were evaluated by two-way ANOVA. All error bars represent s.e.m.

FIG. 12A is images of representative immunoblot of MN1 cells that were untransfected, stably transfected with AR24Q, or stably transfected with AR65Q. Cells were treated with vehicle (0.1% ethanol+0.1% DMSO), 10 nM DHT+0.1% DMSO, 10 nM DHT+10 µM TA, or 10 nM DHT+10 µM MEPB for 24 h. Blots were stained with AR (D6F11) and tubulin antibodies. FIG. 12B is a bar graph quantifying AR protein levels from three immunoblots, as depicted in FIG. 12A. FIG. 12C is images of representative immunoblot of stably transfected MN1-AR65Q cells treated with 10 nM DHT+TA or MEPB. FIG. 12D is a bar graph quantifying AR protein levels from three immunoblots, as depicted in FIG. 12C. FIG. 12E is images of representative immunoblot of HEK293T cells transiently transfected with AR65Q for 24 h. Cells were treated with vehicle, 10 nM DHT, or 10 nM DHT+bicalutamide (Bic), TA, or MEPB for 24 h, and blots (n=3) were stained with AR (D6F11) and tubulin antibodies. FIG. 12F is images of filter trap assay for AR aggregates from lysates prepared from HEK293T cells transiently transfected with FLAG-AR65Q. Cellulose acetate membranes (n=3) were stained with FLAG (M2) antibody. All error bars represent s.e.m.

FIG. 13A and FIG. 13C are images of representative immunoblot of skeletal muscle (FIG. 13A) and spinal cord (FIG. 13C) of AR121Q mice treated with vehicle, 50 mg/kg MEPB, or 100 mg/kg MEPB. FIG. 13B and FIG. 13C are bar graphs quantifying mouse AR and human AR protein levels relative to REVERT total protein stain, n=3 mice per treatment group. Data were analyzed by one-way ANOVA. All error bars represent s.e.m.

DETAILED DESCRIPTION

Figure 1A:
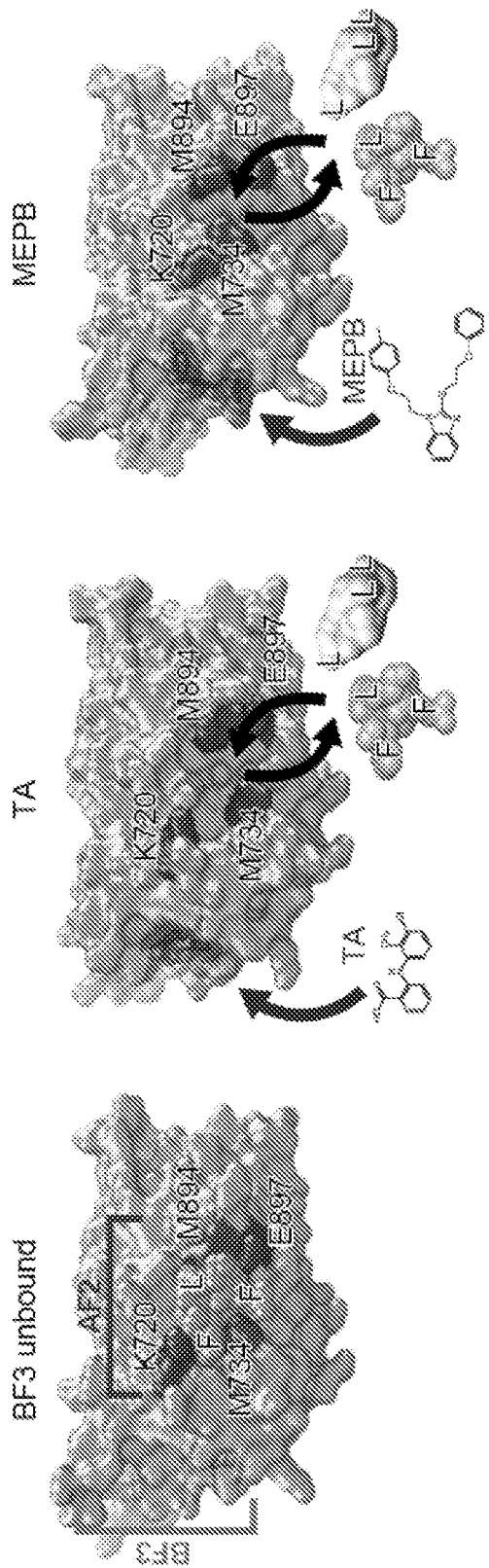
FIGS. 1A-1I demonstrate activation function-2 (AF2) modulation rescues degeneration in a fruit fly model of Spinal bulbar muscular atrophy (SBMA).

In various aspects, pharmaceutical formulations and methods are provided for treating spinobulbar muscular atrophy in a subject in need thereof. An effective amount of 1-[2-(4-methylphenoxy)ethyl]-2-[(2-phenoxyethyl)sulfanyl]-1H-benzimidazole ("MEPB") has been found to ameliorate one or more symptoms of spinobulbar muscular atrophy in the subject. For example, in some aspects an effective amount of MEPB has been found to prevent or delay loss of body weight, a loss of mobility, and/or a loss of physical strength in the subject. In some aspects an effective amount of MEPB has been found to prevent or delay neurogenic atrophy and/or a loss of spinal cord motor neurons in the subject. In some aspects an effective amount of MEPB has been found to restore frequency of type I myofibers to normal levels for a healthy subject and/or to reverse testicular atrophy in the subject.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of anatomy, biochemistry, histology, microbiology, molecular biology, neuroscience, pharmacology, photobiology, physiology, toxicology, and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The terms "subject" or "patient", as used herein, refer to any organism to which the compounds may be administered, e.g., for experimental, therapeutic, diagnostic, and/or prophylactic purposes. Typical subjects include animals (e.g., mammals such as mice, rats, rabbits, non-human primates, and humans) and/or plants. In certain aspects, the subject is a human.

The terms "treating" or "preventing", as used herein, can include preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human.

The term "modulation" is art-recognized and refers to up regulation (i.e., activation or stimulation), down regulation (i.e., inhibition or suppression) of a response, or the two in combination or apart.

"Parenteral administration", as used herein, means administration by any method other than through the digestive tract or non-invasive topical or regional routes. For example, parenteral administration may include administration to a patient intravenously, intradermally, intraperitoneally, intrapleurally, intratracheally, intramuscularly, subcutaneously, subjunctivally, by injection, and by infusion.

"Enteral administration", as used herein, means administration via absorption through the gastrointestinal tract. Enteral administration can include oral and sublingual administration, gastric administration, or rectal administration.

The terms "sufficient" and "effective", as used interchangeably herein, refer to an amount (e.g., mass, volume, dosage, concentration, and/or time period) needed to achieve one or more desired result(s). A "therapeutically effective amount" is at least the minimum concentration required to effect a measurable improvement or prevention of any symptom or a particular condition or disorder, to effect a measurable enhancement of life expectancy, or to generally improve patient quality of life. The therapeutically effective amount is thus dependent upon the specific biologically active molecule and the specific condition or disorder to be treated. Therapeutically effective amounts of many active agents, such as antibodies, are well known in the art. The therapeutically effective amounts of anionic proteins, protein analogues, or nucleic acids hereinafter discovered or for treating specific disorders with known proteins, protein analogues, or nucleic acids to treat additional disorders may be determined by standard techniques which are well within the craft of a skilled artisan, such as a physician.

For administration of a therapeutic composition as disclosed herein (e.g., a selective androgen receptor modulator, small molecule therapeutic agent, or a salt or prodrug thereof), conventional methods of extrapolating human dosage based on doses administered to a murine animal model can be carried out using the conversion factor for converting the mouse dosage to human dosage: Dose Human per kg=Dose Mouse per kg×12 (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/m$^2$ dose, multiply the dose by the appropriate km factor. In an adult human, 100 mg/kg is equivalent to 100 mg/kg×37 kg/m$^2$=3700 mg/m$^2$.

The terms "bioactive agent" and "active agent", as used interchangeably herein, include, without limitation, physiologically or pharmacologically active substances that act locally or systemically in the body. A bioactive agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment.

The term "prodrug" refers to an agent, including a nucleic acid or proteins that is converted into a biologically active form in vitro and/or in vivo. Prodrugs can be useful because, in some situations, they may be easier to administer than the parent compound. For example, a prodrug may be bioavailable by oral administration whereas the parent compound is not. The prodrug may also have improved solubility in pharmaceutical compositions compared to the parent drug. A prodrug may be converted into the parent drug by various mechanisms, including enzymatic processes and metabolic hydrolysis. Harper, N.J. (1962) Drug Latentiation in Jucker, ed. *Progress in Drug Research,* 4:221-294; Morozowich et al. (1977) Application of Physical Organic Principles to Prodrug Design in E. B. Roche ed. *Design of Biopharmaceutical Properties through Prodrugs and Analogs,* APhA; Acad. Pharm. Sci.; E. B. Roche, ed. (1977) *Bioreversible Carriers in Drug in Drug Design, Theory and Application,* APhA; H. Bundgaard, ed. (1985) Design of Prodrugs, Elsevier; Wang et al. (1999) Prodrug approaches to the improved delivery of peptide drug, *Curr. Pharm. Design.* 5(4):265-287; Pauletti et al. (1997) Improvement in peptide bioavailability: Peptidomimetics and Prodrug Strategies, *Adv. Drug. Delivery Rev.* 27:235-256; Mizen et al. (1998). The Use of Esters as Prodrugs for Oral Delivery of β-Lactam antibiotics, *Pharm. Biotech.* 11:345-365; Gaignault et al. (1996) Designing Prodrugs and Bioprecursors I. Carrier Prodrugs, *Pract. Med. Chem.* 671-696; M. Asgharnejad (2000). Improving Oral Drug Transport Via Prodrugs, in G. L. Amidon, P. I. Lee and E. M. Topp, Eds., *Transport Processes in Pharmaceutical Systems,* Marcell Dekker, p. 185-218; Balant et al. (1990) Prodrugs for the improvement of drug absorption via different routes of administration, *Eur. J. Drug Metab. Pharmacokinet.,* 15(2): 143-53; Balimane and Sinko (1999). Involvement of multiple transporters in the oral absorption of nucleoside analogues, *Adv. Drug Delivery Rev.,* 39(1-3):183-209; Browne (1997). Fosphenytoin (Cerebyx), *Clin. Neuropharmacol.* 20(1): 1-12; Bundgaard (1979). Bioreversible derivatization of drugs—principle and applicability to improve the therapeutic effects of drugs, *Arch. Pharm. Chemi.* 86(1): 1-39; H. Bundgaard, ed. (1985) *Design of Prodrugs,* New York: Elsevier; Fleisher et al. (1996) Improved oral drug delivery: solubility limitations overcome by the use of prodrugs, *Adv. Drug Delivery Rev.* 19(2): 115-130; Fleisher et al. (1985) Design of prodrugs for improved gastrointestinal absorption by intestinal enzyme targeting, *Methods Enzymol.* 112: 360-81; Farquhar D, et al. (1983) Biologically Reversible Phosphate-Protective Groups, *J. Pharm. Sci.,* 72(3): 324-325; Han, H. K. et al. (2000) Targeted prodrug design to optimize drug delivery, *AAPS PharmSci.,* 2(1): E6; Sadzuka Y. (2000) Effective prodrug liposome and conversion to active metabolite, *Curr. Drug Metab.,* 1(1):31-48; D. M. Lambert (2000) Rationale and applications of lipids as prodrug carriers, *Eur. J. Pharm. Sci.,* 11 Suppl. 2:S15-27; Wang, W. et al. (1999) Prodrug approaches to the improved delivery of peptide drugs. *Curr. Pharm. Des.,* 5(4):265-87.

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "pharmaceutically acceptable", as used herein, refers to compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the U.S. Food and Drug Administration. A "pharmaceutically acceptable carrier", as used herein, refers to all components of a pharmaceutical formulation that facilitate the delivery of the composition in vivo. Pharmaceutically acceptable carriers include, but are not limited to, diluents, preservatives, binders, lubricants, disintegrators, swelling agents, fillers, stabilizers, and combinations thereof.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "small molecule", as used herein, generally refers to an organic molecule that is less than 2000 g/mol in molecular weight, less than 1500 g/mol, less than 1000 g/mol, less than 800 g/mol, or less than 500 g/mol. Small molecules are non-polymeric and/or non-oligomeric.

The term "hydrophilic", as used herein, refers to substances that have strongly polar groups that readily interact with water.

The term "hydrophobic", as used herein, refers to substances that lack an affinity for water; tending to repel and not absorb water as well as not dissolve in or mix with water.

The term "lipophilic", as used herein, refers to compounds having an affinity for lipids.

The term "amphiphilic", as used herein, refers to a molecule combining hydrophilic and lipophilic (hydrophobic) properties. "Amphiphilic material" as used herein refers to a material containing a hydrophobic or more hydrophobic oligomer or polymer (e.g., biodegradable oligomer or polymer) and a hydrophilic or more hydrophilic oligomer or polymer.

The term "activated ester", as used herein, refers to alkyl esters of carboxylic acids where the alkyl is a good leaving group rendering the carbonyl susceptible to nucleophilic attack by molecules bearing amino groups. Activated esters are therefore susceptible to aminolysis and react with amines to form amides. Activated esters contain a carboxylic acid ester group —$CO_2R$ where R is the leaving group.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl has 30 or fewer carbon atoms in its backbone (e.g., $C_1$-$C_{30}$ for straight chains, $C_3$-$C_{30}$ for branched chains), 20 or fewer, 12 or fewer, or 7 or fewer. Likewise, in some embodiments cycloalkyls have from 3-10 carbon atoms in their ring structure, e.g. have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, or from one to six carbon atoms in its backbone structure. Likewise, "lower alkenyl" and "lower alkynyl" have similar chain lengths. Throughout the application, alkyl groups can be lower alkyls. In some embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In some embodiments, the "alkylthio" moiety is represented by one of —S-alkyl, —S-alkenyl, and —S-alkynyl. Representative alkylthio groups include methylthio, and ethylthio. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, and tert-butoxy. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula:

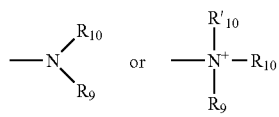

wherein $R_9$, $R_{10}$, and $R'_{10}$ each independently represent a hydrogen, an alkyl, an alkenyl, —(CH$_2$)$_m$—R$_8$ or R$_9$ and R$_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In some embodiments, only one of $R_9$ or $R_{10}$ can be a carbonyl, e.g., $R_9$, $R_{10}$ and the nitrogen together do not form an imide. In still other embodiments, the term "amine" does not encompass amides, e.g., wherein one of $R_9$ and $R_{10}$ represents a carbonyl. In additional embodiments, $R_9$ and $R_{10}$ (and optionally $R'_{10}$) each independently represent a hydrogen, an alkyl or cycloakyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

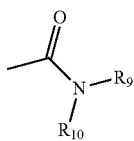

wherein $R_9$ and $R_{10}$ are as defined above.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

The term "aralkyl", as used herein, refers to an alkyl group substituted with an aryl group (e.g., an aromatic or heteroaromatic group).

The term "carbocycle", as used herein, refers to an aromatic or non-aromatic ring in which each atom of the ring is carbon.

"Heterocycle" or "heterocyclic", as used herein, refers to a cyclic radical attached via a ring carbon or nitrogen of a monocyclic or bicyclic ring containing 3-10 ring atoms, or from 5-6 ring atoms, consisting of carbon and one to four heteroatoms each selected from the group consisting of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, and —CN.

The term "carbonyl" is art-recognized and includes such moieties as can be represented by the general formula:

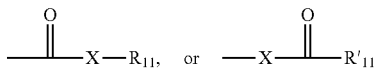

wherein X is a bond or represents an oxygen or a sulfur, and $R_{11}$ represents a hydrogen, an alkyl, a cycloalkyl, an alkenyl, an cycloalkenyl, or an alkynyl, $R'_{11}$ represents a hydrogen, an alkyl, a cycloalkyl, an alkenyl, an cycloalkenyl, or an alkynyl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "heteroatom" as used herein means an atom of any element other than carbon or hydrogen. Examples of heteroatoms are boron, nitrogen, oxygen, phosphorus, sulfur and selenium. Other heteroatoms include silicon and arsenic.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. The heteroatoms such as nitrogen may have hydrogen substituents and/or any permissible substituents of organic compounds described herein which satisfy the valencies of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, —CN, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

The term "copolymer" as used herein, generally refers to a single polymeric material that is comprised of two or more different monomers. The copolymer can be of any form, such as random, block, graft, etc. The copolymers can have any end-group, including capped or acid end groups.

The terms "polypeptide," "peptide" and "protein" generally refer to a polymer of amino acid residues. As used herein, the term also applies to amino acid polymers in which one or more amino acids are chemical analogues or modified derivatives of corresponding naturally-occurring amino acids. The term "protein", as generally used herein, refers to a polymer of amino acids linked to each other by peptide bonds to form a polypeptide for which the chain length is sufficient to produce tertiary and/or quaternary structure. The term "protein" excludes small peptides by definition, the small peptides lacking the requisite higher-order structure necessary to be considered a protein.

The terms "nucleic acid," "polynucleotide," and "oligonucleotide" are used interchangeably to refer to a deoxyribonucleotide or ribonucleotide polymer, in linear or circular conformation, and in either single- or double-stranded form. These terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general and unless otherwise specified, an analogue of a particular nucleotide has the same base-pairing specificity; i.e., an analogue of A will base-pair with T. The term "nucleic acid" is a term of art that refers to a string of at least two base-sugar-phosphate monomeric units. Nucleotides are the monomeric units of nucleic acid polymers. The term includes deoxyribonucleic acid (DNA) and ribonucleic acid (RNA) in the form of a messenger RNA, antisense, plasmid DNA, parts of a plasmid DNA or genetic material derived from a virus. Antisense is a polynucleotide that interferes with the function of DNA and/or RNA. The term nucleic acids refers to a string of at least two base-sugar-phosphate combinations. Natural nucleic acids have a phosphate backbone, artificial nucleic acids may contain other types of backbones, but contain the same bases. The term also includes PNAs (peptide nucleic acids), phosphorothioates, and other variants of the phosphate backbone of native nucleic acids.

A "functional fragment" of a protein, polypeptide or nucleic acid is a protein, polypeptide or nucleic acid whose sequence is not identical to the full-length protein, polypeptide or nucleic acid, yet retains at least one function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA binding function of a polypeptide can be determined, for example, by filter-binding, electrophoretic mobility shift, or immunoprecipitation assays. DNA cleavage can be assayed by gel electrophoresis. The ability of a protein to interact with another protein can be determined, for example, by co-immunoprecipitation, two-hybrid assays or complementation, e.g., genetic or biochemical. See, for example, Fields et al. (1989) *Nature* 340:245-246; U.S. Pat. No. 5,585,245 and PCT WO 98/44350.

As used herein, the term "linker" refers to a carbon chain that can contain heteroatoms (e.g., nitrogen, oxygen, sulfur, etc.) and which may be 1, 2, 3, 4, 5, 6, 7, 8, 9, 10, 11, 12, 13, 14, 15,16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 atoms long. Linkers may be substituted with various substituents including, but not limited to, hydrogen atoms, alkyl, alkenyl, alkynl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. Those of skill in the art will recognize that each of these groups may in turn be substituted. Examples of linkers include, but are not limited to, pH-sensitive linkers, protease cleavable peptide linkers, nuclease sensitive nucleic acid linkers, lipase sensitive lipid linkers, glycosidase sensitive carbohydrate linkers, hypoxia sensitive linkers, photo-cleavable linkers, heat-labile linkers, enzyme cleavable linkers (e.g., esterase cleavable linker), ultrasound-sensitive linkers, and x-ray cleavable linkers.

The term "pharmaceutically acceptable counter ion" refers to a pharmaceutically acceptable anion or cation. In various embodiments, the pharmaceutically acceptable counter ion is a pharmaceutically acceptable ion. For example, the pharmaceutically acceptable counter ion is selected from citrate, matate, acetate, oxalate, chloride, bromide, iodide, nitrate, sulfate, bisulfate, phosphate, acid phosphate, isonicotinate, acetate, lactate, salicylate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)). In some embodiments, the pharmaceutically acceptable counter ion is selected from chloride, bromide, iodide, nitrate, sulfate, bisulfate, phosphate, acid phosphate, citrate, malate, acetate, oxalate, acetate, and lactate. In particular embodiments, the pharmaceutically acceptable counter ion is selected from chloride, bromide, iodide, nitrate, sulfate, bisulfate, and phosphate.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

If the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

A pharmaceutically acceptable salt can be derived from an acid selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isethionic, isobutyric acid, lactic acid, lactobionic acid, lauric acid, maleic acid, malic acid, malonic acid, mandelic acid, methanesulfonic acid, mucic, naphthalene-1,5-disulfonic acid, naphthalene-2-sulfonic acid, nicotinic acid, nitric acid, oleic acid, oxalic acid, palmitic acid, pamoic acid, pantothenic, phosphoric acid, proprionic acid, pyroglutamic acid, salicylic acid, sebacic acid, stearic acid, succinic acid, sulfuric acid, tartaric acid, thiocyanic acid, toluenesulfonic acid, trifluoroacetic, and undecylenic acid.

The term "bioavailable" is art-recognized and refers to a form of the subject invention that allows for it, or a portion of the amount administered, to be absorbed by, incorporated to, or otherwise physiologically available to a subject or patient to whom it is administered.

Pharmaceutical Formulations

A variety of pharmaceutical formulations are provided for treating spinobulbar muscular atrophy in a subject in need thereof. In some aspects, the formulations contain an effective amount of a selective androgen receptor modulator. In some aspects, the formulations contain an effective amount of a small molecule having a structure according to the following formula:

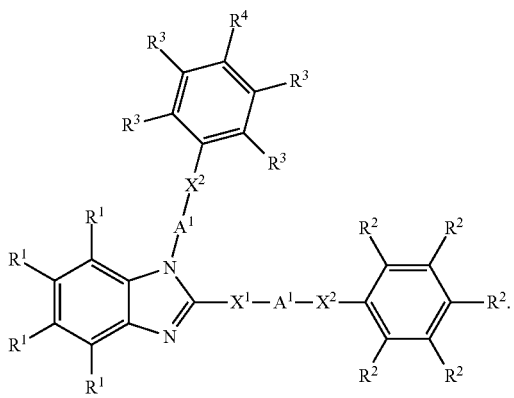

In the above formula, each occurrence of $R^1$, $R^2$, $R^3$, and $R^4$ can be chosen independently to be a suitable substituent. In some aspects, each occurrence of $R^1$, $R^2$, $R^3$, and $R^4$ is independently a hydrogen, a hydroxyl, a halogen, or a substituted or unsubstituted $C_1$-$C_{12}$, $C_1$-$C_{10}$, $C_1$-$C_6$, $C_2$-$C_{12}$, or $C_2$-$C_6$ alkyl or alkoxy. In the above formula, each occurrence of $X^1$ and $X^2$ can be independently a heteroatom, e.g. O or S. In the above formula, each occurrence of $A^1$ is independently none (i.e. is a bond) or is a substituted or unsubstituted $C_1$-$C_{12}$, $C_1$-$C_{10}$, $C_1$-$C_6$, $C_2$-$C_{12}$, or $C_2$-$C_6$ alkyl.

The formulations can contain an effective amount of a selective androgen receptor modulator. The term "selective androgen receptor modulator," as used herein, refers to a class of androgen receptor ligands that exhibit their activity in a tissue selective manner. In other words, tissue selectivity allows a nuclear receptor ligand to function as an agonist in some tissues, while having no effect or even an antagonist effect in other tissues. A synthetic compound that binds to an intracellular receptor and mimics the effects of the native hormone is referred to as an agonist. A compound that inhibits the effect of the native hormone is called an antagonist. The term "modulators" can refer to compounds that have a spectrum of activities ranging from full agonism to partial agonism to full antagonism.

The selective androgen receptor modulator can selectively bind to the androgen receptor. In some aspects, the selective androgen receptor modulator can selectively bind to the binding function-3 (BF3) domain of the androgen receptor.

In some aspects, the selective androgen receptor modulator alters a co-regulator binding to the activation function-2 (AF2) domain of the androgen receptor. For example, the selective androgen receptor modulator can partially or completely inhibit co-regulator binding to the activation function-2 (AF2) domain of the androgen receptor.

The term "selectively binds" refers to the ability of a selective binding compound to bind to a target receptor or to a specific binding domain with greater affinity than it binds to a non-target receptor or binding domain. In certain aspects, selective binding refers to binding to a target with an affinity that is at least 10, 50, 100, 250, 500, or 1000 times greater than the affinity for a non-target. The term "target receptor" refers to a receptor or a portion of a receptor capable of being bound by a selective binding compound. In certain aspects, a target receptor is an androgen receptor, and in particular in certain aspects the target receptor is the binding function-3 (BF3) domain of the androgen receptor.

In some aspects, the selective androgen receptor modulator is a small molecule described herein. In some aspects, the selective androgen receptor modulator is 17α-methyl-17β-hydroxy-2-oxa-5α-androstan-3-one or a derivative thereof. 17α-methyl-17β-hydroxy-2-oxa-5α-androstan-3-one, also known as Oxandrolone, is marketed under the brand names OXANDRIN by Gemini Laboratories (NJ, USA). In some aspects, the selective androgen receptor modulator is testosterone or a derivative thereof. In some aspects, the selective androgen receptor is a testosterone ester such as testosterone enanthate, testosterone propionate, or testosterone cypionate. In some aspects, the selective androgen receptor modulator is 4,5α-dihydrotestosterone or a derivative thereof. In some aspects, the selective androgen receptor modulator is ((2S)-3-(4-cyanophenoxy)-N-[4-cyano-3-(trifluoromethyl)phenyl]-2-hydroxy-2-methylpropanamide) or a derivative thereof. ((2S)-3-(4-cyanophenoxy)-N-[4-cyano-3-(trifluoromethyl)phenyl]-2-hydroxy-2-methylpropanamide), also known as ostarine or enobosarm, is an investigational selective androgen receptor developed by Merck and Company (NJ, USA).

In some aspects, the pharmaceutical formulation includes a derivative of the small molecule or a derivative of a selective androgen receptor modulator described herein. Suitable derivatives can include ester and amide derivatives, pegylated derivatives, and N-oxides. The derivative can include replacing or substituting one of more R groups with a substituent such as a substituent selected from the group consisting of a halogen, an azide, an alkyl, an aralkyl, an alkenyl, an alkynyl, a cycloalkyl, a hydroxyl, an alkoxyl, an amino, a nitro, a sulfhydryl, an imino, an amido, a phosphonate, a phosphinate, a carbonyl, a carboxyl, a silyl, an ether, an alkylthio, a sulfonyl, a sulfonamido, a ketone, an aldehyde, a thioketone, an ester, a heterocyclyl, a —CN, an aryl, an aryloxy, a perhaloalkoxy, an aralkoxy, a heteroaryl, a heteroaryloxy, a heteroarylalkyl, a heteroaralkoxy, an azido, an alkylthio, an oxo, an acylalkyl, a carboxy esters, a carboxamido, an acyloxy, an aminoalkyl, an alkylaminoaryl, an alkylaryl, an alkylaminoalkyl, an alkoxyaryl, an arylamino, an aralkylamino, an alkylsulfonyl, a carboxamidoalkylaryl, a carboxamidoaryl, a hydroxyalkyl, a haloalkyl, an alkylaminoalkylcarboxy, an aminocarboxamidoalkyl, a cyano, an alkoxyalkyl, a perhaloalkyl, and an arylalkyloxyalkyl.

In some aspects, the pharmaceutical formulation includes a prodrug of the small molecule or a derivative thereof. Methods of making prodrugs are known in the art, and can include an amide, carbamate, imide, ester, anhydride, thioester, or thioanhydride of the small molecule or derivative thereof.

In some aspects, the pharmaceutical formulation includes a salt of the small molecule or a derivative or prodrug thereof. The salt can be a pharmaceutically acceptable acid addition salt including an anion such as a sulfate, a citrate, matate, an acetate, an oxalate, a chloride, a bromide, an iodide, a nitrate, a sulfate, a bisulfate, a phosphate, an acid phosphate, an isonicotinate, an acetate, a lactate, a salicylate, a tartrate, an oleate, a tannate, a pantothenate, a bitartrate, an ascorbate, a succinate, a maleate, a gentisinate, a fumarate, a gluconate, a glucaronate, a saccharate, a formate, a benzoate, a glutamate, a methanesulfonate, an ethanesulfonate, a benzenesulfonate, a p-toluenesulfonate or a pamoate (i.e., 1,1'-methylene-bis-(2-hydroxy-3-naphthoate)). The salt can be a base addition salt including an alkali metal and alkaline earth metal cation, such as calcium, magnesium, sodium, lithium, zinc, potassium, or iron.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C 1-to-C 6 alkyl esters and C 5-to-C 7 cycloalkyl esters, although C 1-to-C 4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C 1-to-C 6 alkyl amines and secondary C 1-to-C 6 dialkyl amines. In the case of secondary amines, the amine can also be in the form of a 5- or 6-membered heterocycle containing one nitrogen atom. Amides derived from ammonia, C 1-to-C 3 alkyl primary amides and C 1-to-C 2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

In some aspects, the small molecule is -[2-(4-methylphenoxy)ethyl]-2-[(2-phenoxyethyl)sulfanyl]-1H-benzimidazole having a structure according to the following formula

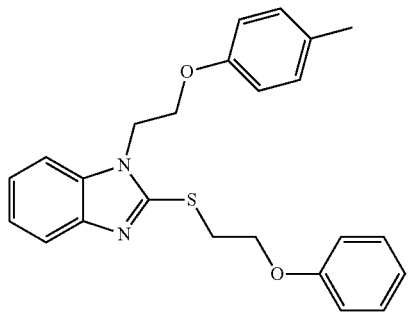

The formulations include a therapeutically effective amount of the small molecule or a selective androgen receptor modulator or a derivative, prodrug, or salt thereof. In some aspects, the therapeutically effective amount is effective to prevent or delay loss of body weight, a loss of mobility, and/or a loss of physical strength in the subject. In some aspects, the therapeutically effective amount is effective to prevent or delay neurogenic atrophy and/or to prevent a loss of spinal cord motor neurons in the subject. In some aspects, the therapeutically effective amount is effective to restore the frequency of type I myofibers to normal levels for a healthy subject. In some aspects, the therapeutically effective amount is effective to reverse testicular atrophy in the subject.

Parenteral Formulations

The small molecules or a derivative, prodrug, or salt thereof can be formulated for parenteral delivery, such as injection or infusion, in the form of a solution or suspension.

The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the small molecules can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the small molecule(s) or active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the small molecules in the required amount in the appropriate solvent or dispersion medium with one or more of the excipients listed above, as required, followed by filtered sterilization. Generally, dispersions are prepared by incorporating the various sterilized small molecules into a sterile vehicle which contains the basic dispersion medium and the required other ingredients from those listed above. In the case of sterile powders for the preparation of sterile injectable solutions, the methods of preparation can include vacuum-drying and freeze-drying techniques which yield a powder of the small molecules plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of particles formed from one or more small molecules. Acceptable solvents include, for example, water, Ringer's solution, phosphate buffered saline (PBS), and isotonic sodium chloride solution. The formulation may also be a sterile solution, suspension, or emulsion in a nontoxic, parenterally acceptable diluent or solvent such as 1,3-butanediol.

In some instances, the formulation is distributed or packaged in a liquid form. Alternatively, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for parenteral administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for parenteral administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for parenteral administration may also contain one or more excipients known art, such as dispersing agents, wetting agents, and suspending agents.

Enteral Formulations

The small molecules or a derivative, prodrug, or salt thereof can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations are prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include hydrophobic or hydrophilic polymers and pH dependent or independent polymers. Preferred hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins.

Carrier also includes all components of the coating composition which may include plasticizers, pigments, colorants, stabilizing agents, and glidants.

Formulations can be prepared using one or more pharmaceutically acceptable excipients, including diluents, preservatives, binders, lubricants, disintegrators, swelling agents, fillers, stabilizers, and combinations thereof.

Delayed release dosage formulations can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The small molecules can be formulated in nanoparticles or in various capsule forms which may be coated, for example to delay release when passing through the acidic environment of the stomach. Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers and/or pH dependent polymers, with or without water insoluble/water soluble non polymeric excipient, to produce the desired release profile. The coating is either performed on dosage form (matrix or simple) which includes, but not limited to, tablets (compressed with or without coated beads), capsules (with or without coated beads), beads, particle compositions, "ingredient as is" formulated as, but not limited to, suspension form or as a sprinkle dosage form.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

Methods of Treating Spinobulbar Muscular Atrophy

In various aspects, methods are provided for treating spinobulbar muscular atrophy in a subject in need thereof. It is to be understood that, as spinobulbar muscular atrophy is a genetic disorder, treating can include impeding the progress of spinobulbar muscular atrophy, causing regression of the spinobulbar muscular atrophy, amelioration of at least one symptom of spinobulbar muscular atrophy, even if the underlying genetic disorder remains unaffected. Treating can include treating the underlying pain associated with spinobulbar muscular atrophy even without alleviating additional symptoms.

The methods can include administering a therapeutically effective amount of a small molecule described herein or a derivative, prodrug, or salt thereof. The methods can include administering a pharmaceutical formulation described herein. In some aspects, the administration is via intravenous injection, intradermal injection, intramuscular injection, subcutaneous injection, infusion, or a combination thereof. In some aspects, the subject is a human subject.

Spinal and bulbar muscular atrophy is a gradually progressive neuromuscular disorder in which degeneration of lower motor neurons results in muscle weakness, muscle atrophy, and fasciculation. Affected individuals often show gynecomastia, testicular atrophy, and reduced fertility. The therapeutically effective amount can effective to delay loss of body weight, a loss of mobility, and/or a loss of physical strength in the subject. The delay can include delaying the onset as compared to a subject not receiving the treatment and/or decreasing the rate of loss as compared to a subject not receiving the treatment. The therapeutically effective amount can be effective to prevent or delay neurogenic atrophy and/or to prevent a loss of spinal cord motor neurons in the subject. The therapeutically effective amount can be effective to restore the frequency of type I myofibers to normal levels for a healthy subject. The therapeutically effective amount can be effective to reverse, delay the onset of, or delay the progression of testicular atrophy in the subject.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1: MEPB Yields Dose-Dependent Rescue from Loss of Body Weight, Rotarod Activity, and Grip Strength and Ameliorates Neuronal Loss, Neurogenic Atrophy, and Testicular Atrophy in SBMA Spinal bulbar muscular atrophy (SBMA) is a motor neuron disease caused by toxic gain-of-function of the androgen receptor (AR). Previous studies have shown that coregulator binding through the activation function-2 (AF2) domain of AR may be a druggable target for selective modulation of toxic AR activity. Here we screened previously identified AF2 modulators for their ability to rescue toxicity in a Drosophila model of SBMA. We identified two compounds, tolfenamic acid (TA) and 1-[2-(4-methylphenoxy)ethyl]-2-[(2-phenoxyethyl)sulfanyl]-1H-benzimidazole (MEPB), as top candidates for rescuing lethality, locomotor function, and neuromuscular junction defects in SBMA flies. Pharmacokinetic analyses in mice showed good bioavailability of MEPB and poor bioavailability of TA in muscle, brain, and spinal cord. In a preclinical trial in a mouse model of SBMA, MEPB treatment yielded a dose-dependent rescue from loss of body weight, rotarod activity, and grip strength. In addition, MEPB ameliorated neuronal loss, neurogenic atrophy, and testicular atrophy, validating AF2 modulation as a potent androgen-sparing strategy for SBMA therapy.

Materials and Methods

Study Design

The objective of this study was to determine whether modulation of the AR AF2 domain by small molecules that specifically bind to the BF3 regulatory pocket would be a practicable therapy for improving the QOL of patients with SBMA. To this end, we screened several BF3-specific compounds in *Drosophila*; performed a pilot preclinical study of the top two candidate compounds; performed an extensive, multidose preclinical study of the lead compound; and determined the mechanism of action of these compounds in cell culture studies. *Drosophila* NMJ staining and analysis was performed in a blinded manner, whereby treated larvae were coded by an independent investigator. Treatment groups were not uncoded until analyses were completed. Both preclinical trials were performed in a blinded manner, whereby drugs (i.e., vehicle, TA, and/or MEPB) were assigned a specific code by an independent investigator. Treatment groups remained blinded until data collection and analysis were complete. Drug dose and animal numbers were determined empirically for the pilot preclinical study. The data acquired from this study were used in a power analysis to estimate the number of animals required for the large preclinical study. Animal endpoints were reached when a mouse exhibited hindlimb paralysis/paresis or greater than 10% loss of bodyweight, at which point the animal was humanely euthanized. Because the yield of AR121Q-positive male mice was generally low throughout our studies, randomization was not possible. Mice were entered into treatment groups as they became available and were followed longitudinally. Replicate number and statistical tests for each dataset are provided in the figure legends.

Reagents

For fly and cell culture experiments, TA (Sigma Aldrich), MEPB (Specs), bicalutamide (3B Scientific Corporation), ibuprofen (Sigma Aldrich), or dimethylcurcumin (Cayman Chemical) were resuspended in DMSO (Sigma Aldrich), whereas DHT (Steraloids) was dissolved in ethanol, prior to addition to fly food or culture media. All cell culture experiments were performed in media containing 10% charcoal-dextran stripped serum (Hyclone) to remove exogenous steroid hormones. For preclinical and pharmacokinetic mouse studies, TA and MEPB were dissolved in either a 10 mg/mL (low dose) or 20 mg/mL (high dose) solution of corn oil containing 1% DMSO at 37° C. for approximately 12 h, filtered (0.22 μm filter), and stored at 4° C. until injection.

Molecular Modeling

BF3-unbound AR LBD (pdb1T7R) in complex with an FXXLF motif was modeled using PyMOL software. BF3 residues (I690, F691, P723, G724, N727, F826, E829, N833, E837, and R840) were highlighted green, charge clamp residues of the AF2 domain (K720, M734, M894, and E897) were highlighted red, and a synthetic FXXLF (FESLF) motif was highlighted blue. MEPB modeling was performed in the same manner using pdb2YLO. TA modeling was performed in a similar manner using pdb2PIX, whereby flufenamic acid was removed and TA was added according the lowest predicted energy conformation using SwissDock software.

Fly Stocks and Phenotypic Characterization

UAS-AR52Q, UAS-AR52Q-K720A, and UAS-AR66Q-E897K fly stocks were generated as previously described[8]. Fly stocks were crossed to various GAL4 driver lines (ELAV-GAL4 for pan-neuronal, OK371-GAL4 for motor neuron, GMR-GAL4 for eye) to induce expression of the AR transgene in a tissue-specific manner in fly vials containing fly food with either vehicle (1% ethanol +/−0.1% DMSO) or drugs. Upon the presence of progeny, parental flies were removed, and F1 flies were scored for phenotypic analysis. Viability was determined as previously described[40]. Briefly, the population frequency of adult F1 SBMA flies (ELAV>UAS-AR52Q or OK371>UAS-AR52Q) and control flies (GAL4-ELAV; CyO-GFP) were determined by the presence or absence of the CyO phenotypic marker. At least three independent biological replicates (F0 crosses) were performed with new drug/food preparations for each treatment group, and a total of at least 50 flies were scored for each treatment group. To determine locomotor activity of SBMA flies, adult F1 flies (OK371>UAS-AR52Q) reared on food containing vehicle or drug were allowed to walk for 90 seconds in one well of a 12-well tissue culture plate while video was recorded using a Leica M205C stereomicroscope and Leica DFC320 digital camera. Videos were recorded for at least 15 flies per treatment group. Tracing of fly movement and analysis of displacement and velocity were performed using ImageJ software. Preparation and staining of larval neuromuscular junctions and ventral ganglions were performed as previously described[8].

Generation of AR121Q Transgenic Mice and Surgical Castration

Human AR cDNA containing 121 CAG/CAA alternating repeats was subcloned into the pCAGGS vector. An 11.5 kb fragment containing the pCAGGS promoter and AR cDNA was released by ApaL1 digestion, purified by QIAEXII (Qiagen), and injected into FVB pronuclei, which were transferred into female FVB recipients. Founders were screened by DNA genotyping of tail biopsies. Fluorescence in situ hybridization analysis was performed on lung tissue to confirm transgene insertion. Out of 15 founders, one line was viable, demonstrated germline transmission, and expressed levels of hAR protein comparable with that of endogenous mouse AR. Therefore, the phenotype of this line was extensively characterized. Mice were maintained on a purebred FVB background for all studies.

Castration was performed according to USDA guidelines for aseptic technique in animal survival surgery and oversight was provided by veterinary staff at St. Jude Children's Research Hospital. Briefly, mice were anesthetized by isoflurane exposure, and the surgical site was prepared by shaving and disinfection. A 10-mm incision was made along the scrotal midline, and the testes were removed using forceps. The connection between the testes and vas deferens, as well the associated blood vessels, were cauterized by hot forceps. Incisions were closed using tissue glue, and preemptive analgesia (0.2 mg/kg meloxicam) was administered. Mice were bred and maintained in accordance with the guidelines set forth by the National Institutes of Health Guide for the Care and Use of Laboratory Animals, published by the U.S. Public Health Service. All experimental protocols were approved by the Institutional Animal Care and Use Committee at St. Jude Children's Research Hospital.

Preclinical Trial Design in AR121Q Mice

To determine the efficacy of TA and/or MEPB in a mouse model of SBMA, we first performed a pilot study. Five mice were assigned to each drug treatment group: 50 mg/kg TA, 50 mg/kg MEPB, or vehicle (1% DMSO in corn oil). Drug identities were coded to ensure investigator blinding, and drugs were administered three times per week (Monday, Wednesday, and Friday) by intraperitoneal injection from 3 to 8 weeks of age. At 8 weeks, all mice were sacrificed and tissues were collected for pathologic analysis. To fully characterize the efficacy of MEPB in SBMA mice, a large-scale, multi-dose preclinical trial was performed. A power analysis (Table 1) was performed based on the pilot study data to determine the adequate number of mice required for 80% power. At least 10 mice were assigned to each drug treatment group: 50 mg/kg MEPB, 100 mg/kg MEPB, and vehicle (1% DMSO in corn oil). Drug identities were coded to ensure investigator blinding, and drugs were administered three times per week (Monday, Wednesday, and Friday) by intraperitoneal injections from 4 weeks until 30 weeks of age.

TABLE 1

Statistical variables used to determine sample size

| Assay | Type I error rate | Power | Detection difference | Minimum number of mice/group required |
|---|---|---|---|---|
| Body weight | 0.05 | 0.8 | 4 g | 4 |
| Rotarod | 0.05 | 0.8 | 50 s | 5 |
| Grip strength | 0.05 | 0.8 | 20 g | 10 |
| Survival | 0.05 | 0.8 | 47% | 10 |

AR121Q Mouse Phenotypic Characterization

Body weight, rotarod activity, and grip strength data were collected weekly. Footprint analysis and clasping phenotype were assessed at 7 and 8 weeks of age. Body weight was measured using a standard laboratory scale (Fisher Scientific). Rotarod activity analysis was performed on an accelerating rotarod apparatus (IITC Life Science) using a two-day, weekly protocol. Mice were trained on the first day with one session set at 4 rpm for 5 min. The following day, mice were placed on the apparatus, rotation speed was set to accelerate from 4-40 rpm at a rate of 0.1 rpm/s, and the latency to fall was recorded for four separate trials per mouse. Mice were given a 15-min rest period between each trial. Grip strength was measured using a grip strength meter (Bioseb). Grip strength was measured as grams of force in six repeated measurements for forepaws and hindpaws of each animal. To perform gait/footprint analysis, the forepaws and hindpaws of each animal were dipped in red and blue, respectively, water-soluble, non-toxic paint. The animal was then placed in a 70-cm long tunnel lined on the bottom with Whatman filter paper, the entrance was sealed, and the animal was allowed to walk through one time. Footprints were scanned and analyzed with Image J for stride length and forepaw/hindpaw overlap[41]. To determine clasping phenotype, mice were recorded using an Apple iPod camera (iOS version 6.1.6) for approximately 60 seconds and still frames were extracted using ImageJ.

AR121Q Mouse Pathologic Assessment

A separate cohort of five mice per treatment group was generated for pathologic and biochemical analysis. Mice were anesthetized by isoflurane inhalation and transcardially perfused with either PBS for frozen tissue samples or 10% formalin for fixed tissue samples. Selected tissues (brain, spinal cord, gastrocnemius/soleus muscle, testes, and liver) were dissected and either snap-frozen in liquid nitrogen or processed for paraffin embedding/sectioning. Tissue sections were stained with hematoxylin and eosin, toluidine blue, or Gomori trichrome to ascertain overall morphology and pathologic changes. To determine AR staining and colocalization patterns, tissue sections were stained with anti-AR (N20, Santa Cruz), anti-polyQ (5TF1-1C2, EMD Millipore), or anti-ubiquitin (Cell Signaling Technology) antibodies. To quantify type I and type II myofibers, hindlimb tissue sections were stained with myosin heavy chain-slow twitch and myosin heavy chain-fast twitch antibodies (Leica Biosystems), respectively. For the purposes of counting ChAT-positive neurons, three stepped sections separated by 50 μm were analyzed for the cervical, thoracic, and lumbosacral areas of spinal cords. The slides contained three to six tissue sections at each level and were labeled with an anti-ChAT antibody (EMD Millipore). All slides were digitally scanned at scalable magnifications up to 20× (objective lens) using an Aperio XT Slide Scanner (Leica Biosystems). Whole slide images were imported into the Halo software program (Indica Labs) and positive staining was quantified by an area quantification algorithm. For spinal cord motor neuron quantification, static images were made at a 2× magnification with ImageScope (Leica Biosystems) and the number of ChAT-positive neurons located within the anterior horn were counted with FIJI software[42].

Pharmacokinetics

MEPB and TA concentrations in plasma, liver, muscle, testes, brain, and spinal cord of male FVB/NJ mice were measured at multiple time points (5 min to 48 h) after a single intraperitoneal injection of either 100 mg/kg body weight MEPB or 50 mg/kg body weight TA. MEPB or TA and the internal standard (IS) SLV320 (Tocris Biosciences) were extracted from plasma and tissue homogenate samples with methyl tert-butyl ether. A 25-µL aliquot of sample was mixed with 10 µL IS (100 ng/mL). To this, 600 µL methyl tert-butyl ether was added and vortexed for 5 min. After centrifugation at 10,000 rpm for 5 min, the organic layer was then transferred to a glass vial and dried in a CentriVap Console (Labconco) at 35° C. for 25 min. The dried extracts were then reconstituted with 400 µL methanol, and an aliquot of 3 µL was injected onto the chromatographic system. All chemicals were HPLC grade or higher and were obtained from Fisher Scientific (Fair Lawn) unless otherwise specified. Quantitation of MEPB and TA was performed using an API 4000 mass spectrometer (AB SCIEX) equipped with a Prominence Ultra-Fast Liquid Chromatograph (UFLCXR) system (Shimadzu). Chromatographic separation was achieved with a Phenomenex Luna C18 column (3 µm, 100 A° 50×2.00 mm) by using mobile phases consisting of 0.1% formic acid in water (A) and acetonitrile (B). Mass spectrometric analysis was performed with the turbo ion spray in positive ionization mode. All MS data were acquired using Analyst 1.5.2 software and processed using MultiQuant 2.1.1 software (SCIEX).

For all matrices (plasma, liver, muscle, testes, brain, and spinal cord), the lower limit of quantification (LLOQ) of MEPB was 2.5 ng/mL with a calibration range of 2.5 ng/mL to 100 ng/mL. However, due to dilution during homogenization, the effective LLOQ was 15 ng/mL for solid tissues. The LLOQ of TA was 5 ng/mL for plasma and 60 ng/mL for tissues. Assays were found to be linear and reproducible with a correlation coefficient (R)>0.99. The MEPB concentration-time (Ct) data for liver, muscle, testes, brain, and spinal cord were grouped by mouse and analyzed using a two-stage, semiphysiologic, nonlinear mixed effects approach with maximum likelihood expectation maximization in ADAPT 5. The pooled arithmetic mean Ct data were subjected to noncompartmental analysis by tissue using WinNonlin 6.4 (Pharsight, a Cetara Company). All PK parameters were calculated using standard formulae[43]. Parameters estimated for all matrices included observed maximum concentration (Cmax), time of Cmax (Tmax), concentration at the last observed time point (Clast), time of Clast (Tlast), and area under the Ct curve (AUC). When applicable, the terminal phase was defined as the three time points at the end of the Ct profile, excluding Cmax, and the elimination rate constant (Kel) was estimated using an unweighted log-linear regression of the terminal phase. The terminal elimination half-life (T½) was estimated as 0.693/Kel, and the AUC from time 0 to infinity (AUCinf) was estimated as the AUC to the last time point (AUClast)+Clast/Ke. Apparent clearance (CL/F=Dose/AUCinf), and apparent terminal volume of distribution (Vz/F) were also calculated.

Immunoblotting and Immunofluorescence

Lysates from mouse tissues were prepared by grinding snap-frozen tissues on dry ice with a pestle until pulverized into a fine powder, resuspending in ice-cold RIPA (1% Triton-X, 0.1% sodium deoxycholate, and 0.1% SDS in Tris/NaCl) buffer, briefly sonicating, and centrifuging at 14,000 g for 20 min. Drosophila lysates were prepared as previously described[8]. Cell lysates were prepared by scraping transfected (mycoplasma-free) HEK293T cells (ATCC) or MN1 (first described by Brooks et al. (1997)[44], gift from Kurt Fischbeck) cells into room temperature PBS, centrifuging at 400 g for 5 min, and resuspending pellets in ice-cold RIPA buffer, briefly sonicating, and centrifuging at 14,000 g for 20 min. Supernatants were then collected, and protein levels were measured and adjusted using Bradford analysis. Proteins were separated on 4% to 20% or 8% Tris-glycine gels and transferred overnight at 4° C. onto PVDF membranes. Membranes were stained with REVERT total protein stain (Li-Cor) and immunoblotted using anti-AR (H280 or N20 [Santa Cruz], D6F11 [Cell Signaling Technologies], or EPR1535(2) [Abcam]), anti-tubulin (Sigma Aldrich), anti-GAPDH (Cell Signaling Technologies), or anti-β-actin (Santa Cruz) antibodies. Filter trap assay for aggregation was performed by resuspending cell lysates in a 10% SDS buffer to achieve a final 2% SDS concentration, heating for 5 min at 95° C., and applying to a 0.22 µm cellulose acetate membrane (GE Healthcare Life Sciences) with a vacuum dot blot apparatus (Schleicher and Schuell). Membranes were washed three times with 0.1% SDS and blotted with anti-FLAG (M2, Sigma Aldrich). For immunofluorescence experiments in Drosophila, UAS-AR flies were crossed to OK371-GAL4 flies at 25° C. on food containing either 1 mM DHT (Steraloids) or 1% ethanol together with indicated drug. Third instar larvae were heat killed, dissected in PBS, and fixed with 4% PFA for 20 minutes. Primary antibody staining was performed at 4° C. overnight and secondary antibody staining was performed at room temperature for 4 hours. After staining, pelts were mounted in Fluoromount-G (SouthernBiotech). For immunofluorescence experiments in mice, deparaffinized and rehydrated cross-sections of spinal cord and hindlimb muscle were permeabilized in 2% Triton-X 100, treated with TrueBlack autofluorescence quencher (Biotium), and blocked in PBS with 4% BSA and 2% NGS. Sections were incubated overnight at 4° C. with anti-NCAM (Proteintech), anti-PSA-NCAM (EMD Millipore), anti-ubiquitin (Abcam), or anti-polyQ (EMD Millipore) antibodies, followed by incubation for 2 h at room temperature with the appropriate Alexa Fluor-conjugated secondary antibodies (Thermo Fisher Scientific). Sections were mounted with ProLong Gold Antifade Mountant with DAPI (Thermo Fisher Scientific) and allowed to dry for at least 24 h at room temperature before imaging on a Leica TCS SP8 STED 3× confocal microscope (Leica Biosystems for ubiquitin-polyQ colocalization or Leica DM18 Widefield microscope for NCAM) with 40× objective and LASX software (Leica).

NCAM Imaging and Analysis

One image was acquired in a region of three to four slices where bright punctate NCAM and PSA-NCAM could be seen within the muscle fibers. If no punctate regions greater than that of autofluorescence intensity in either channel could be seen, a representative field without punctate signal was taken for that muscle slice. Imaging and analysis was performed for two mice from each of the following conditions: untreated NTG, untreated SBMA, NTG treated with 50 mg/kg MEPB, and NTG treated with 100 mg/kg MEPB. Three mice each were analyzed from each of the following conditions: SBMA treated with 50 mg/kg MEPB and SBMA treated with 100 mg/kg MEPB. The same images were subjected to colocalization analysis with LASX software. For each image, the background out-of-focus light was subtracted out and the remaining white detail was enhanced to make the punctate regions more easily recognizable by the program. Following processing, an intensity-based mask was created for each channel, recognizing the regions where the signal was above that of tissue autofluorescence. These masks were then dilated and smoothed to combine nearby punctate regions. Using a binary "AND" operand, the number of overlapping regions larger than 5 pixels that had signal in both masks was calculated. Two-way ANOVA with Dunnett multiple comparisons test was performed using GraphPad Prism version 6. $P<0.05$ was considered significant.

Luciferase Reporter Assays

To determine AR-dependent transcriptional activity, HEK293T cells were transiently transfected in culture media containing 10% charcoal-dextran stripped serum with ARE-firefly luciferase and CMV-Renilla luciferase (Cignal ARE Reporter Assay Kit, Qiagen), in addition to either FLAG-AR24Q or FLAG-AR65Q (gift from Maria Pennuto). Following 24 h of transfection, cells were washed and treated with vehicle, bicalutamide, TA, or MEPB for 24 h. Firefly and Renilla luciferase substrates (Dual-Luciferase Reporter Assay, Promega) were added, and luciferase activity was measured using a microplate spectrophotometer (BioTek). Mammalian two-hybrid assays were performed by transiently transfecting HEK293T cells with pG5Luc firefly luciferase reporter (Checkmate Mammalian Two-Hybrid kit, Promega), CMV-Renilla luciferase (Cignal ARE Reporter Assay Kit, Qiagen), and GAL4 DBD-AR LBD (gift from Elizabeth Wilson), in addition to either VP16 empty vector, VP16-NCoR, or VP16-SMRT (gifts from Vivian Bardwell) for 24 h. Cells were then washed and treated with vehicle, TA, or MEPB for 24 h. Renilla and firefly luciferase were quantified using Dual-Luciferase Reporter Assay (Promega) and a microplate spectrophotometer (BioTek).

Droplet Digital PCR

The QX200 droplet digital PCR (ddPCR) system (Bio-Rad) was used to measure gene expression levels in 20 µl emulsion PCR reactions that contain 20,000 droplets. Total RNAs were firstly treated with DNase (Thermo Fisher Scientific, AM1907) to remove genomic DNA, and 5 ng of treated RNA was used in each assay. ddPCR assay consisted of the following components: 1× one-step RT-ddPCR mix for probes (Bio-Rad, 1864021), forward primer (900 nM), reverse primer (900 nM), probe (FAM or VIC, 250 nM), nuclease-free water, and 5 ng RNA. All primers and probes were purchased from Thermo Fisher Scientific. Droplets were generated in the droplet generator (Bio-Rad) and PCR was performed in a C1000 Touch thermal cycler (Bio-Rad) according to the manufacturer's recommendation. After PCR, read-out of positive versus negative droplets was performed using the QX200 droplet reader (Bio-Rad) and calculated by QuantaSoft software version 1.7.4.0917 (Bio-Rad).

Statistical Analyses

Significant changes in *Drosophila* population frequencies (i.e., viability) were determined by Chi square analysis. Survival of SBMA mice was determined by Kaplan-Meier estimation, and comparisons between survival curves were made with the log-rank (i.e., Mantel-Cox) test. All other data, except power analysis and QOL score, were analyzed by one-way or two-way ANOVA and either Tukey or Dunnett post-hoc analysis, where appropriate, with Prism software (version 6.0, GraphPad). Power analysis was performed to determine sample size requirements to achieve 80% power using SAS software (SAS Institute). QOL scores were determined by averaging the change from baseline measurements for each behavioral phenotype (body weight, grip strength, and rotarod activity). A score of zero was applied at each time point for any animal that could not complete the task due to hindlimb paralysis or that had been euthanized. A mixed effect model was applied using SAS software to determine statistical significance.

Results

AF2 Modulation Rescues Degeneration in SBMA Flies

Figure 1B:
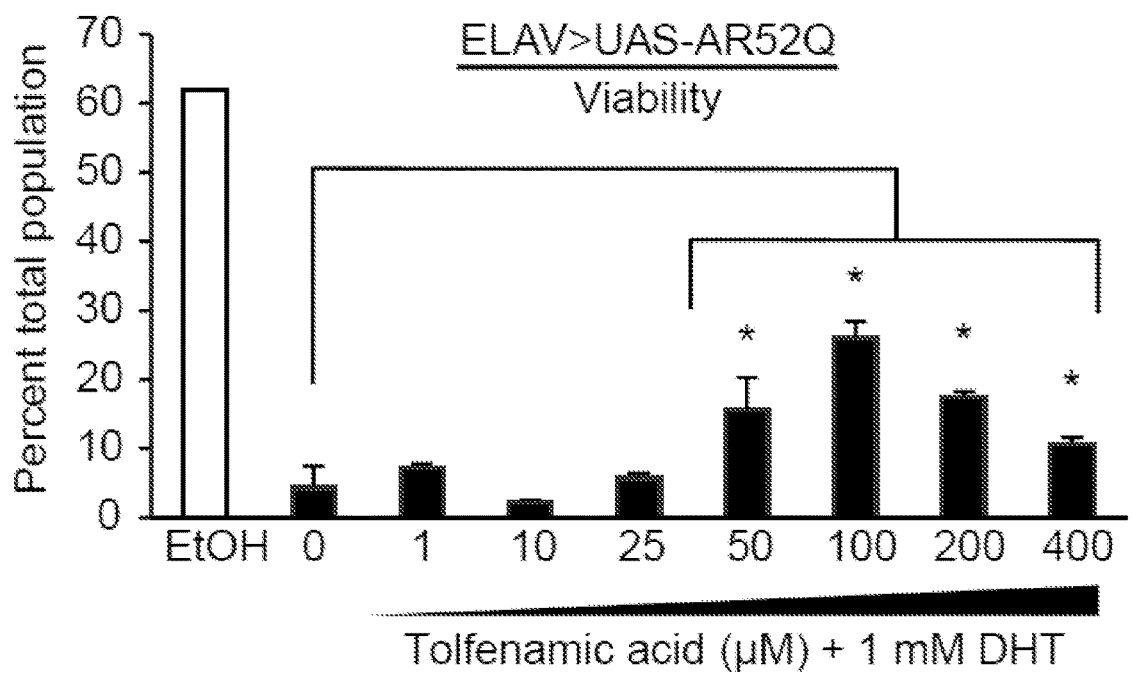
Figure 1C:
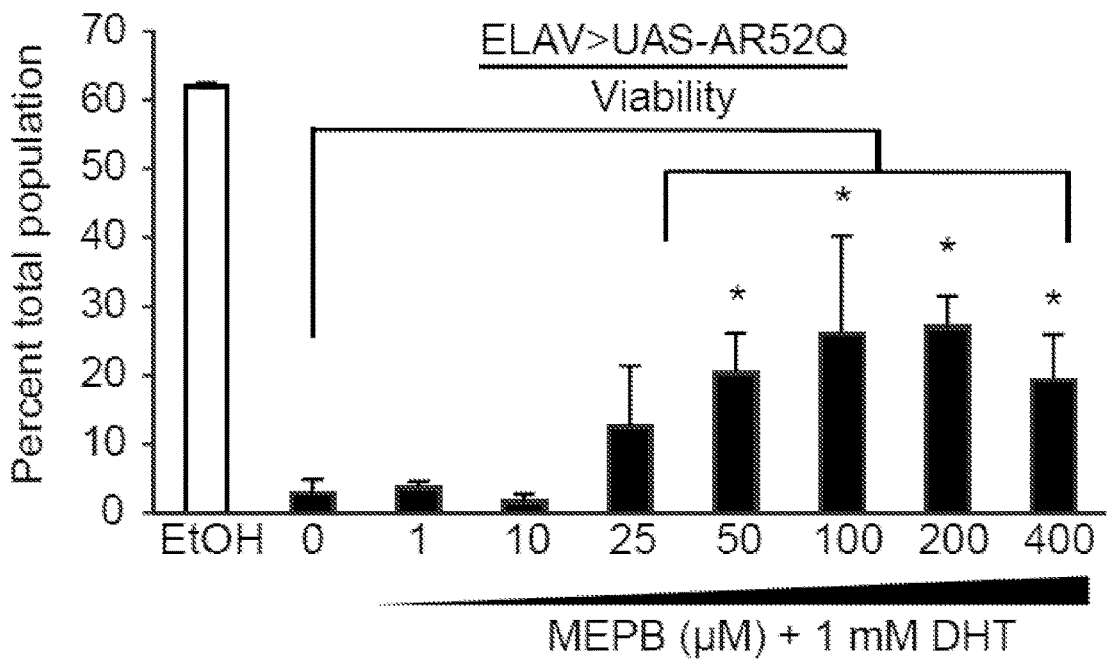
Figure 1D:
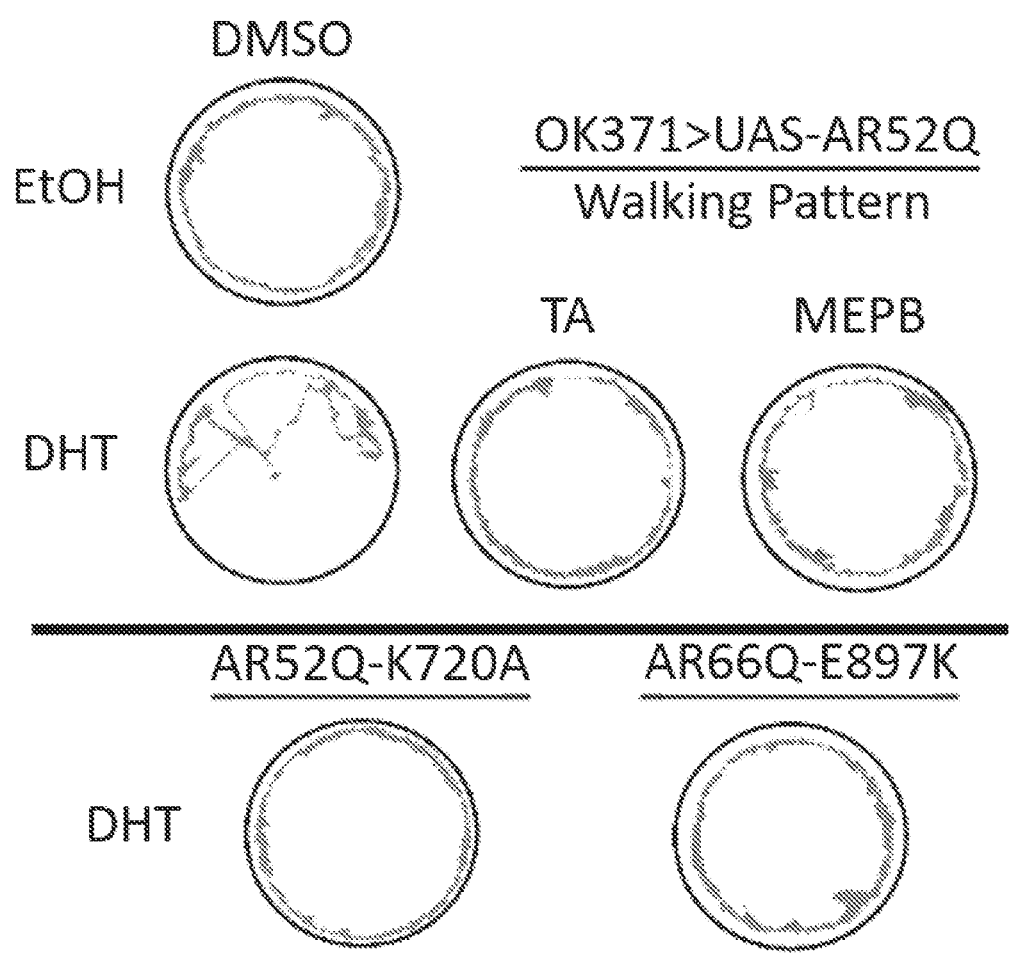
Figure 1E:
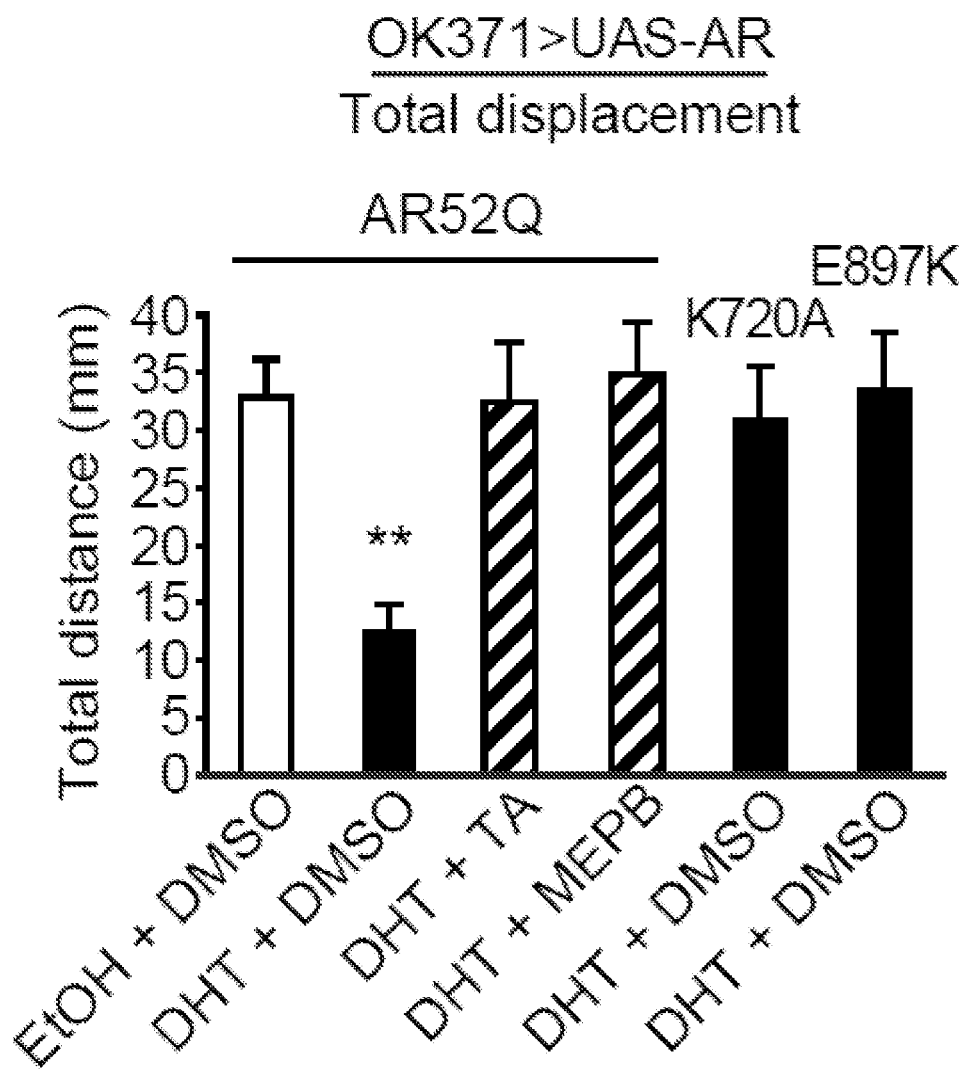
Figure 1F:
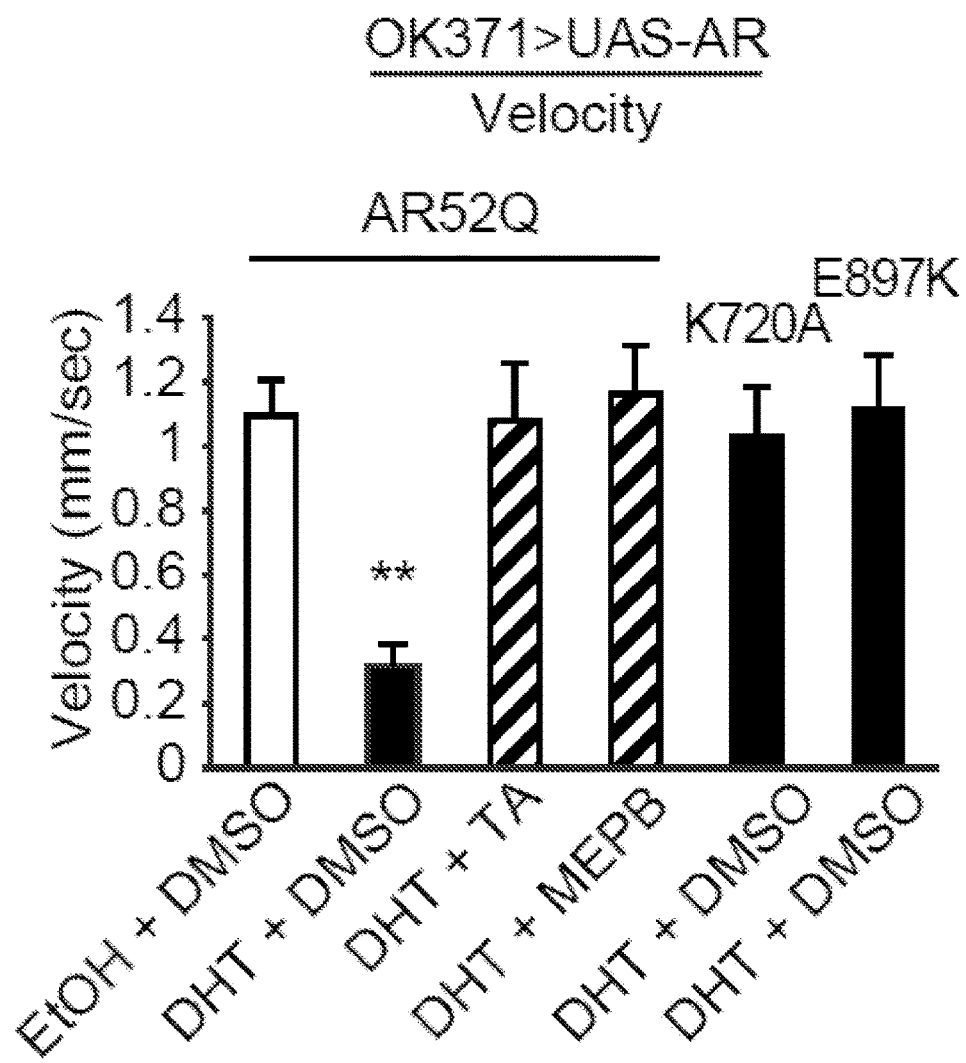
Figure 1G:
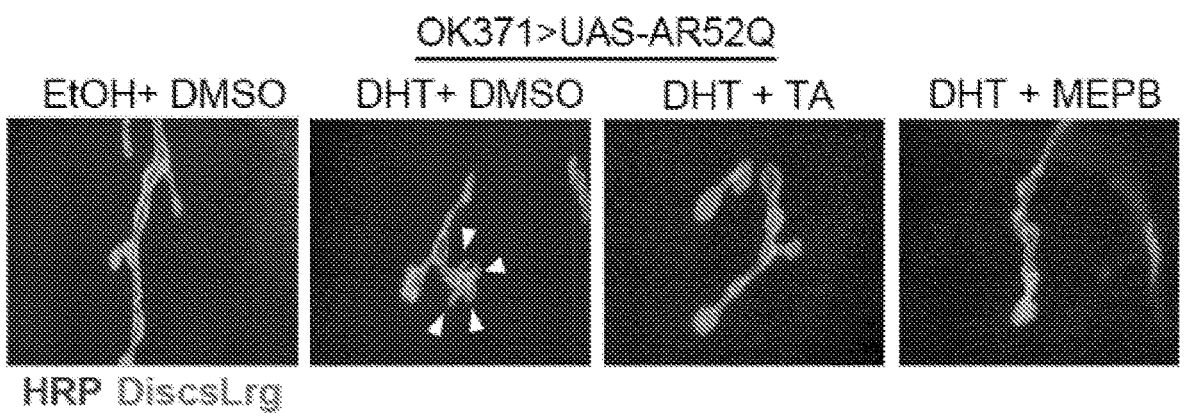
Figure 1H:
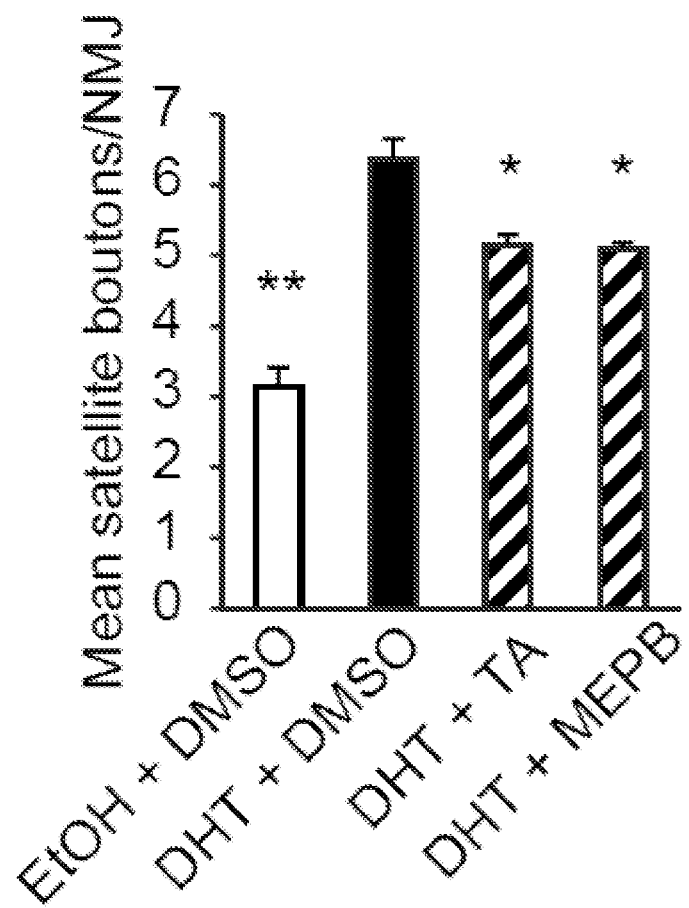
Figure 1I:
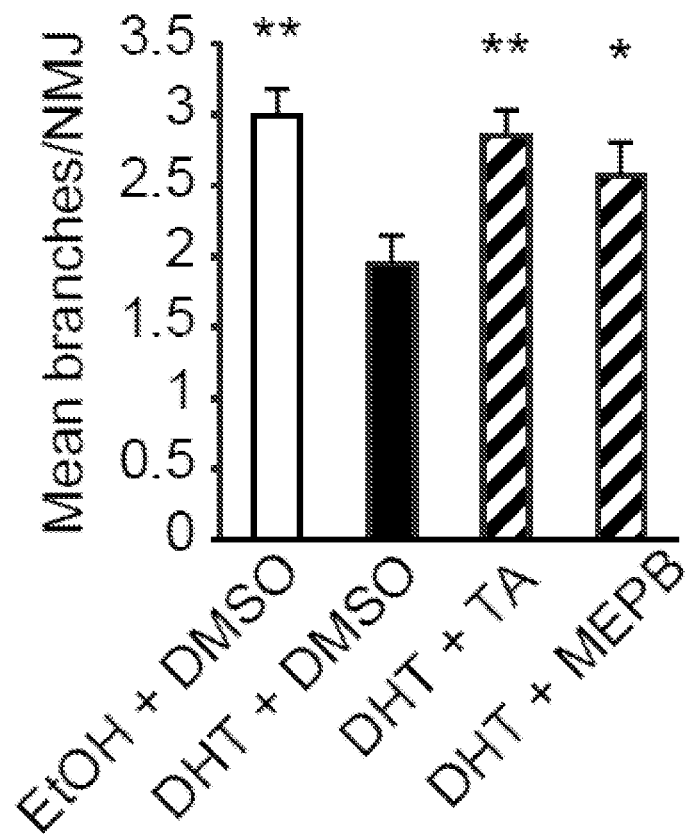
Figure 8A:
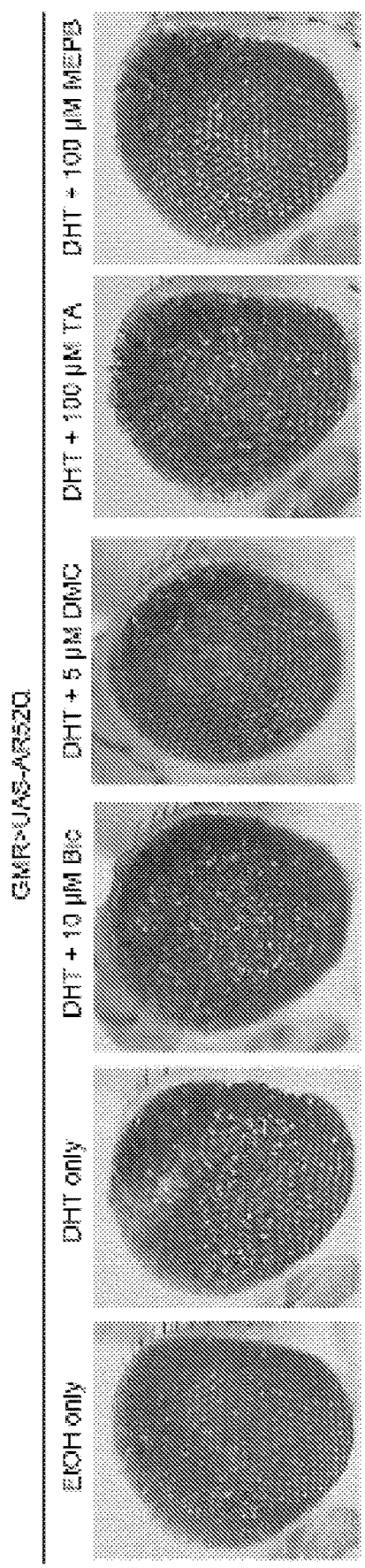
FIGS. 8A-8E demonstrate AF2 modulation rescues SBMA fly eye degeneration without reducing AR levels.
Figure 8B:
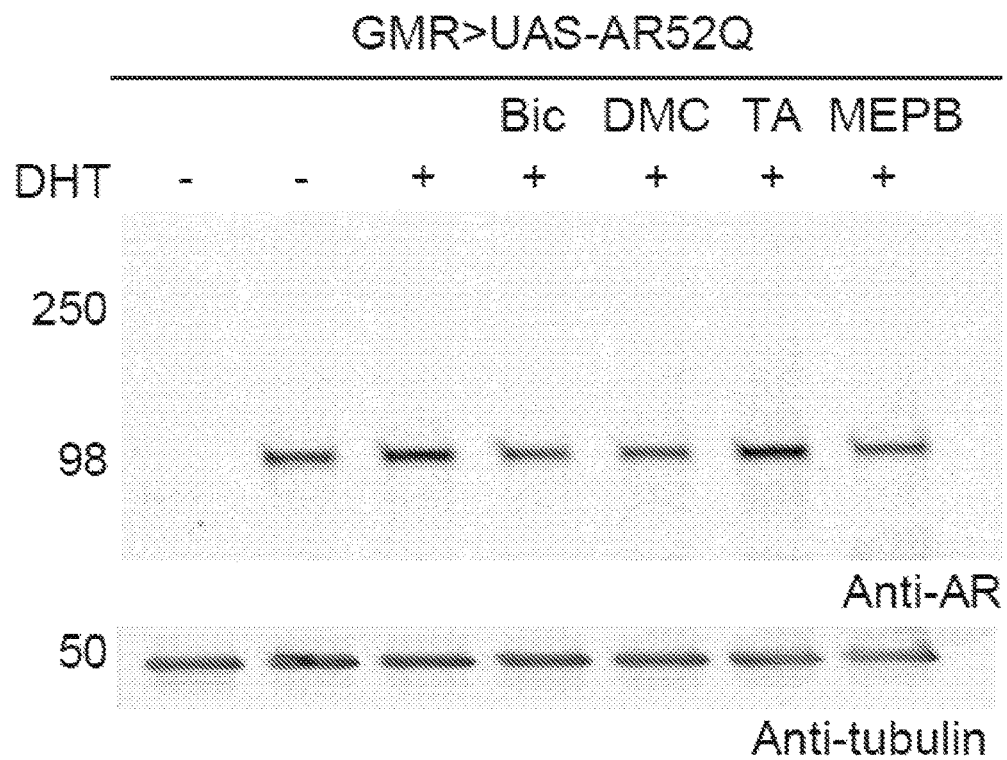
Figure 8C:
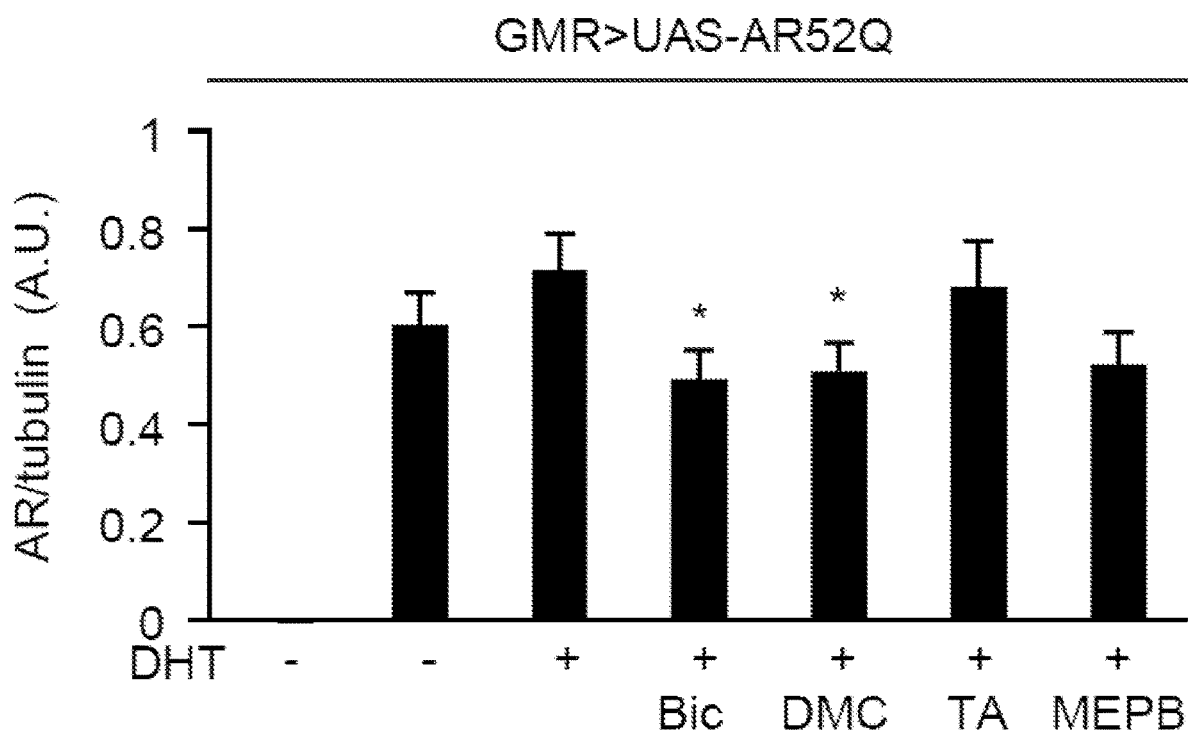
Figure 8D:
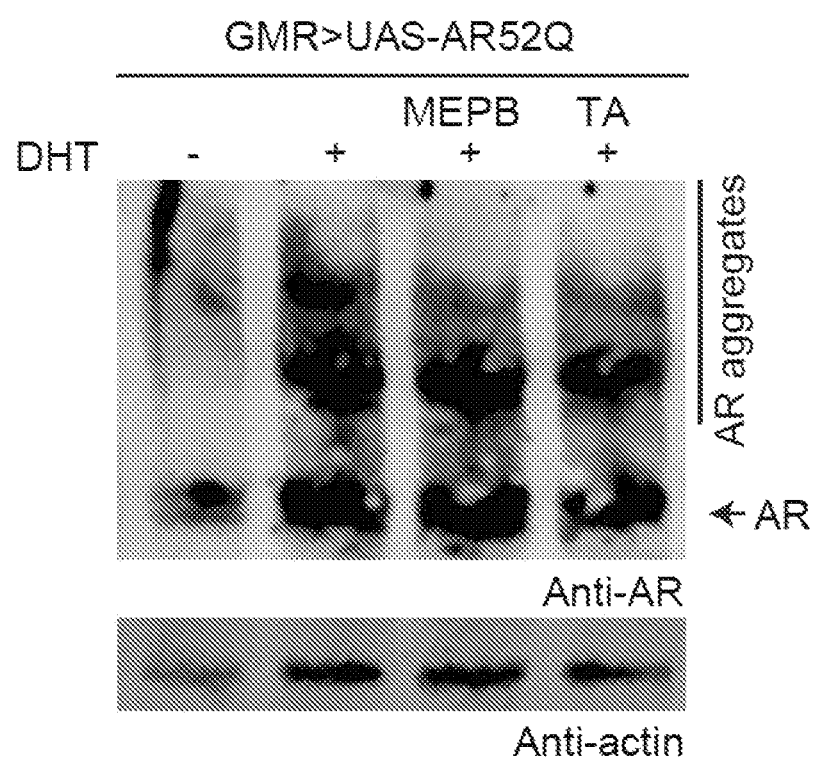
Figure 8E:
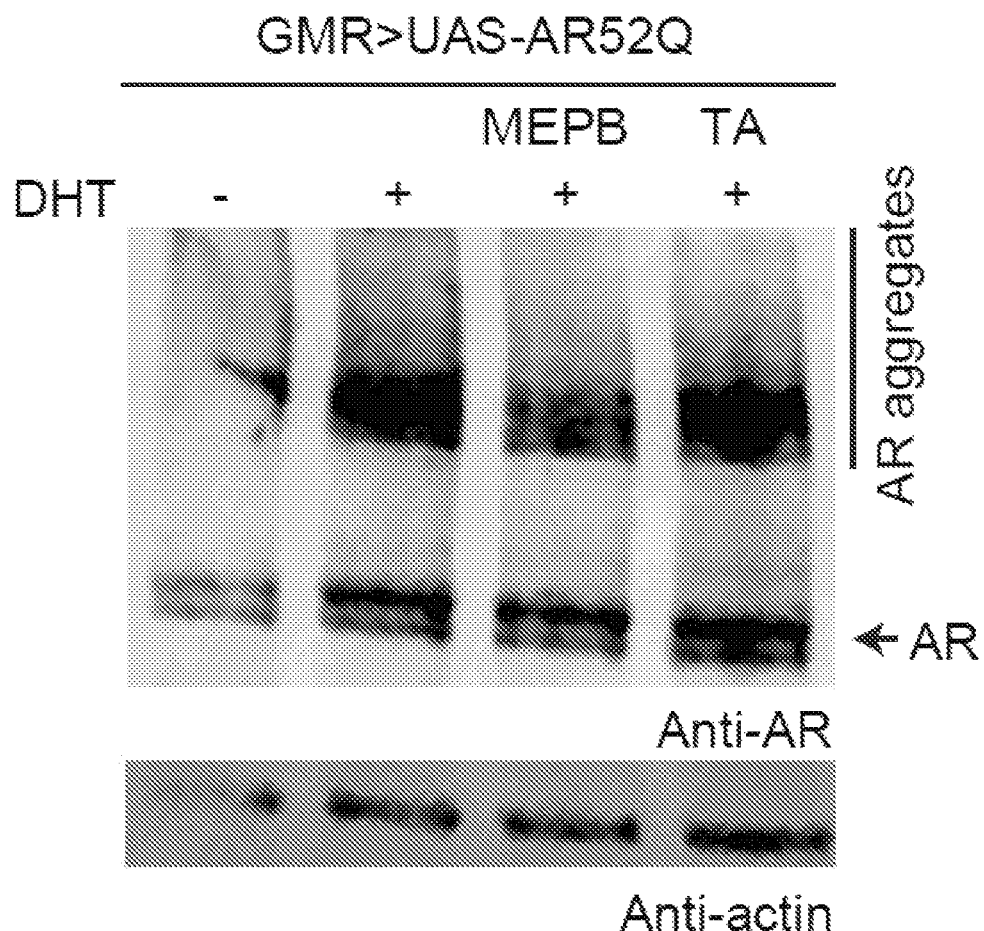

We compiled a panel of small-molecule compounds that were previously identified by in silico or in vitro screening to modulate coregulator binding to the AR AF2 domain by specifically binding to a proximal regulatory pocket termed the binding function-3 (BF3) domain[17-22]. Upon binding of such compounds to the BF3 domain, a conformational shift occurs in the AF2 domain that modulates the ability of coregulators bearing FXXLF and LXXLL motifs to bind the AF2 domain (FIG. 1A). To determine whether such compounds may be advantageous for SBMA therapy, we tested their ability to rescue DHT-induced lethality in flies expressing polyQ-expanded AR in pan-neuronal tissues (ELAV>UAS-AR52Q) or specifically in motor neurons (OK371>UAS-AR52Q) (FIGS. 7A-7F). TA and MEPB treatment significantly increased SBMA fly viability in a dose-dependent manner (FIGS. 1B-1C), similar to the known AR antagonist bicalutamide, whereas an AR-unrelated compound, ibuprofen, did not (FIGS. 7A-7F). Consistent with these results, both TA and MEPB significantly restored locomotor function in flies expressing polyQ-expanded AR in motor neurons (OK371>UAS-AR52Q), measured as increased displacement and velocity of walking in adult flies (FIGS. 1D-1F), to similar levels observed in flies expressing AR variants that modulate coregulator binding to the AF2 domain (OK371>UAS-AR52Q-K720A and OK371>UAS-AR66Q-E897K). Furthermore, both TA and MEPB restored DHT-dependent neuromuscular junction defects in SBMA larvae of OK371>UAS-AR52Q flies by reducing the prevalence of satellite boutons and preventing loss of neuromuscular junction branching (FIGS. 1G-1I). These results were corroborated in flies expressing polyQ-expanded AR in the eye (GMR>UAS-AR52Q), in which DHT-dependent degeneration was mitigated by TA and MEPB, similar to that of bicalutamide and dimethylcurcumin (FIG. 8A), without significantly reducing monomeric or aggregated forms of AR protein levels (FIGS. 8B-8E)

Figure 9A:
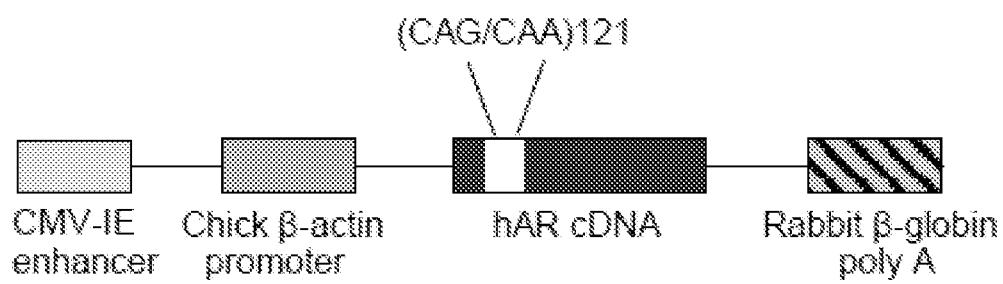
FIGS. 9A-9J demonstrate generation and characterization of a novel mouse model of SBMA.
Figure 9B:
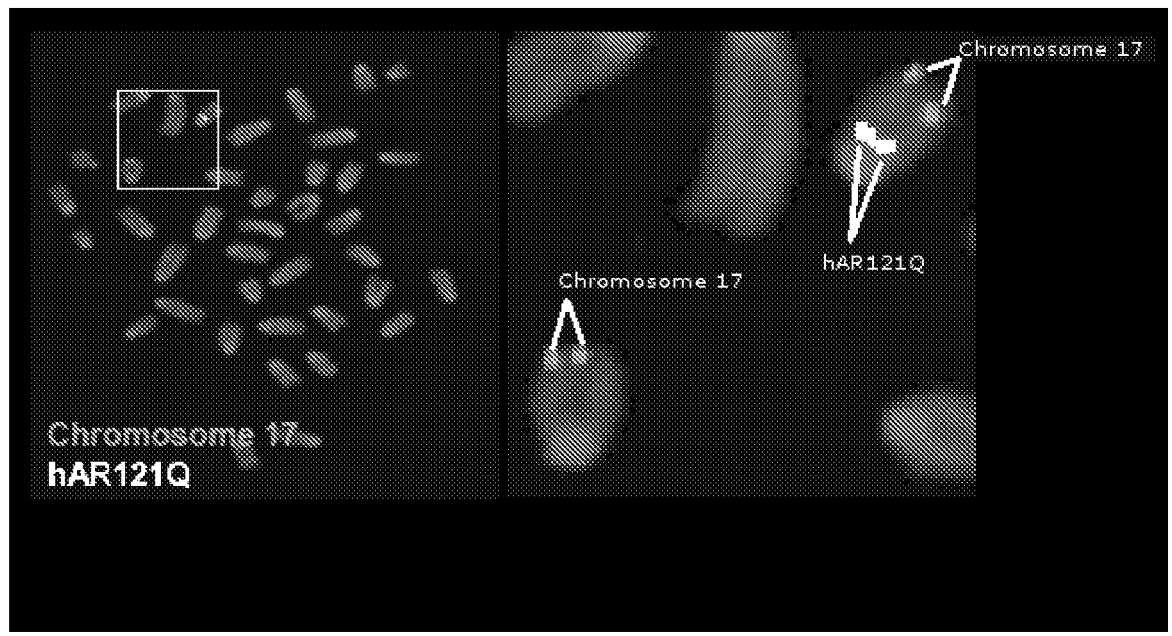
Figure 9C:
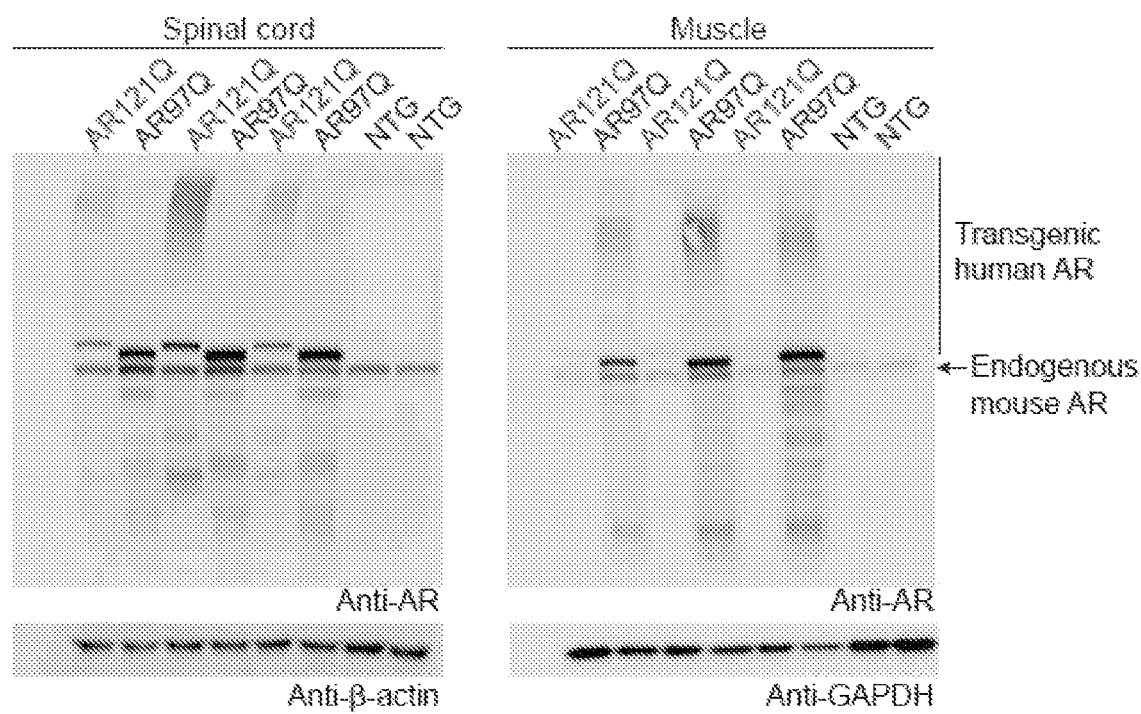
Figure 9D:
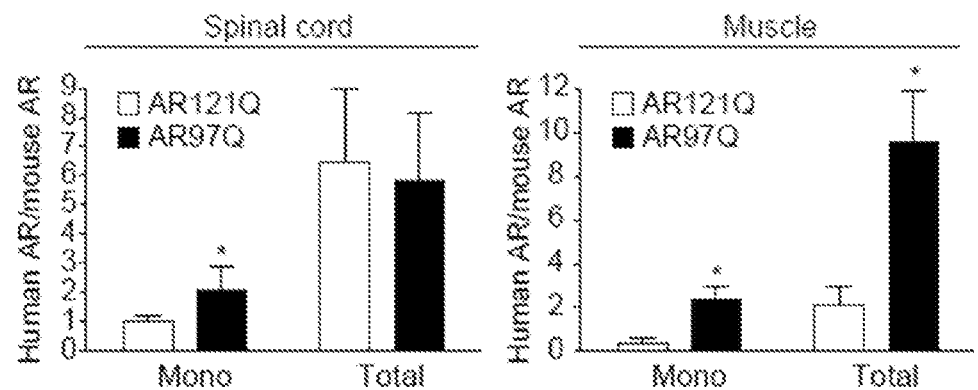
Figure 9E:
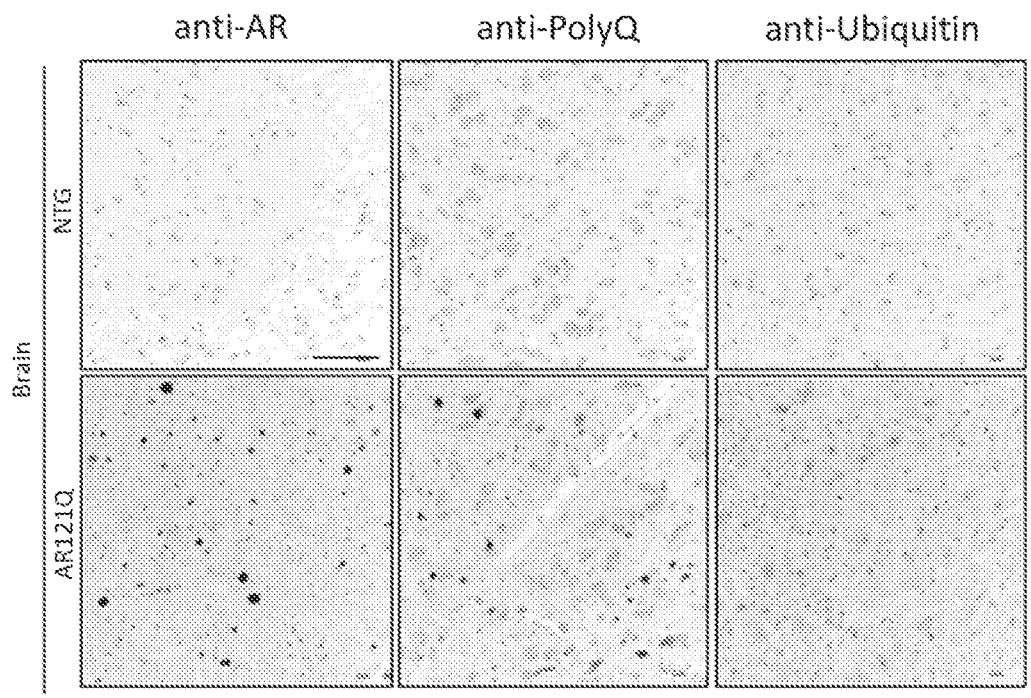
Figure 9F:
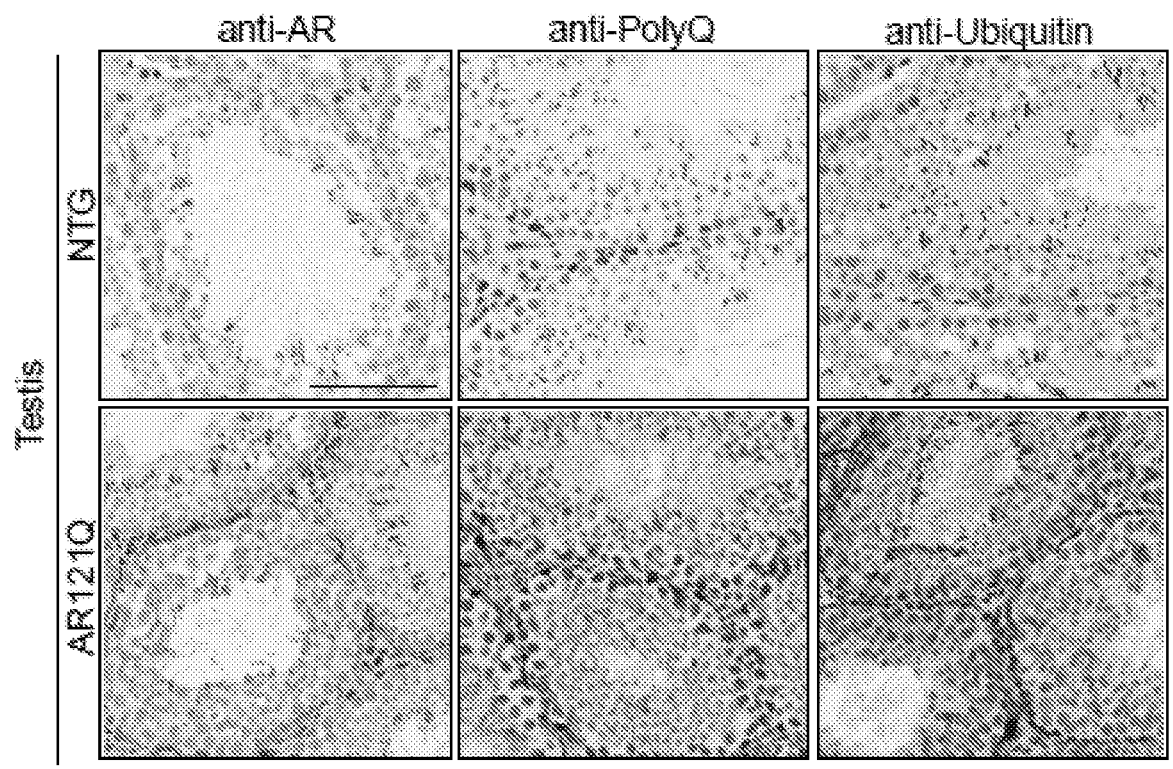
Figure 9G:
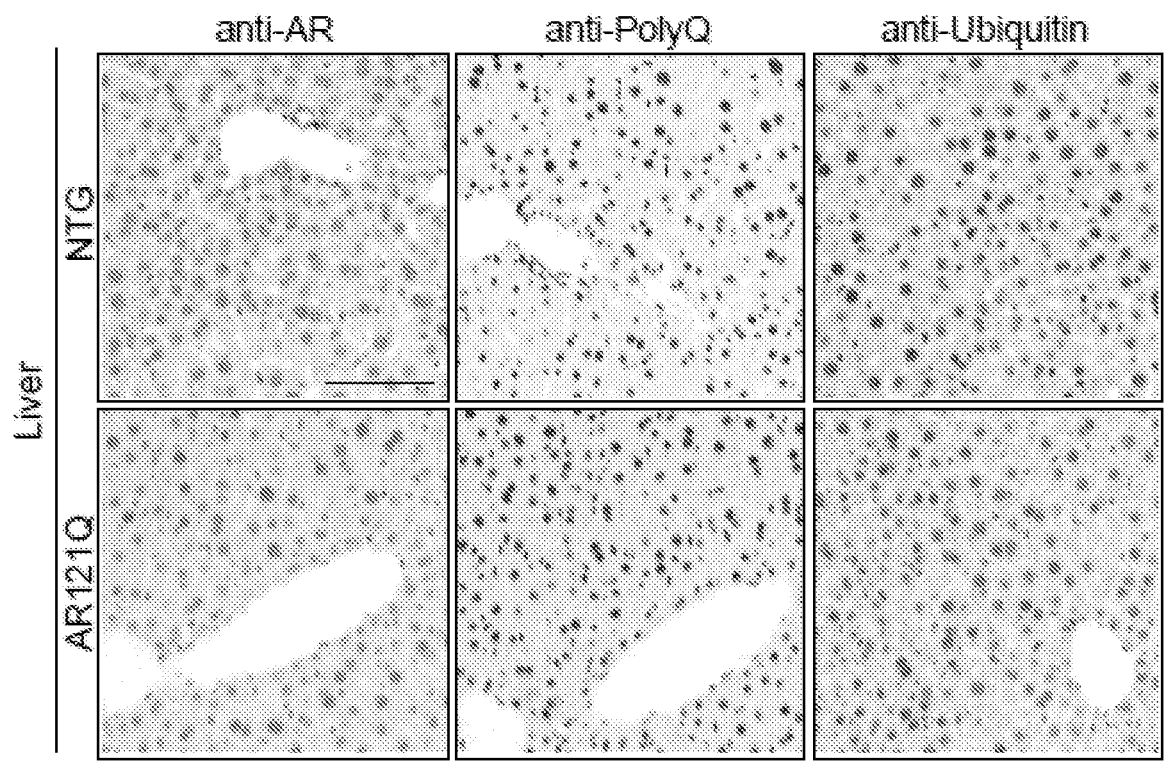

Transgenic Male Mice Carrying Full-Length Human AR with 121 CAG Repeats Recapitulate SBMA Symptoms and Pathology Previously reported mouse models of SBMA that exhibit disease-relevant phenotypes express the polyQ-AR transgene at levels several-to-many fold higher than endogenous AR. For example, the most frequently used mouse model of SBMA[12] expresses exogenous human AR at levels approximately three times higher than endogenous AR levels (FIG. 9C and FIG. 9D). Although these prior mouse models of SBMA have been a valuable resource to the research community, we were concerned about the possibility that high levels of mutant AR expression might mask the therapeutic potential of SARMs. Thus, to evaluate the efficacy of SARM therapy in a mammalian system, we developed an animal model that phenocopies the disease-relevant features of SBMA by expressing physiologically relevant levels of mutant AR. Founder SBMA mice were produced by pronuclear injection of human AR cDNA containing 121 CAG/CAA alternating repeats driven by the pCAGGS (CMV-IE enhancer+chick β-Actin) promoter (FIG. 9A and FIG. 9B). We identified one line that expressed the AR transgene in spinal cord and muscle at endogenous levels (FIG. 9C and FIG. 9D) and this line was chosen for further characterization.

Figure 2A:
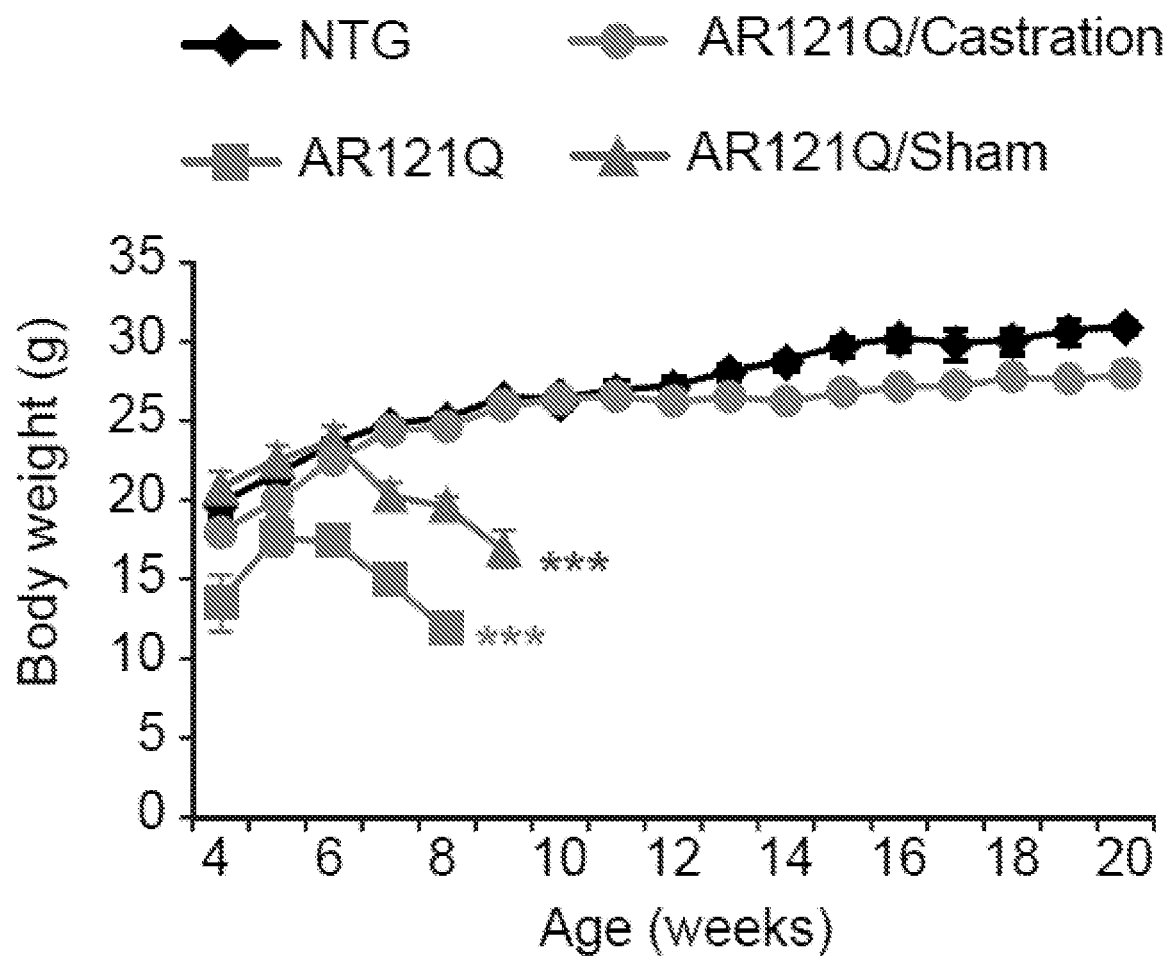
FIGS. 2A-2L depict AR121Q-expressing mice recapitulate SBMA symptoms and pathology.
Figure 2B:
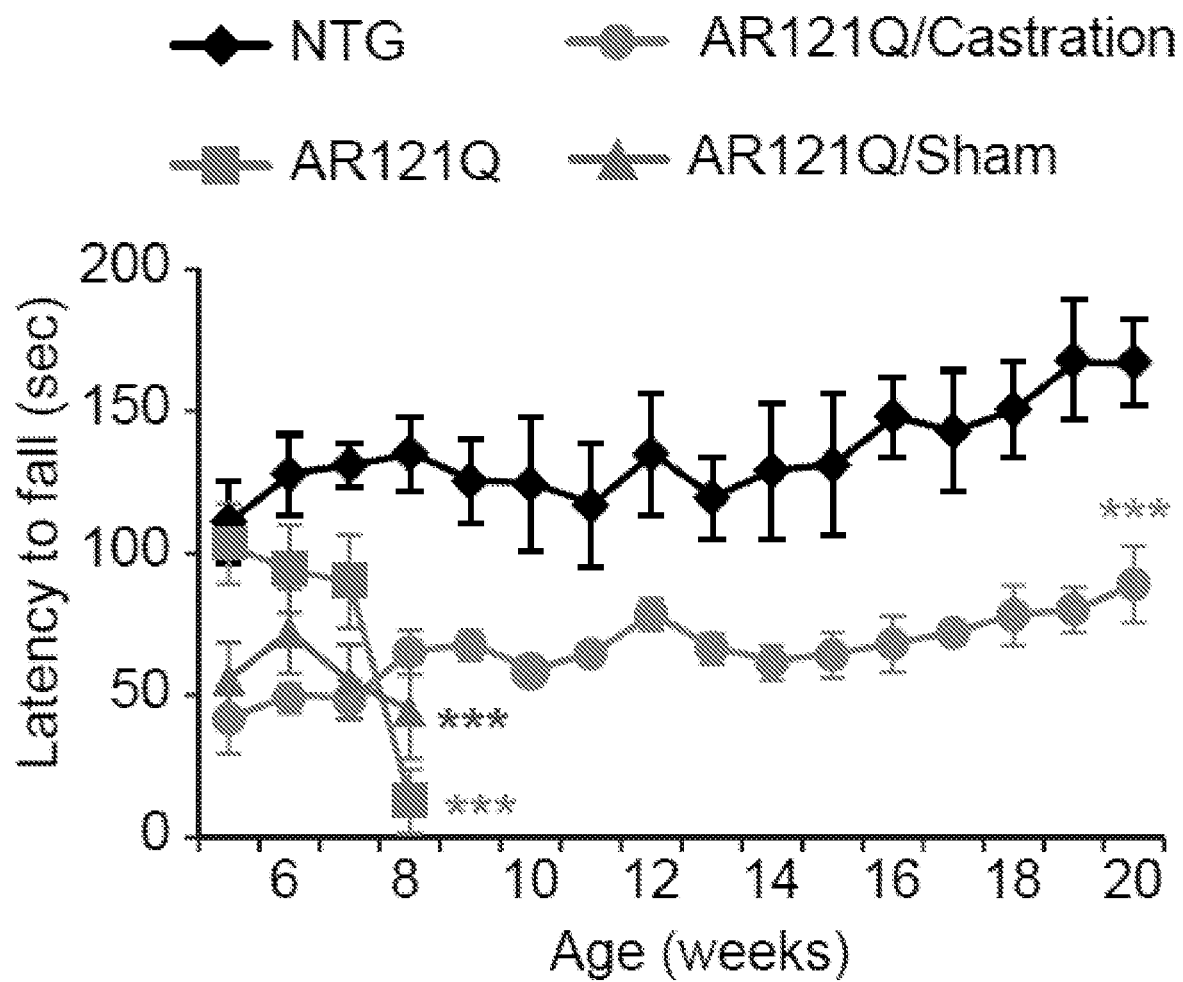
Figure 2C:
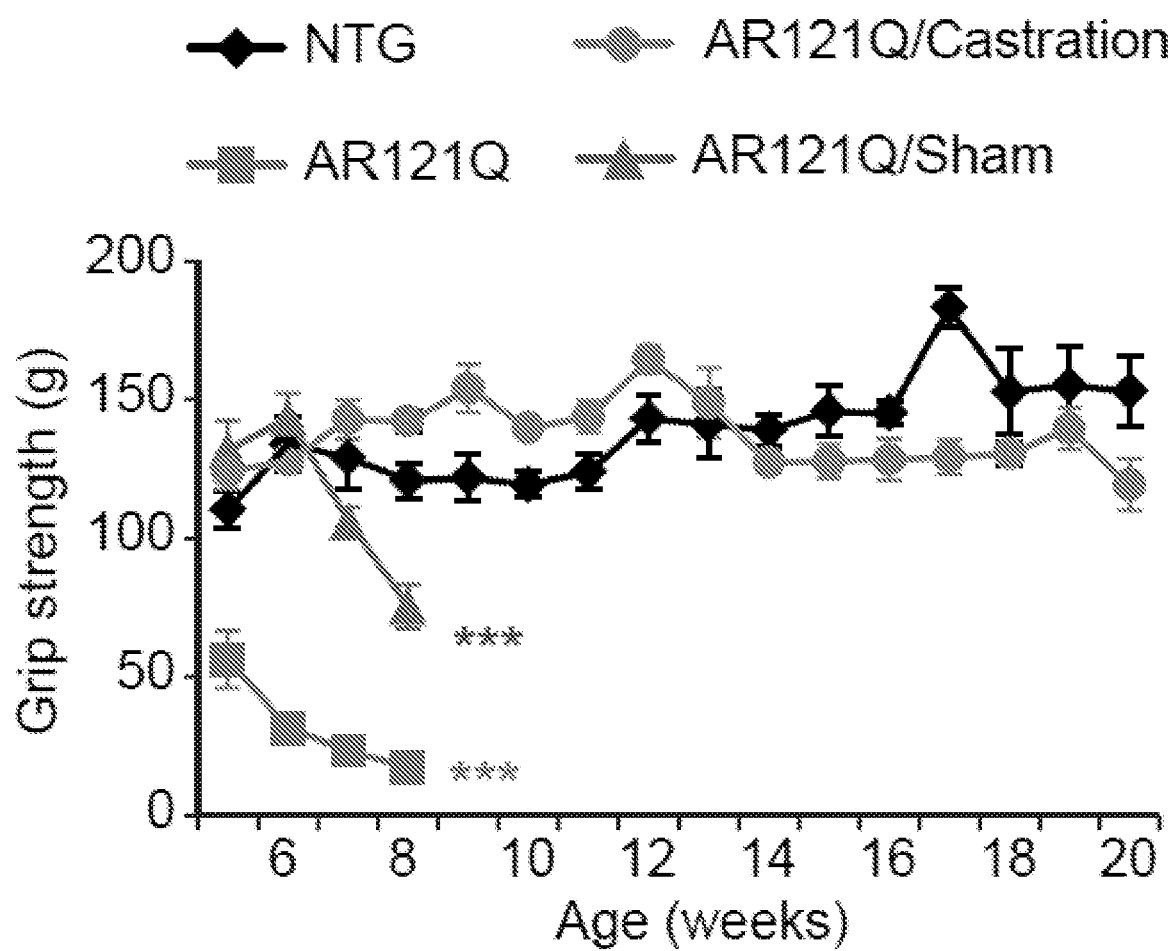
Figure 2D:
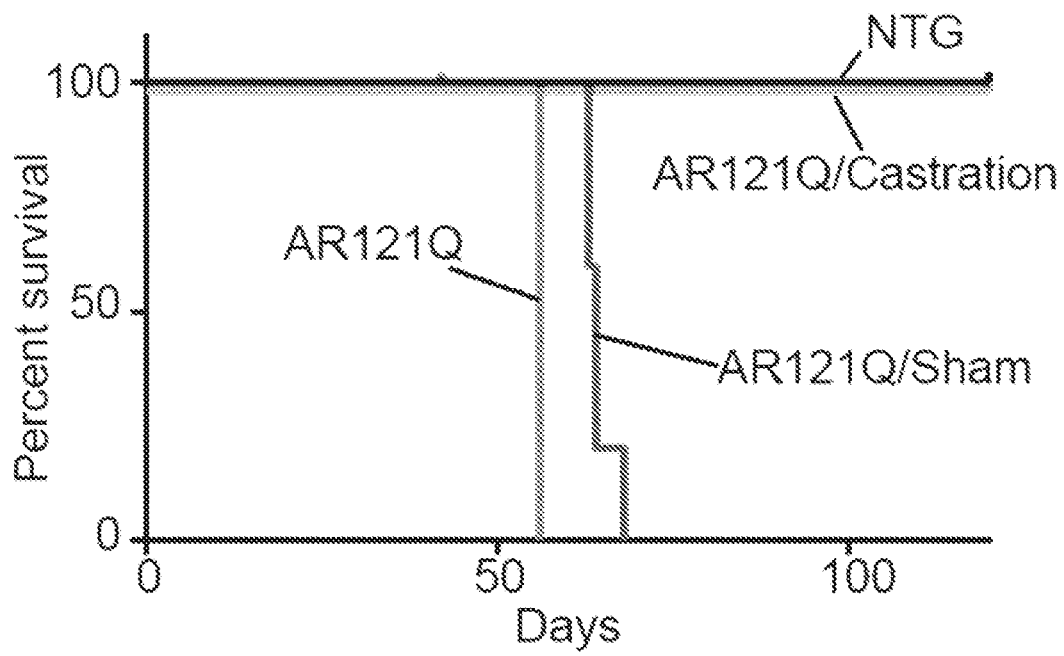
Figure 2E:
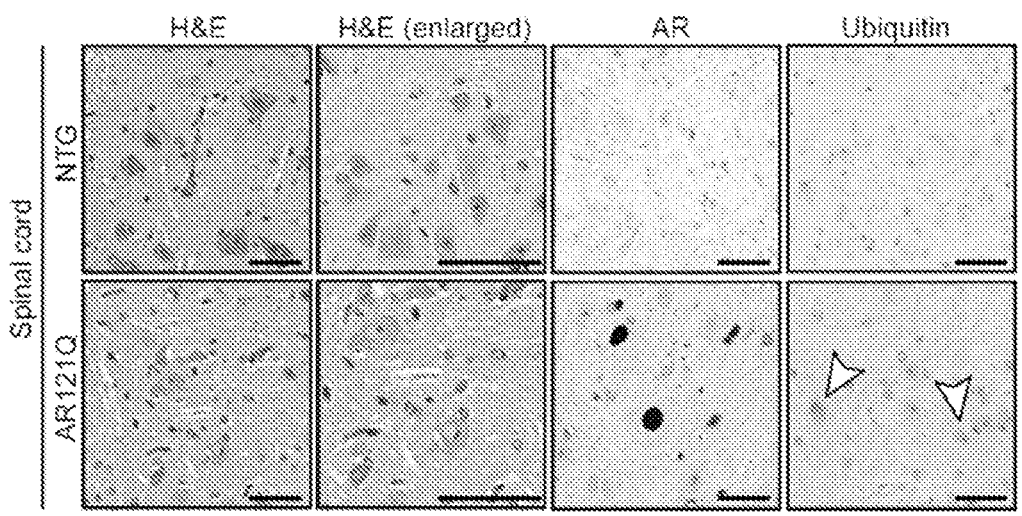
Figure 2F:
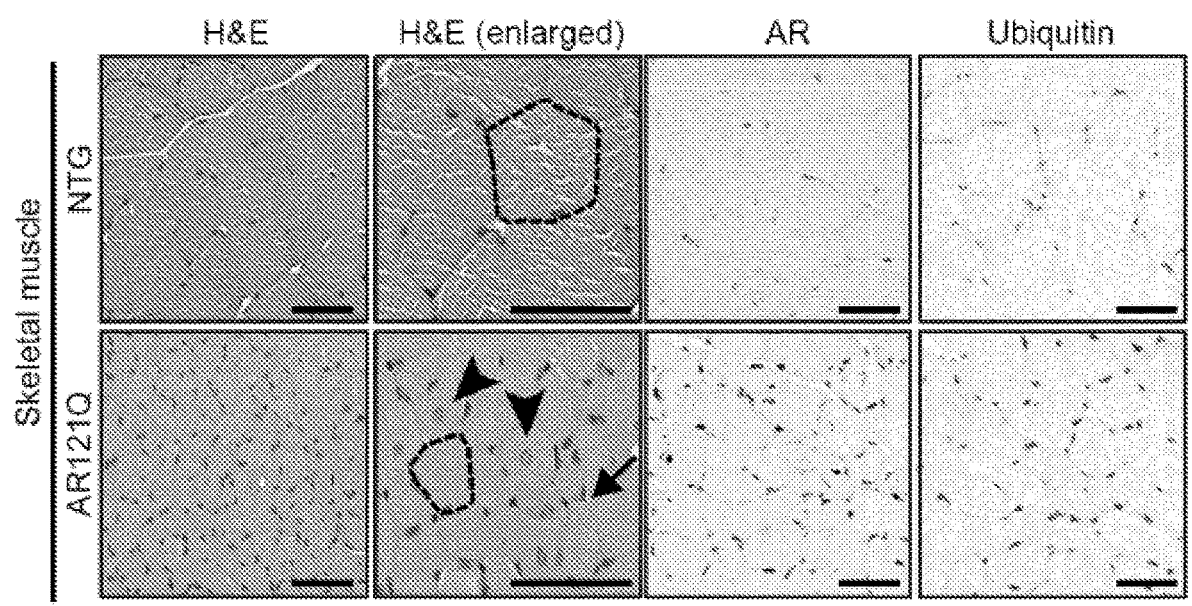
Figure 2G:
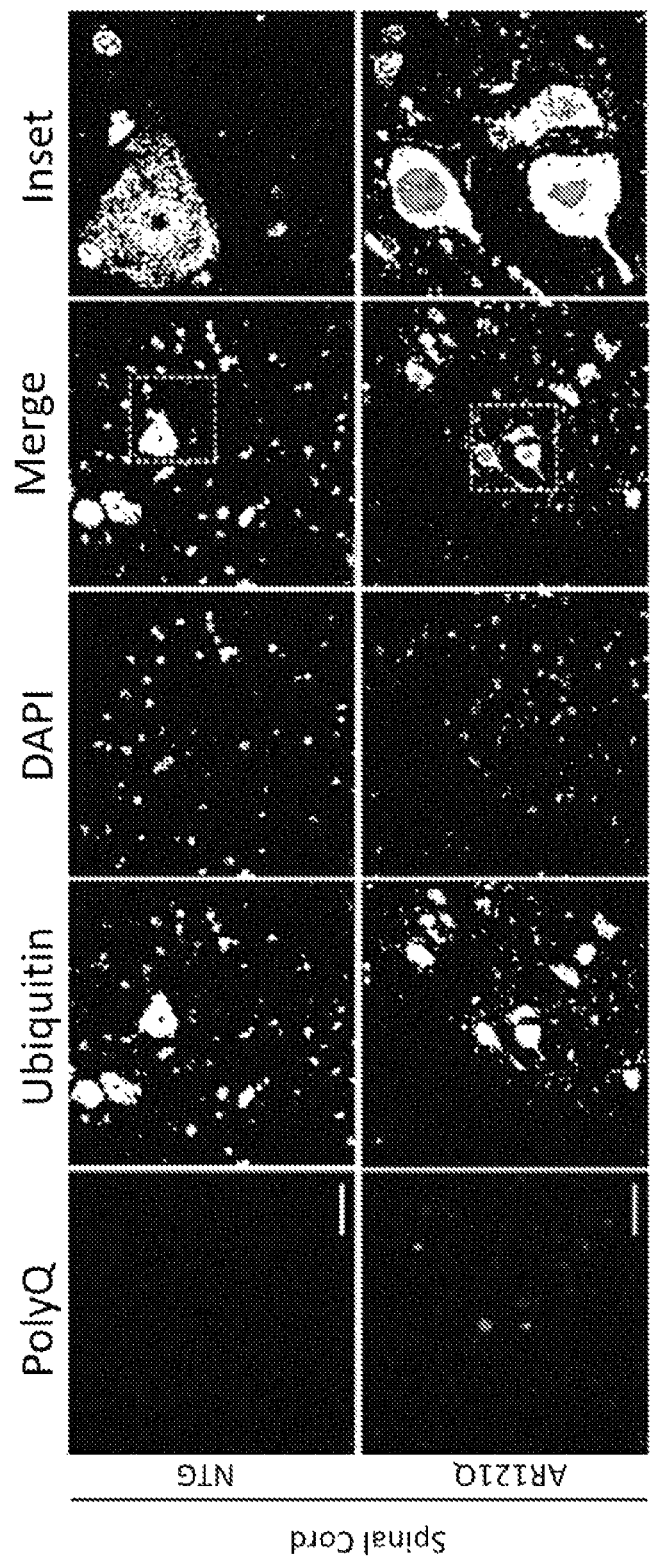
Figure 2H:
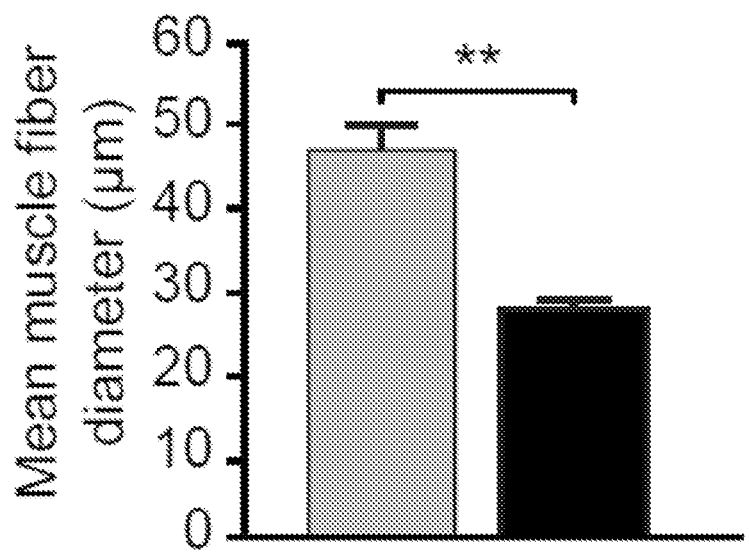
Figure 2I:
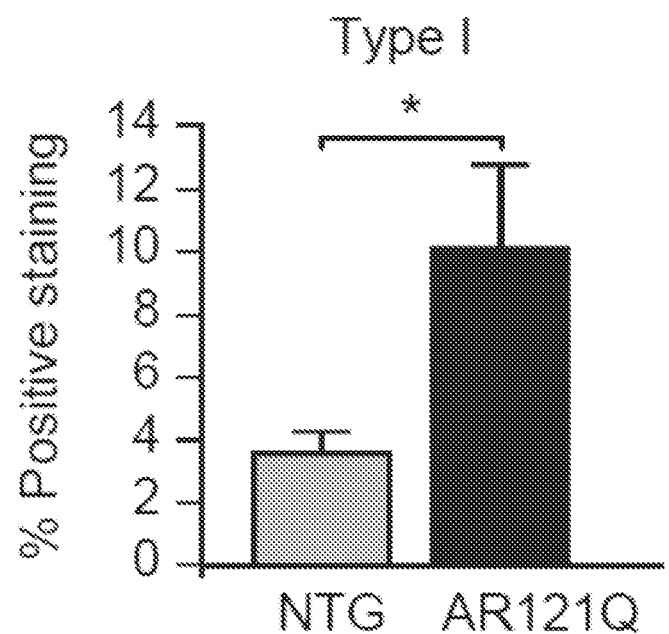
Figure 2J:
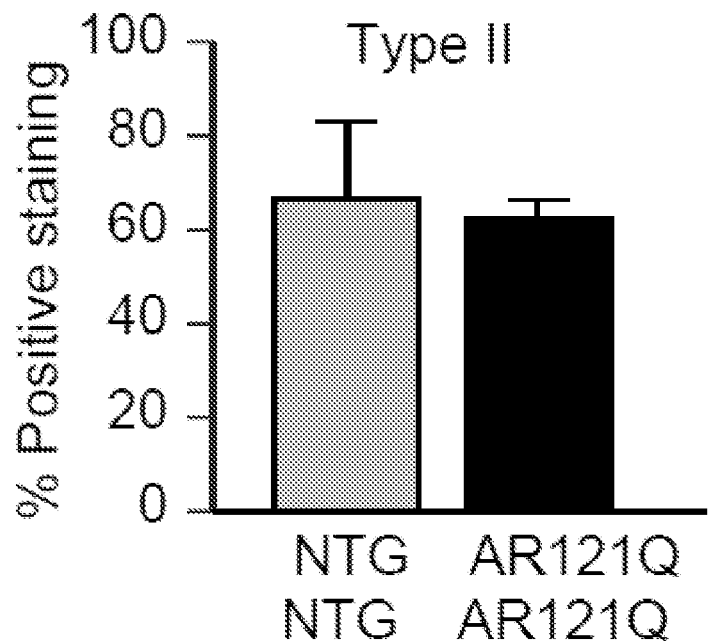
Figure 2K:
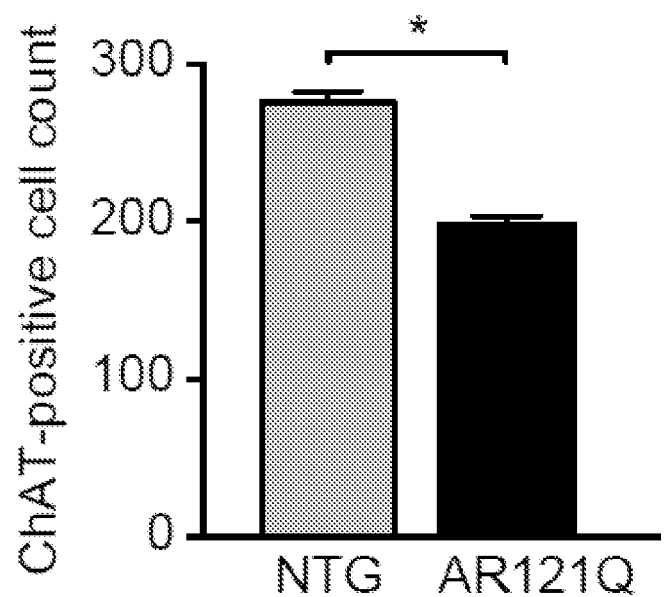
Figure 2L:
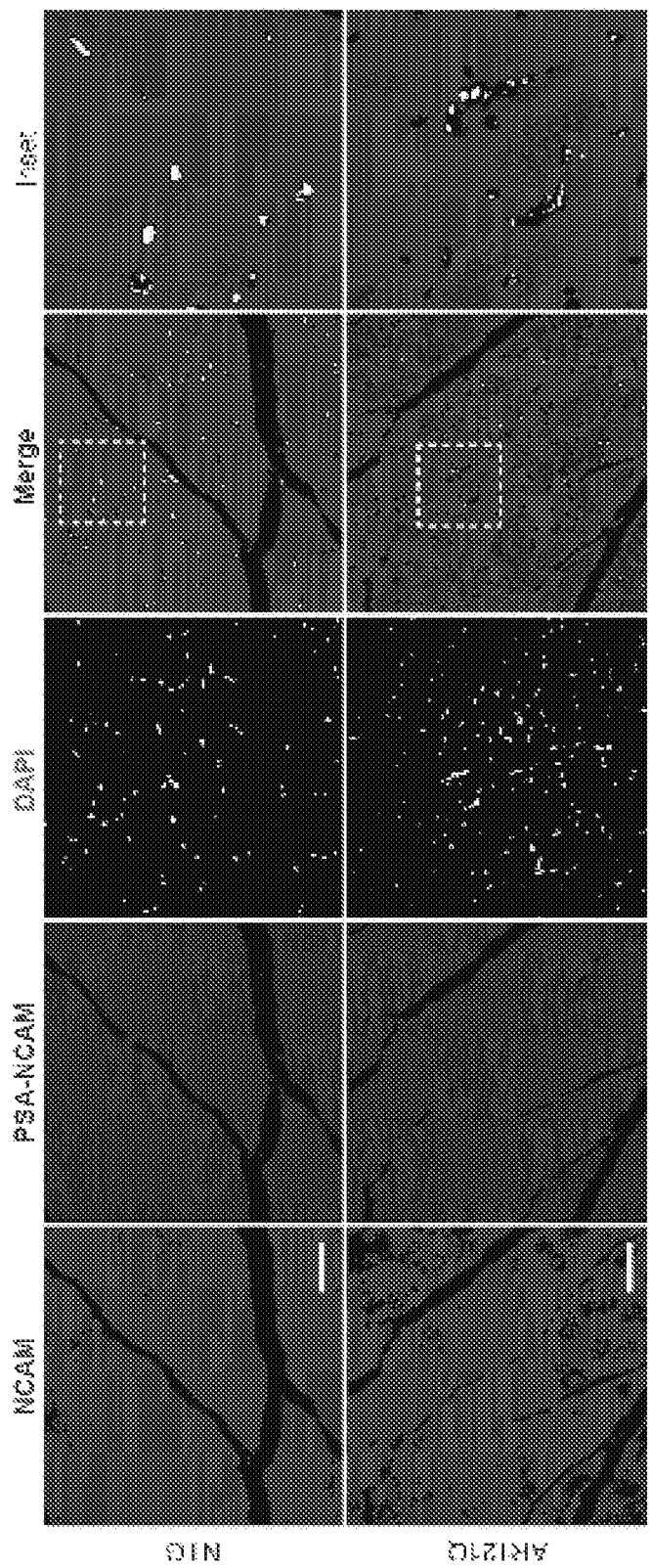
Figure 9H:
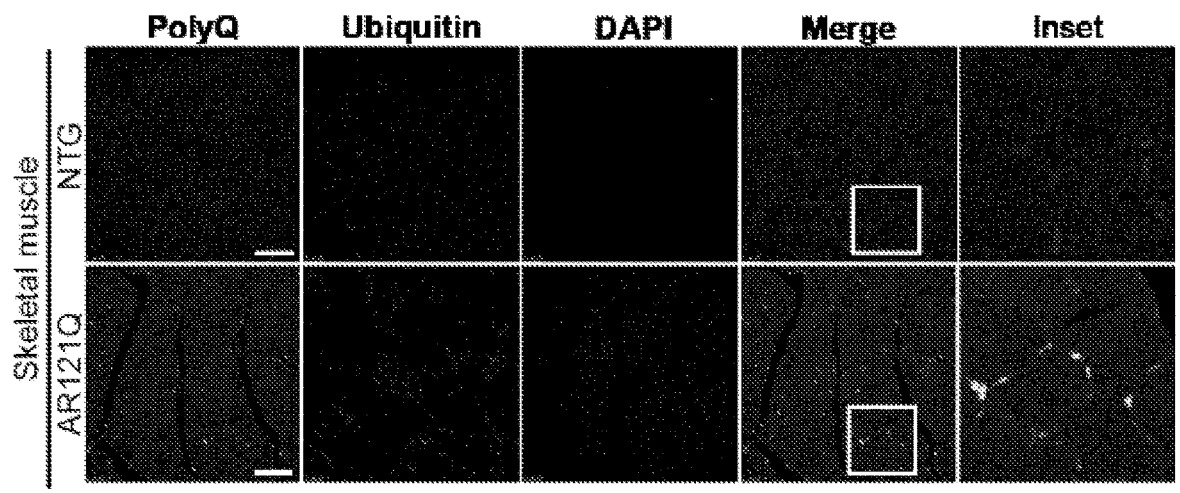
Figure 9I:
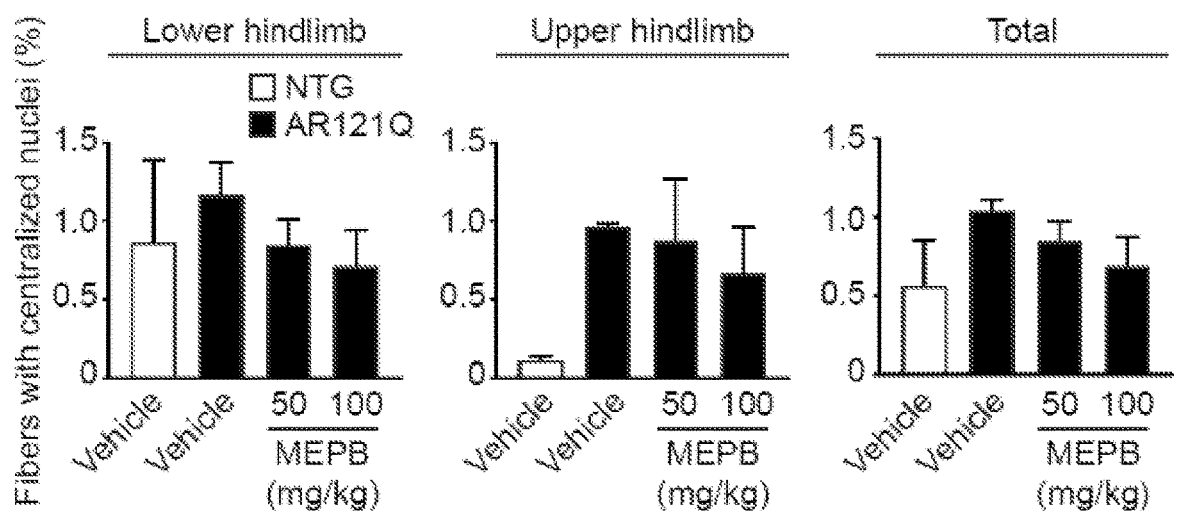

Male AR121Q mice demonstrated rapid androgen-dependent declines in body weight, rotarod activity, grip strength, and survival (FIGS. 2A-2D) when compared with nontransgenic FVB/NJ (NTG) control littermates. Immunohistochemistry using anti-AR, anti-polyQ, and anti-ubiquitin revealed the presence of aggregates in the brain, spinal cord, and skeletal muscle but not in the testis or liver of AR121Q mice (FIGS. 2E-2F and FIGS. 9E-9G). These ubiquitin-positive nuclear inclusions also colocalized with polyQ in the spinal cord and skeletal muscle (FIG. 2G and FIG. 9H). Muscle fiber type switching from glycolytic type II fibers to oxidative type I fibers has recently been characterized as a pathological hallmark of muscle atrophy in mice and patients with SBMA[23]. Consistent with this characterization, AR121Q mice displayed a marked presence of atrophied skeletal muscle fibers and switching of muscle fibers from glycolytic type II to oxidative type I (FIG. 2H-2I). Furthermore, we observed fewer choline acetyltransferase (ChAT)—positive motor neurons in the anterior horn of the thoracic spinal cord in AR121Q mice compared to NTG controls (FIG. 2J-2K). Immunofluorescence with antibodies against neuronal cell adhesion molecule (NCAM) and its polysialic acid form (PSA-NCAM), a protein known to be upregulated during muscle reinnervation[24-26], revealed marked sarcoplasmic staining of muscle fibers in AR121Q mice but not in NTG controls (FIG. 2L), demonstrating ongoing denervation/reinnervation in AR121Q mice. AR121Q mice also exhibited markedly decreased hindlimb muscle mass and increased angular fibers (data not shown). Although centralized nuclei were present in some muscle fibers of AR121Q mice (FIG. 2F), quantification revealed that both AR121Q and NTG mice had fewer than 3% of fibers with centralized nuclei, with no statistically significant difference between them (FIG. 9I). Together, these data suggest that AR121Q mice exhibit primarily neurogenic rather than myogenic atrophy and weakness.

Figure 9J:
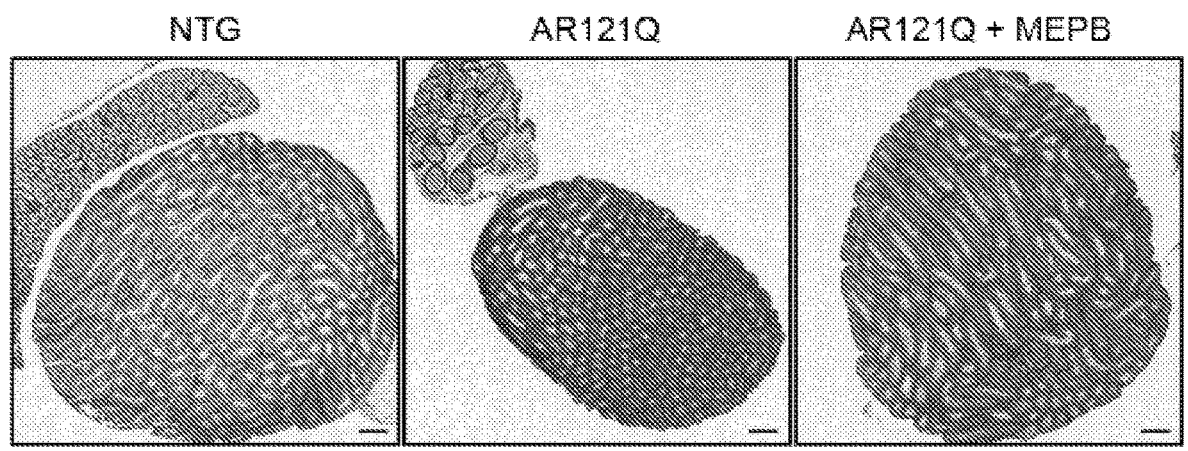

Finally, we also observed testicular atrophy in the SBMA mice, similar to that described for an AR113Q knock-in mouse model of SBMA (FIG. 9J)[27]. This feature is consistent with the partial androgen insensitivity experienced by patients with SBMA, which manifests as testicular atrophy, gynecomastia, and reduction in secondary sexual characteristics, and can impair QOL. The partial androgen insensitivity experienced by SBMA patients is not reversed and may be aggravated by conventional, non-selective androgen ablation.

Figure 3A:
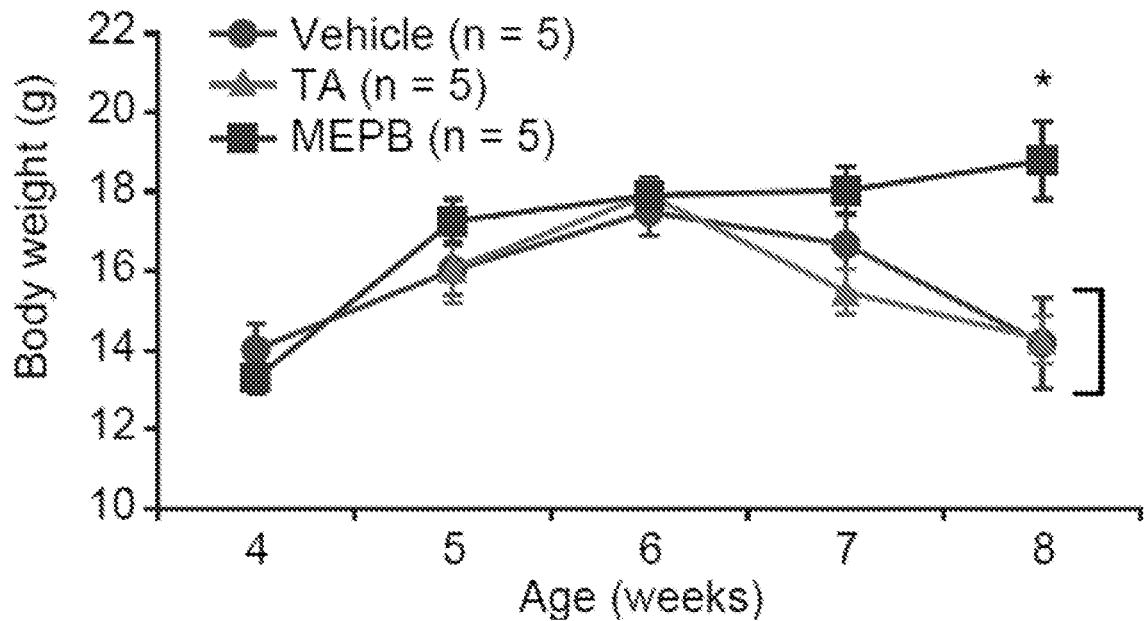
FIGS. 3A-3I demonstrate MEPB improves phenotypic outcomes and pathologic degeneration in a pilot preclinical trial in SBMA mice.
Figure 3B:
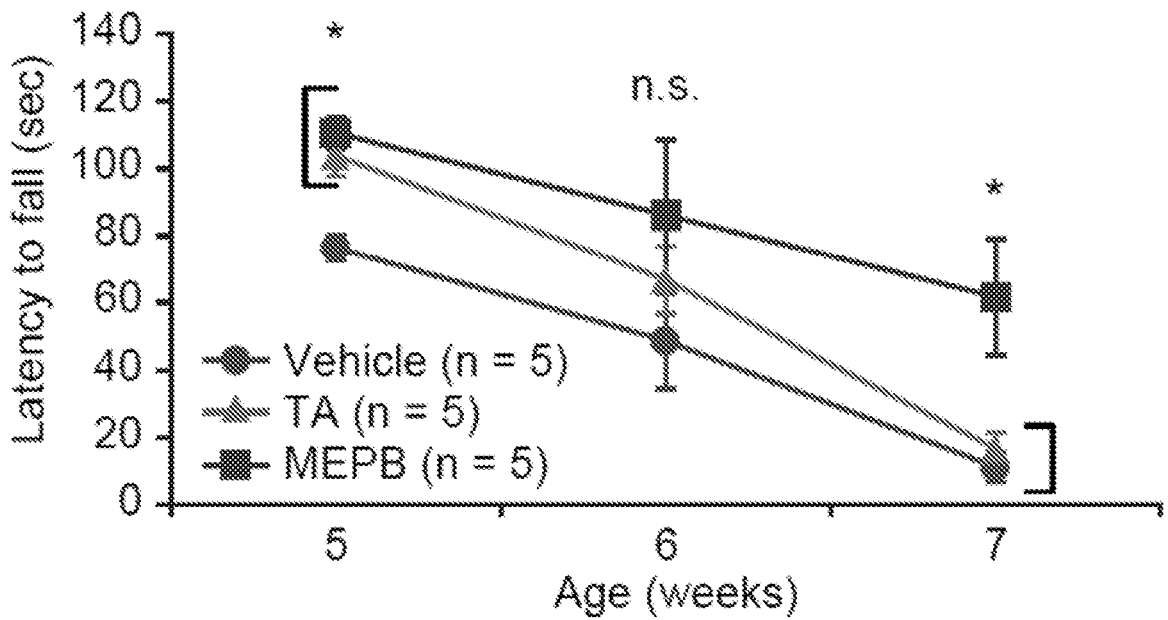
Figure 3C:
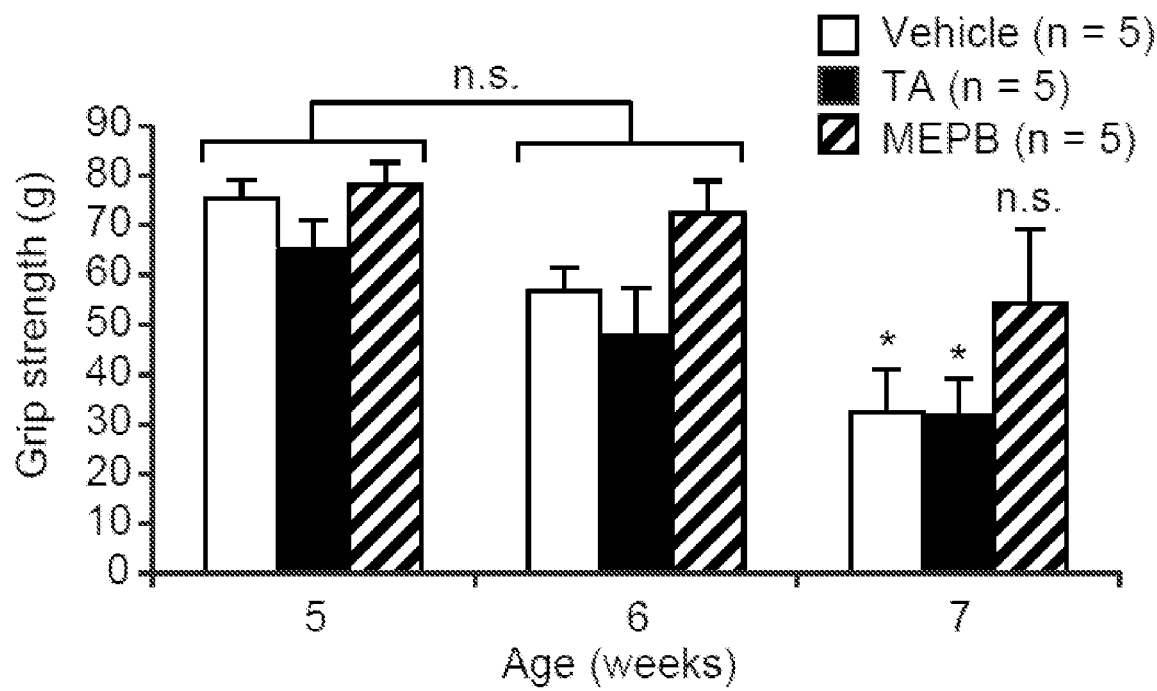
Figure 3D:
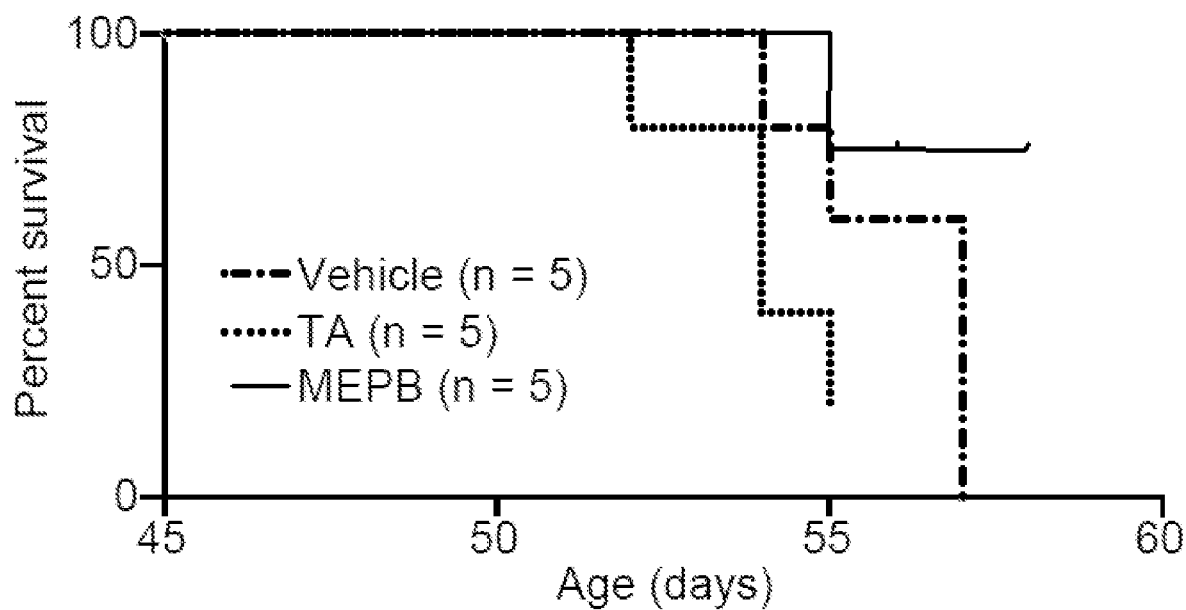
Figure 3E:
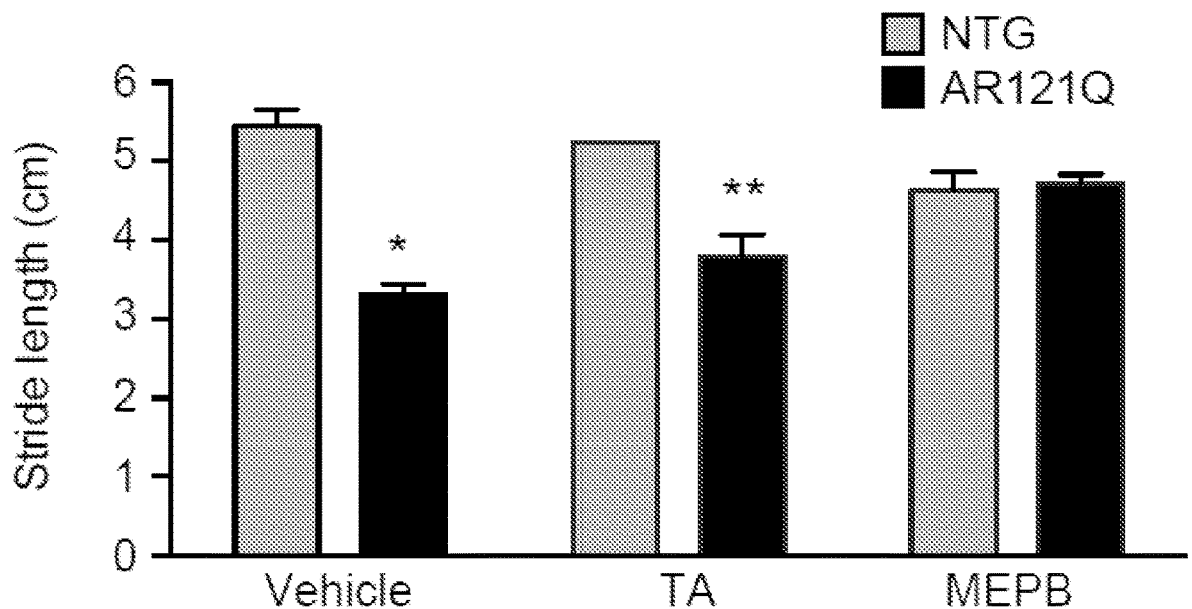
Figure 3F:
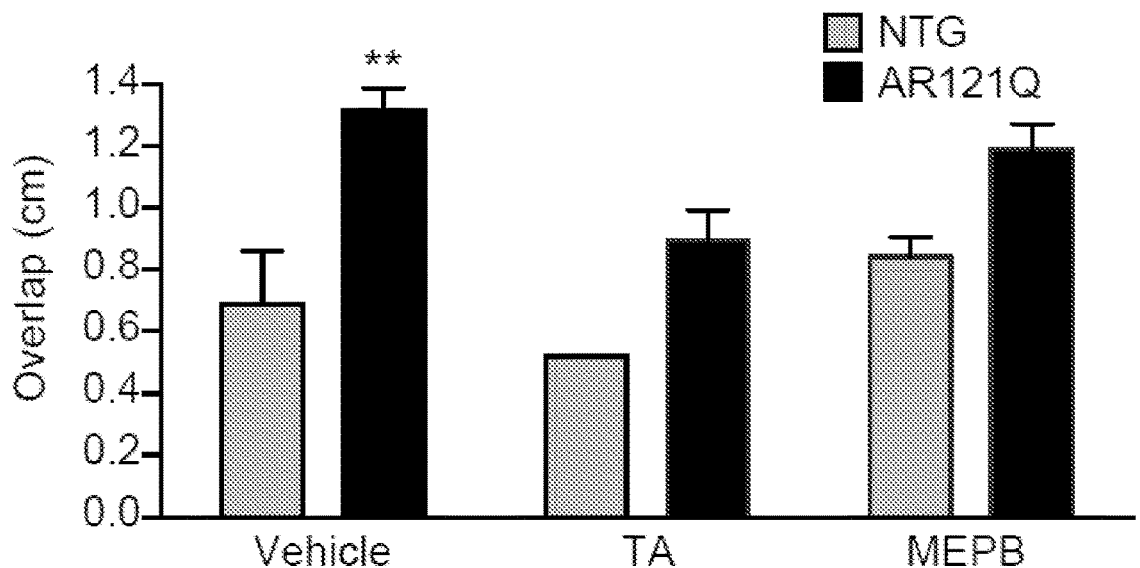
Figure 3G:
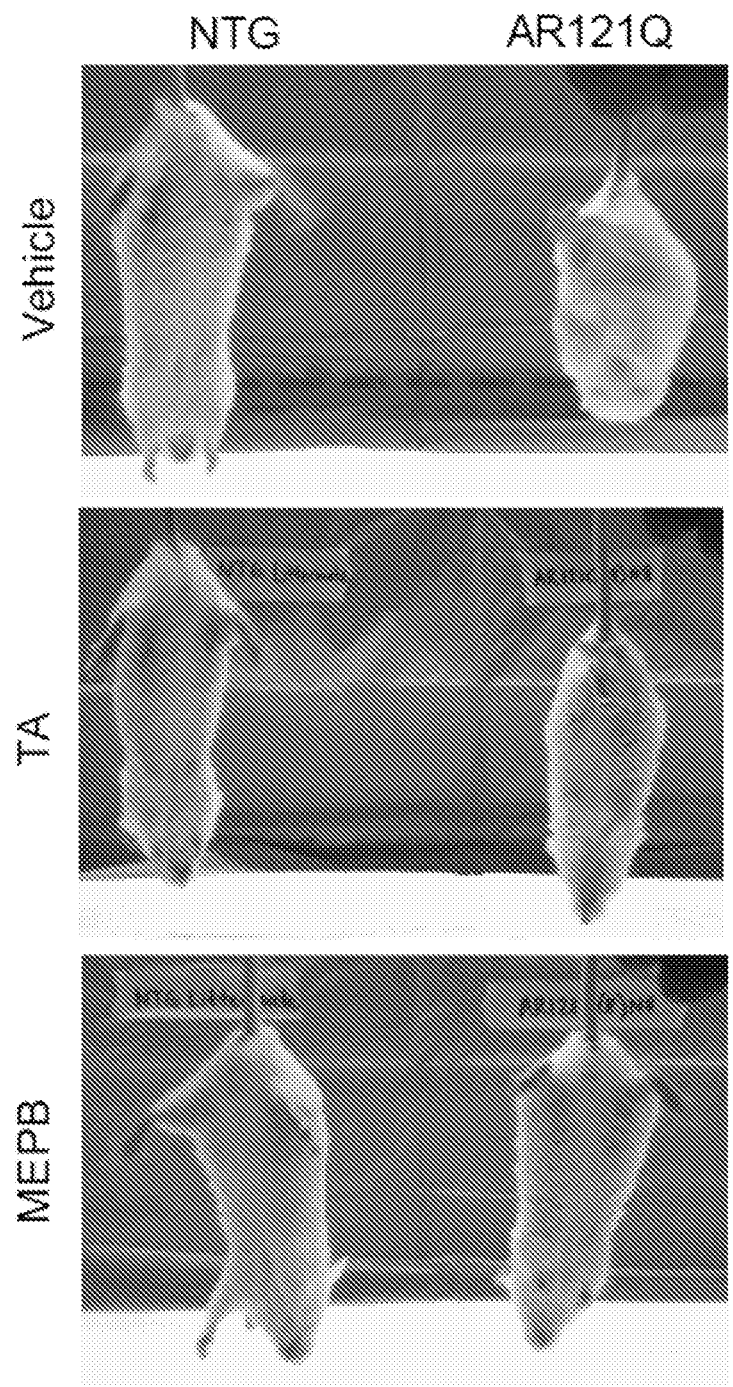
Figure 3H:
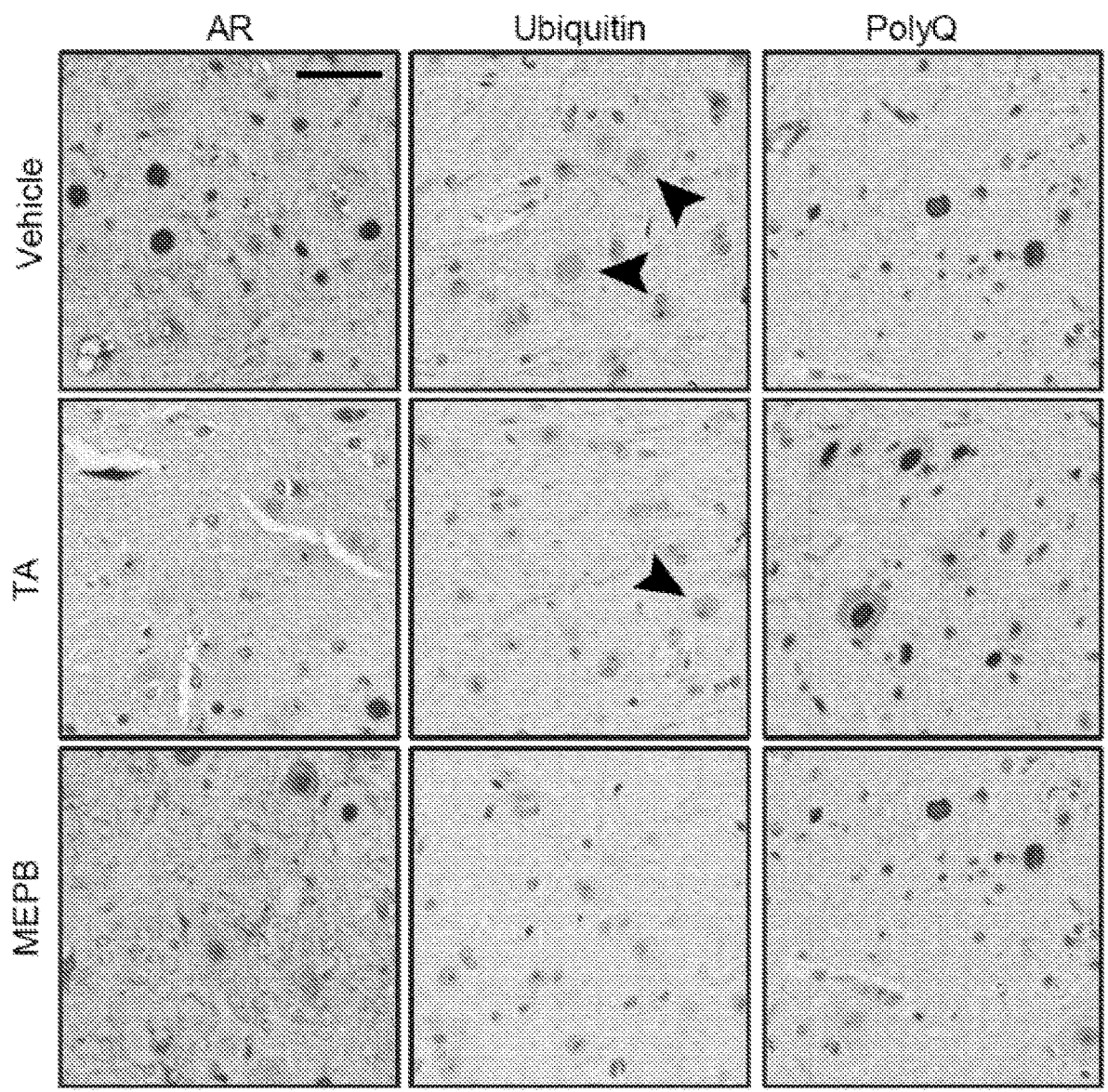
Figure 3I:
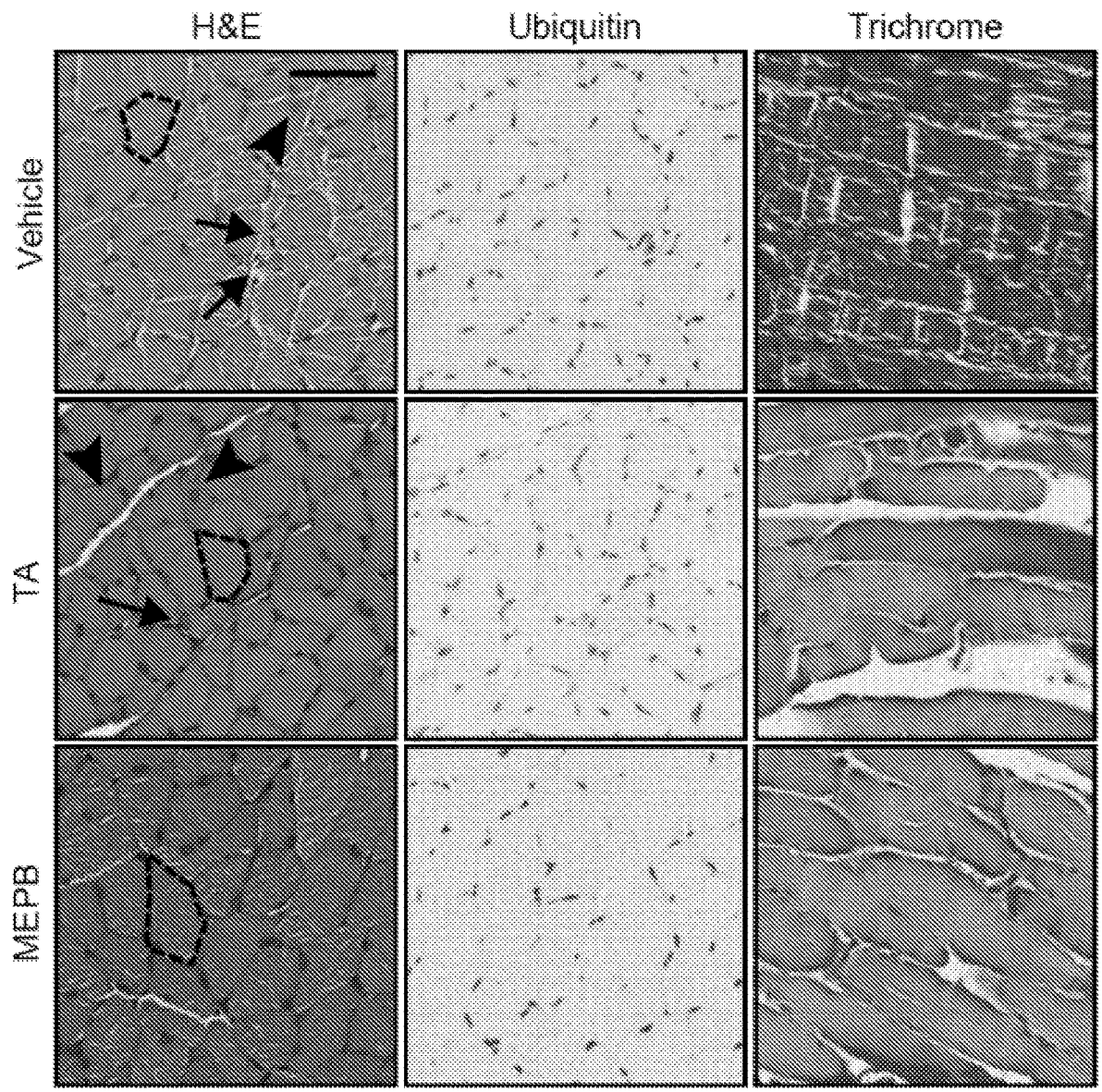
Figure 10A:
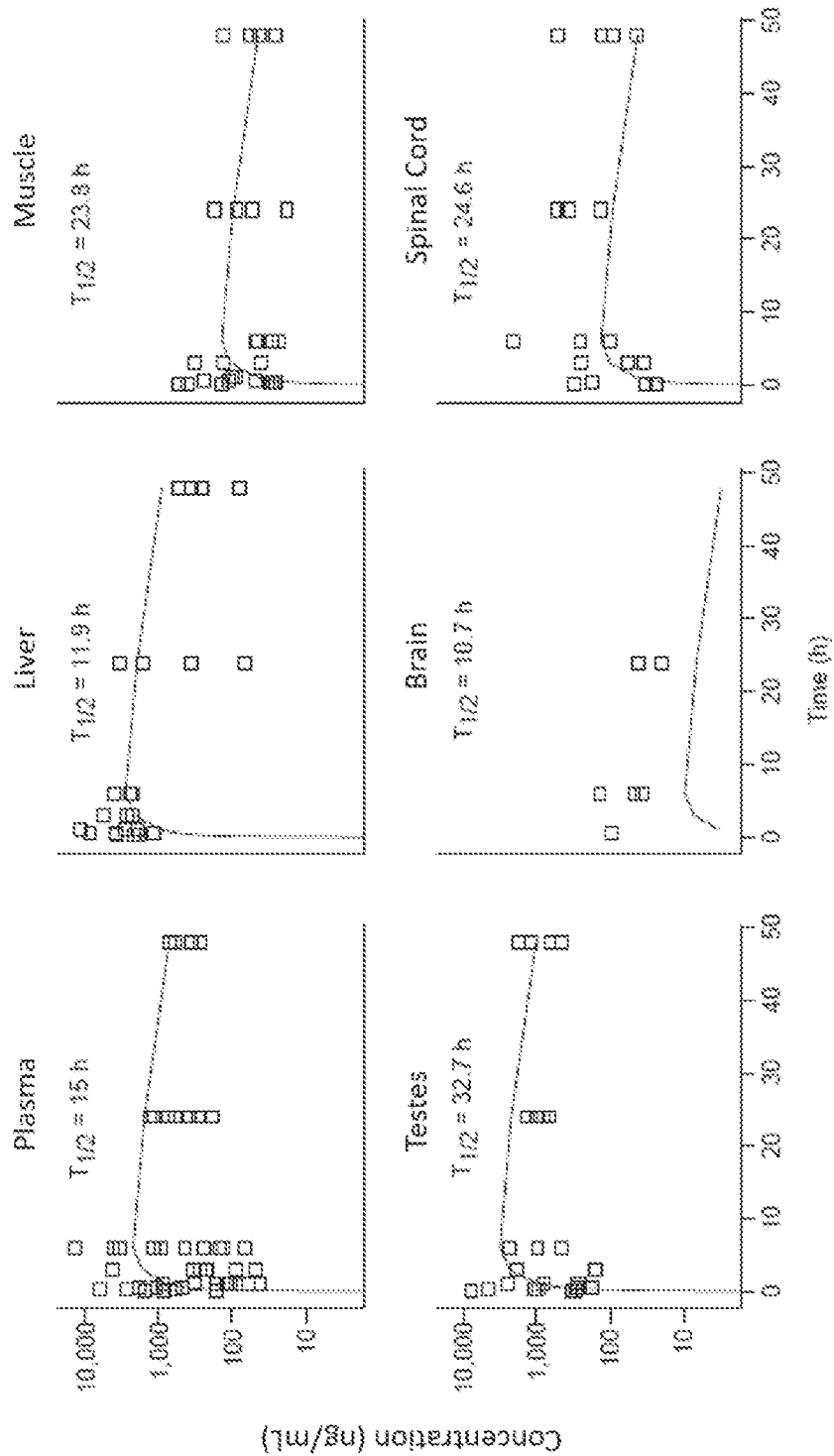
FIG. 10A and FIG. 10B demonstrate pharmacokinetics of MEPB and TA.
Figure 10B:
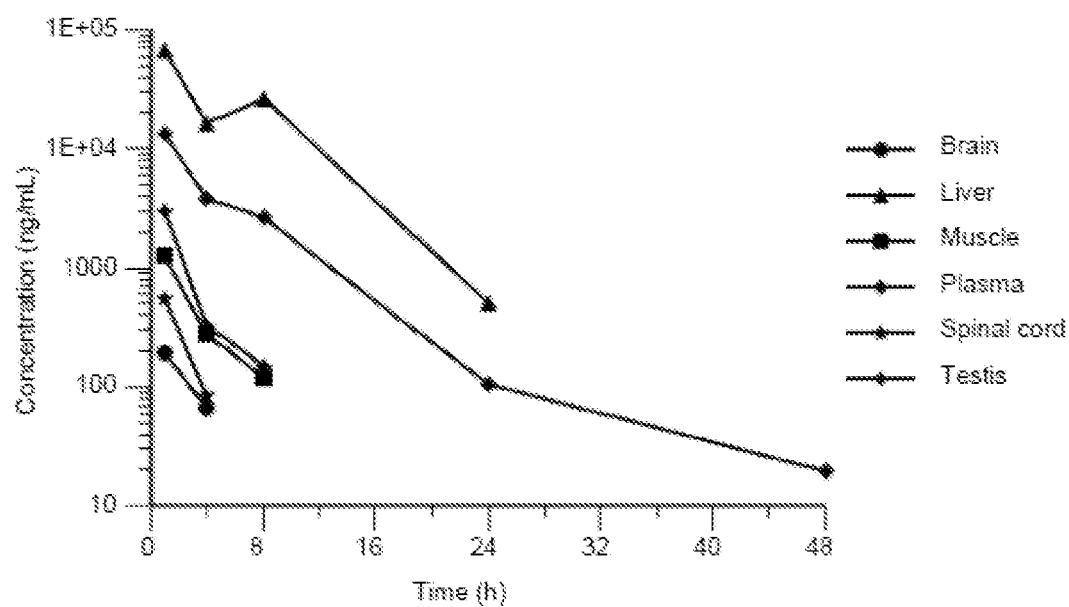

AF2 Modulation Improves Neurodegenerative Outcomes in a Pilot Study in SBMA Mice To ascertain the potential efficacy of AF2 modulation in the SBMA mice, we performed a preclinical pilot assessment of the effects of AF2 modulation on SBMA-associated degeneration in a small cohort of mice. Male SBMA mice were injected intraperitoneally (50 mg/kg body weight, three times per week) with TA, MEPB, or vehicle (1% DMSO in corn oil) from 3 to 8 weeks of age. MEPB treatment significantly improved body weight, rotarod activity, and grip strength (FIGS. 3A-3C), despite no significant change in survival (FIG. 3D), and improved gait and hindlimb clasping (FIGS. 3E-3G). In addition, the pathologic appearance of skeletal muscle and spinal cord degeneration was qualitatively recovered by MEPB treatment (FIGS. 3H-3I). TA treatment did not significantly alter any measurements of SBMA-associated degeneration (FIGS. 3A-3I), suggesting that MEPB provides superior therapeutic potential in SBMA mice. Indeed, pharmacokinetic analysis of TA and MEPB in NTG mice revealed marked penetration and duration of MEPB but not TA in muscle, spinal cord, and testes (FIG. 10A and FIG. 10B, Table 2), indicating sufficient bioavailability of MEPB in SBMA-affected tissues, but poor bioavailability of TA in SBMA mice. For this reason, MEPB was selected for subsequent proof of concept testing of the therapeutic potential of AF2 modulation in SBMA mice.

TABLE 2

Maximum concentration ($C_{max}$), time of Cmax ($T_{max}$), concentration at the last observed time point ($C_{last}$), and time of Clast ($T_{last}$) of TA in plasma, liver, muscle, testes, brain, and spinal cord following a single intraperitoneal injection of 50 mg/kg body weight TA.

| | | | Estimate | | | | | |
|---|---|---|---|---|---|---|---|---|
| Variable | Parameter | Units | Brain | Liver | Muscle | Plasma | Spinal cord | Testis |
| TA conc. | Cmax | ng/mL | 194 | 67600 | 1250 | 13400 | 554 | 3030 |
| | Cmax | μM | 0.7 | 259.6 | 4.8 | 222.7 | 2.1 | 11.6 |
| | Tmax | hr | 1 | 1 | 1 | 1 | 1 | 1 |
| | Clast | ng/mL | 66.7 | 508 | 119 | 19.8 | 84.6 | 150 |
| | Tlast | hr | 4 | 24 | 8 | 48 | 4 | 8 |

Figure 11A:
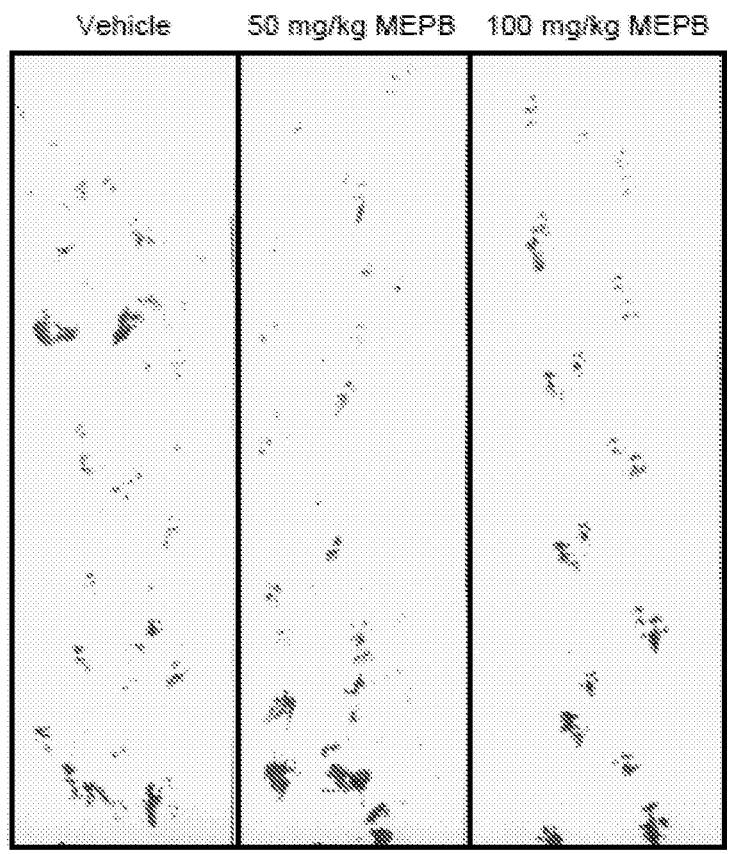
FIGS. 11A-11I demonstrate the effect of MEPB treatment on gait, clasping phenotype, muscle fiber type, and blood chemistry.
Figure 11B:
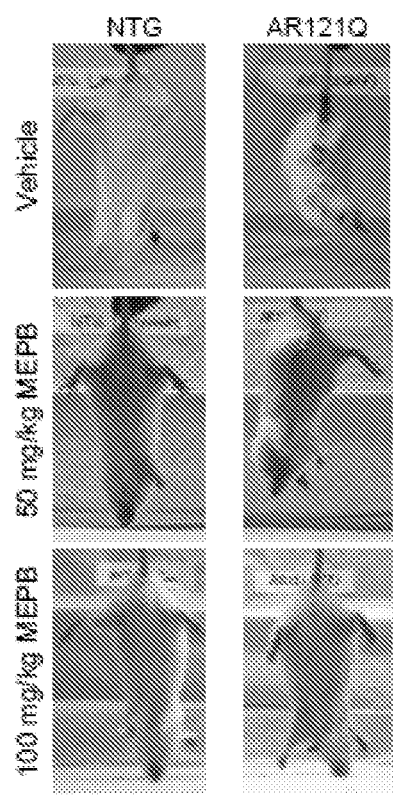
Figure 11C:
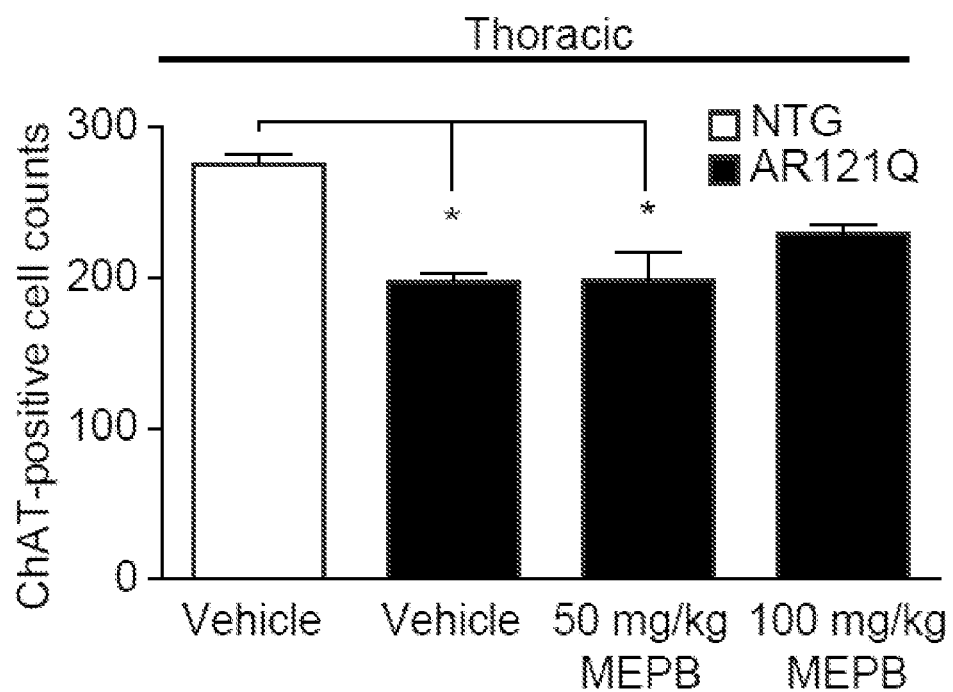
Figure 11D:
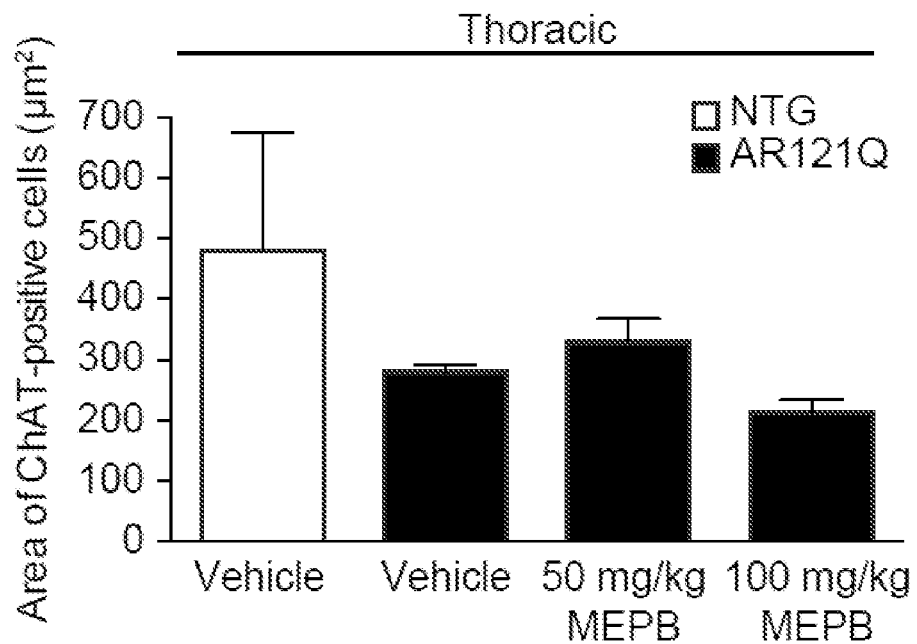
Figure 11E:
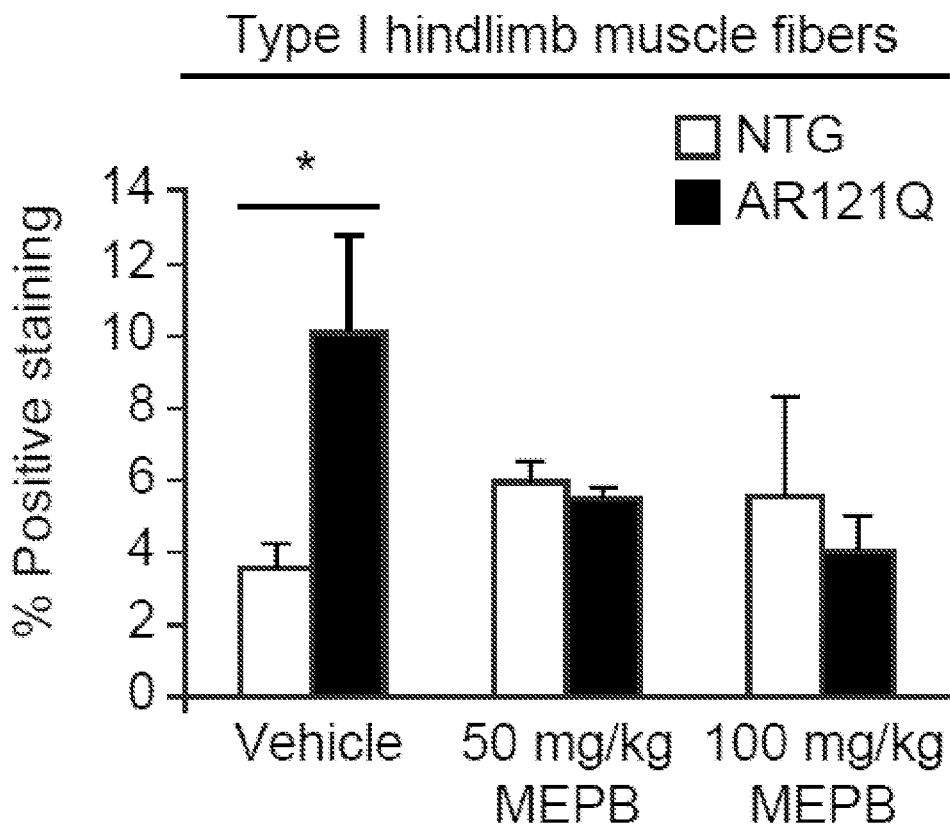
Figure 11F:
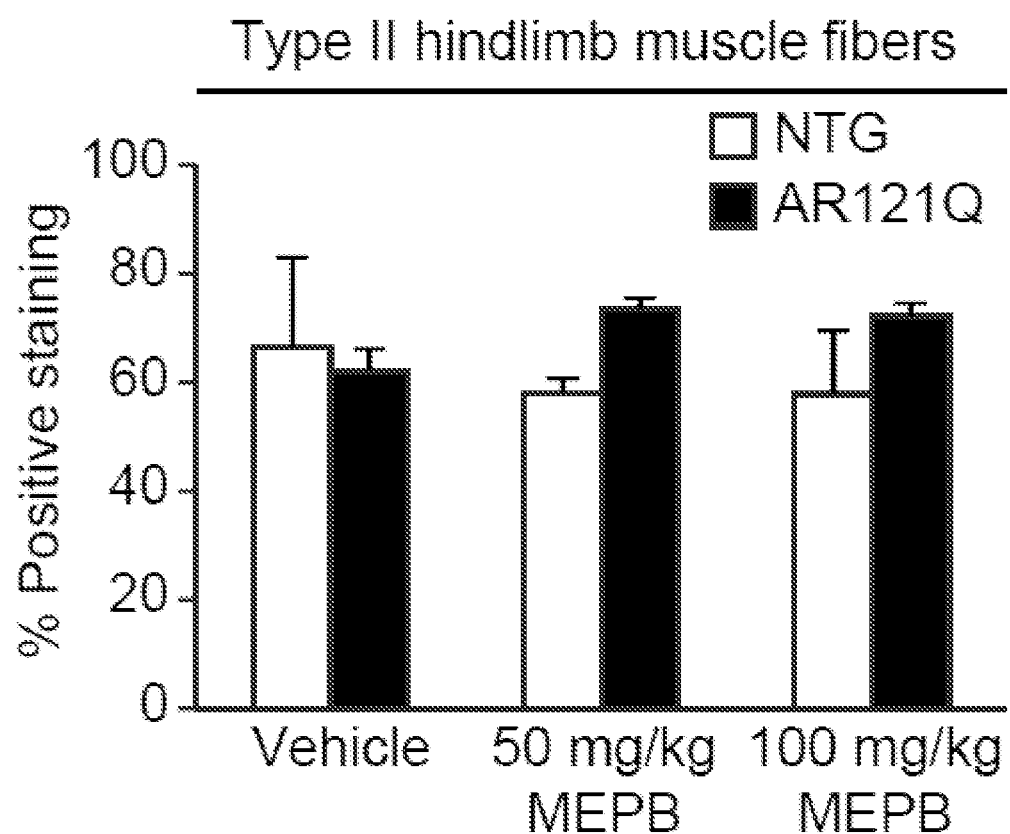

MEPB Demonstrates Efficacy in a Large-Scale
Blinded Preclinical Trial in SBMA Mice To further evaluate the therapeutic capacity of MEPB, we next performed a large-scale, blinded, multi-dose preclinical trial of MEPB treatment in male SBMA mice. Using quantitative measures of SBMA-associated degeneration (body weight, rotarod activity, grip strength, and survival) from the previous pilot study, we performed a statistical power analysis to establish cohort numbers required for a full-scale trial (Table 1). On the basis of this analysis, we assigned at least 10 male NTG or SBMA mice per treatment group. Mice were injected intra-peritoneally with low-dose (50 mg/kg) MEPB, high-dose (100 mg/kg) MEPB, or vehicle (1% DMSO in corn oil) three times per week starting at 4 weeks of age until completion of the trial when mice were 30 weeks of age. Low-dose and especially high-dose MEPB treatment significantly augmented body weight, rotarod activity, and grip strength (FIGS. 4A-4K) and also qualitatively improved gait and hindlimb clasping (FIG. 11A and FIG. 11B). Consistent with improvement in these behavioral parameters, both low-dose and high-dose MEPB treatment significantly reduced the presence of ubiquitin-positive nuclear inclusions in the spinal cord (FIGS. 5A-5B), as well as degenerating myofibers in skeletal muscle (FIGS. 5C-5D). Importantly, both low-dose and high-dose MEPB treatment significantly reduced colocalization of NCAM/PSA-NCAM staining in SBMA mice as compared with vehicle-treated SBMA mice, decreasing these levels similar to those in NTG controls, consistent with amelioration of neurogenic atrophy (FIGS. 5E-5F). Indeed, high-dose MEPB treatment was found to prevent the loss of spinal cord motor neurons (FIG. 11C and FIG. 11D). Moreover, both low-dose and high-dose MEPB treatment restored the frequency of type I myofibers to levels observed in NTG control mice, whereas type II myofiber frequency remained unaffected (FIG. 11E and FIG. 11F), further demonstrating the efficacy potential of AF2 modulation for attenuation of SBMA-associated muscle degeneration.

Figure 5A:
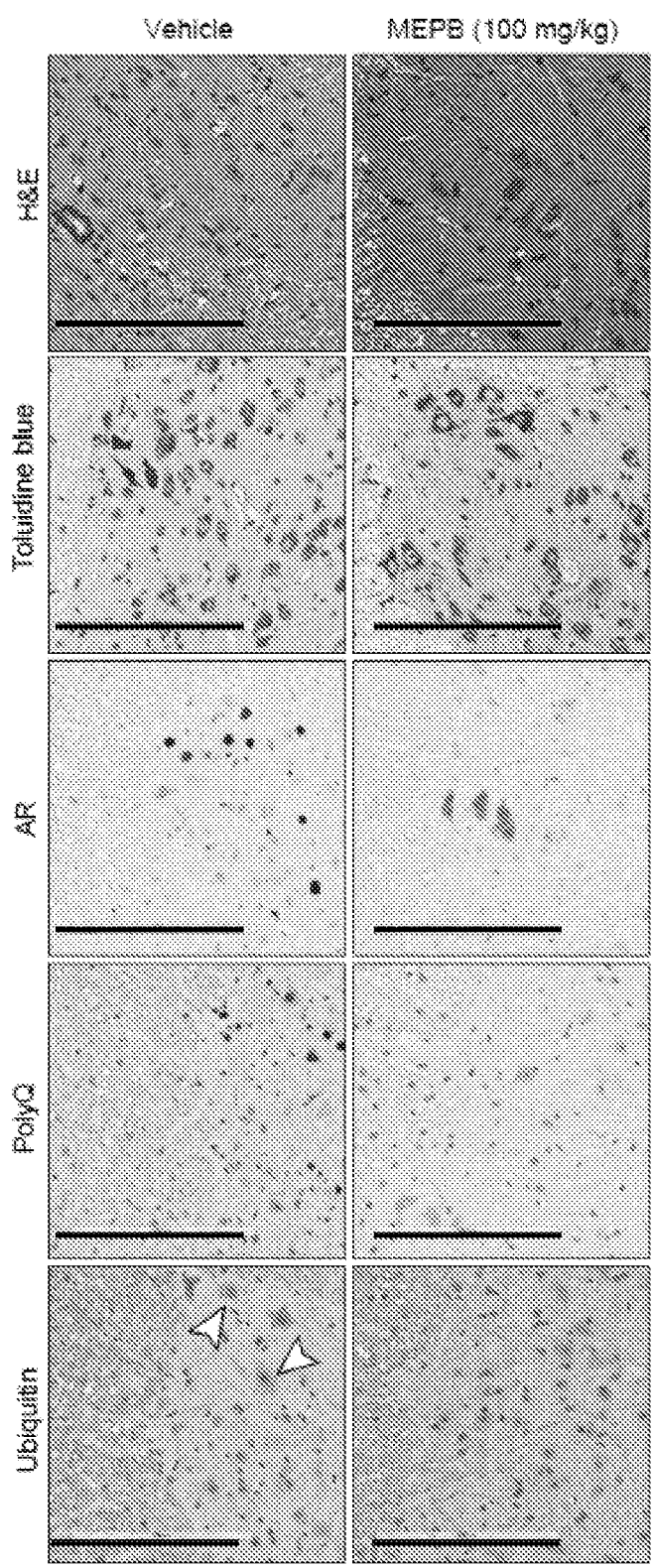
FIGS. 5A-5G demonstrate MEPB reduces degeneration in spinal cord and skeletal muscle of SBMA mice.
Figure 5B:
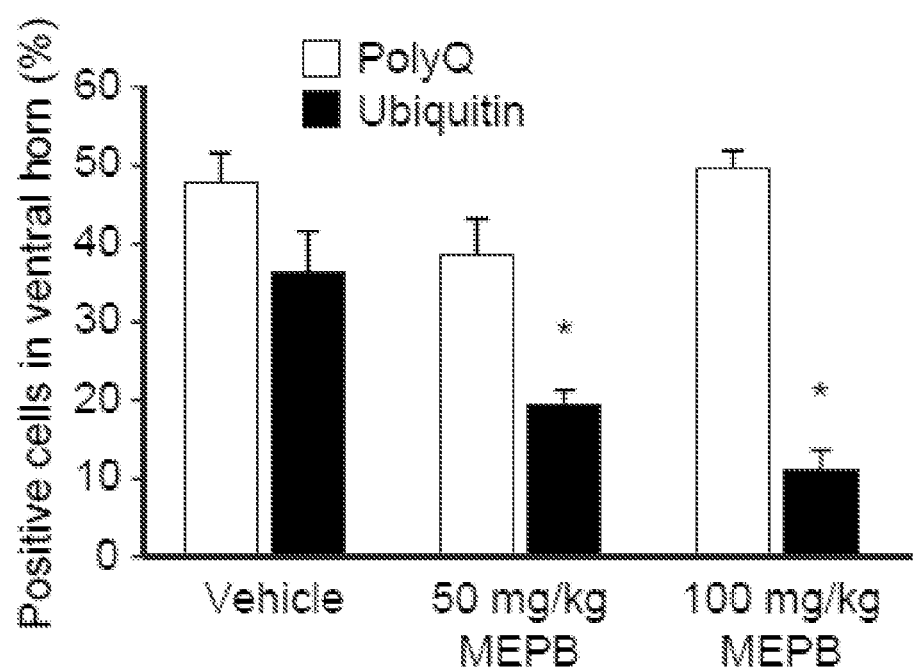
Figure 5C:
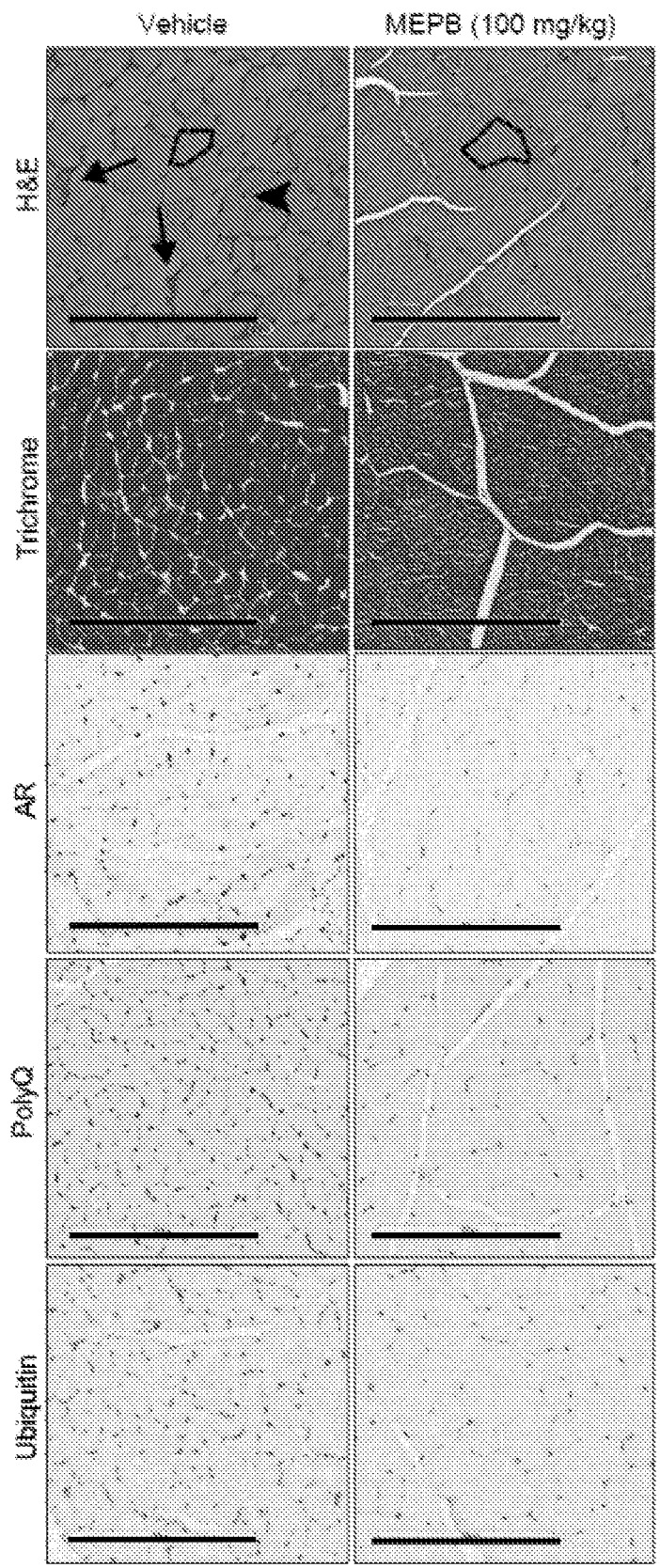
Figure 5D:
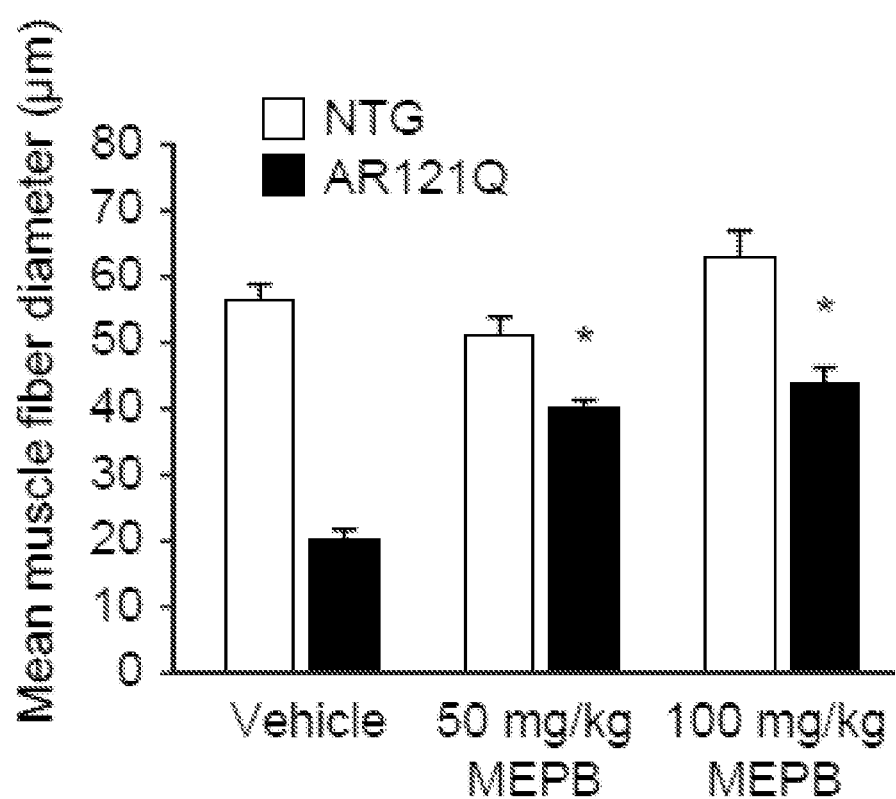
Figure 5E:
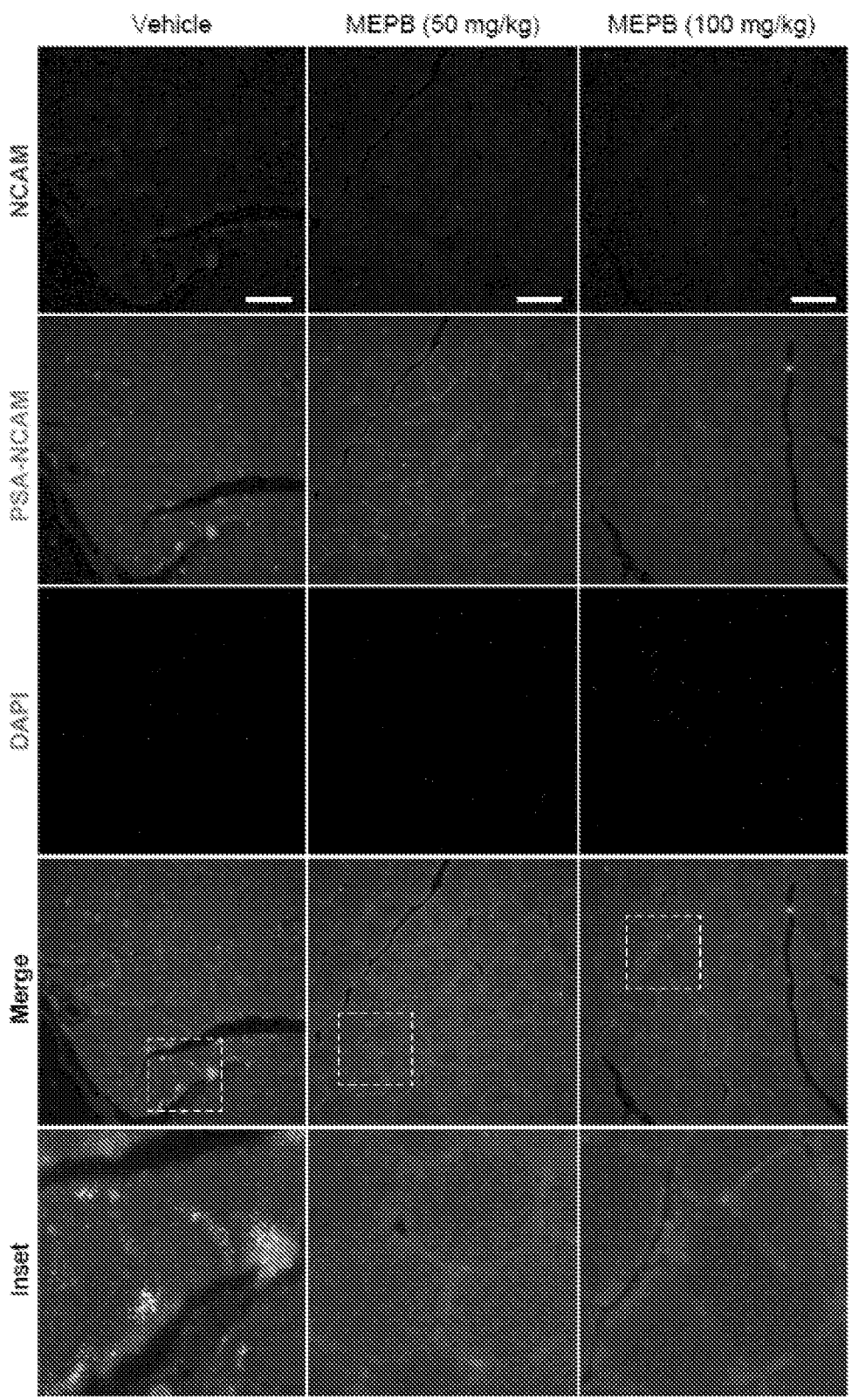
Figure 5F:
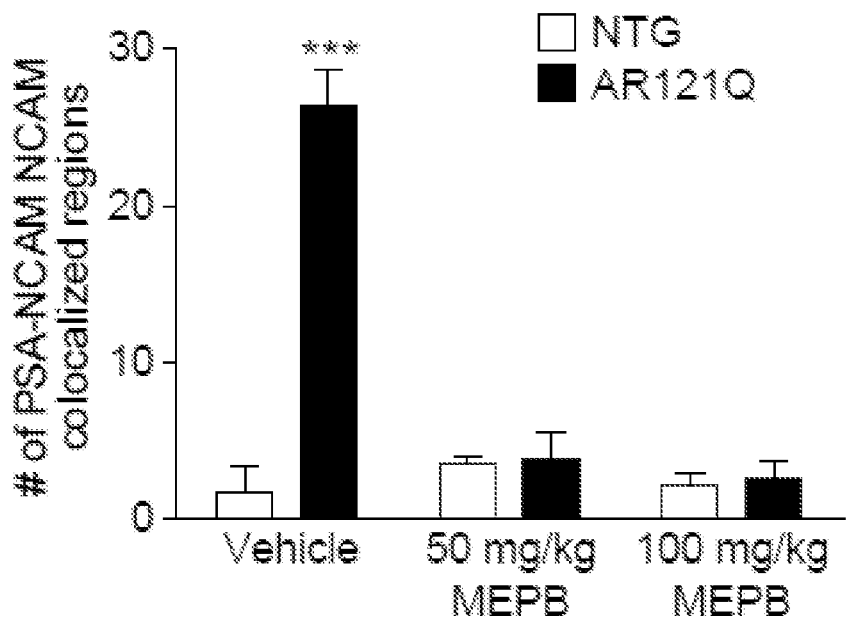
Figure 5G:
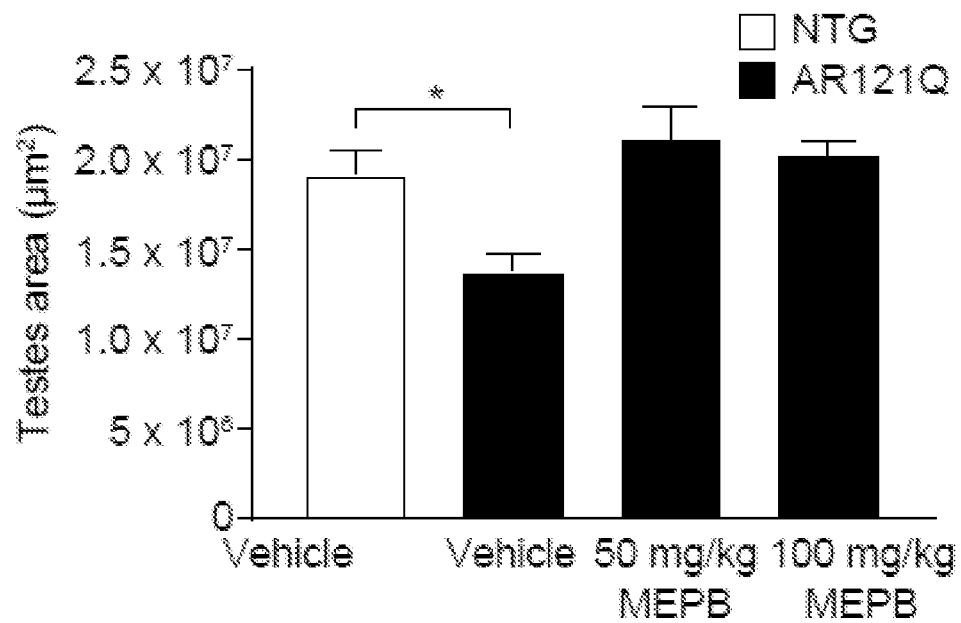

Finally, testicular atrophy in the SBMA mice was reversed with both low-dose and high-dose MEPB treatment (FIG. 5G), which is not only consistent with overall improvement of the SBMA phenotype, but also underscores the selective nature of AR modulation by MEPB.

Figure 4A:
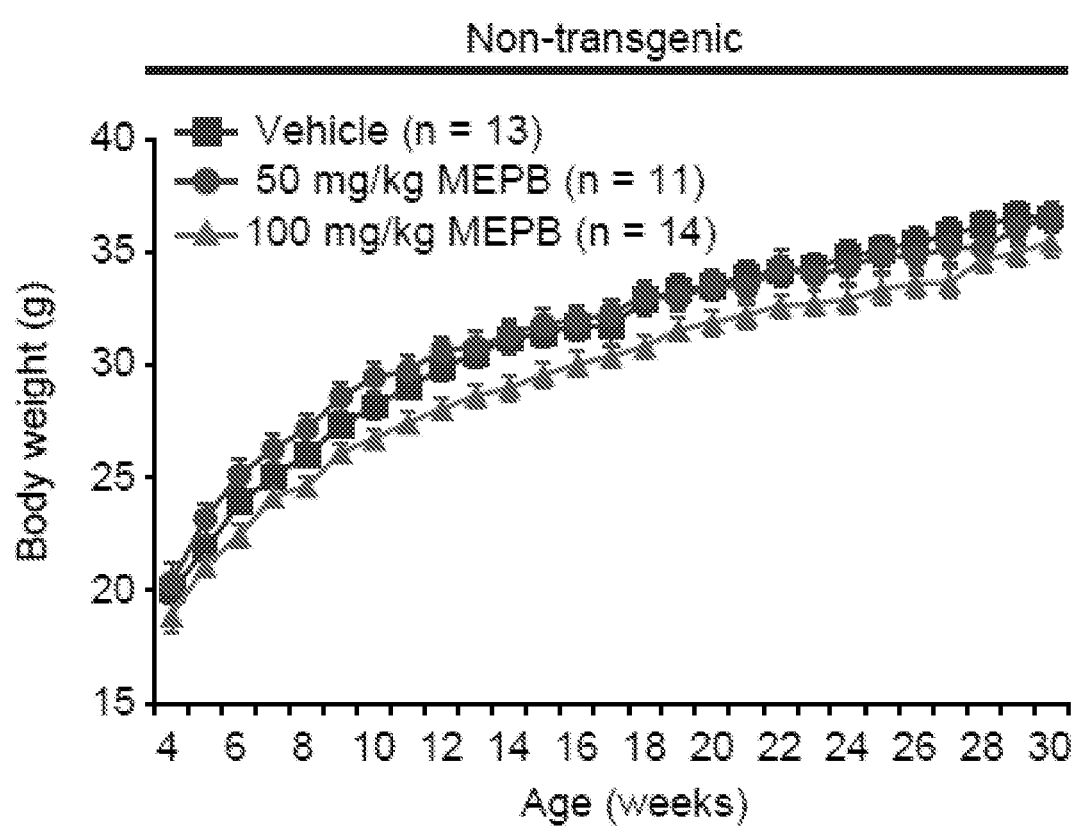
FIGS. 4A-4K demonstrate MEPB improves phenotypic outcomes and improves quality of life parameters in a large-scale preclinical trial in SBMA mice.
Figure 4B:
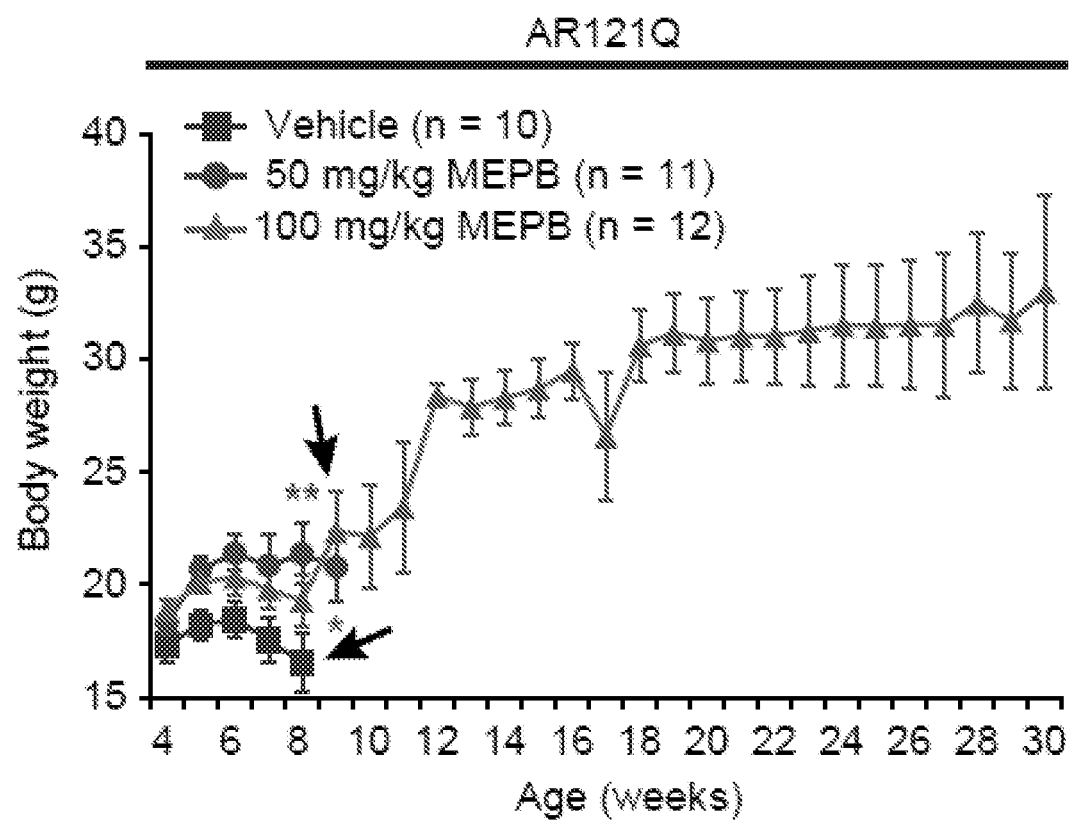
Figure 4C:
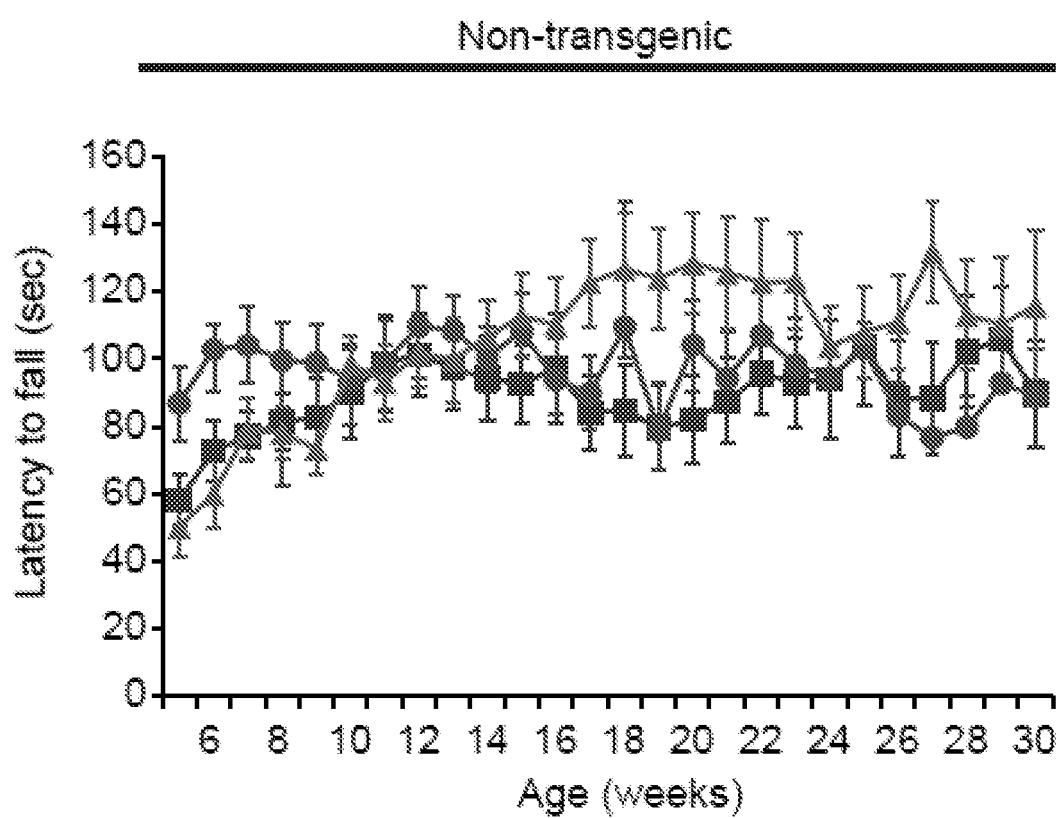
Figure 4D:
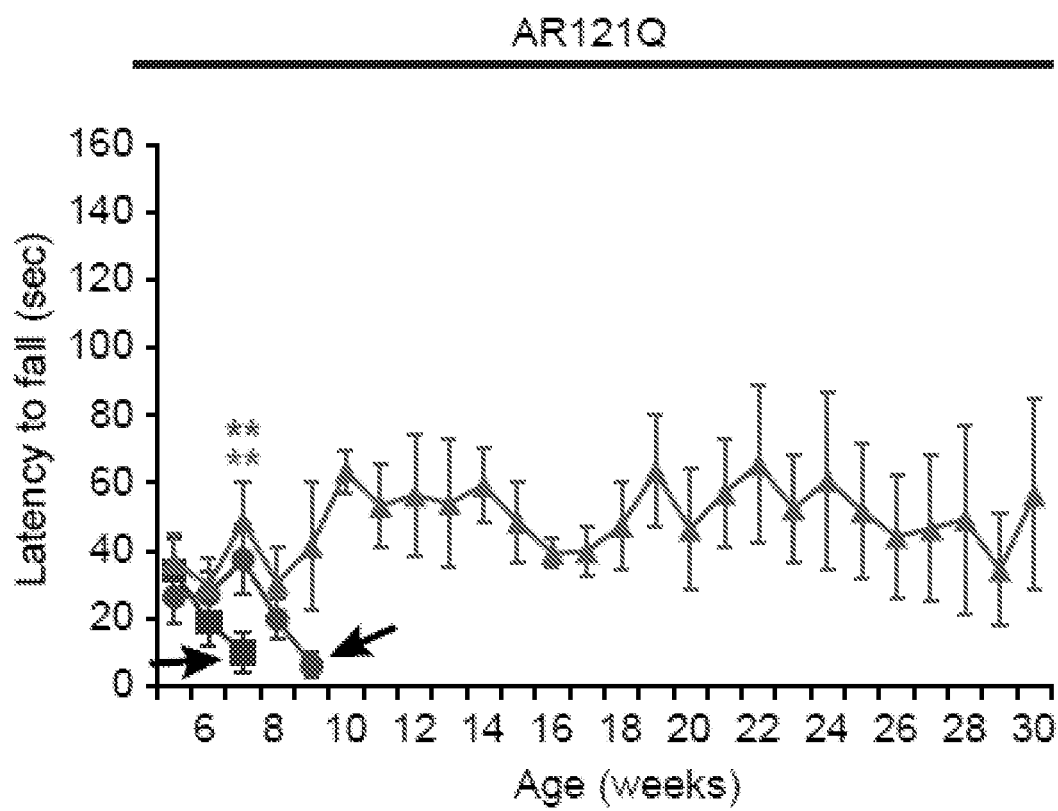
Figure 4E:
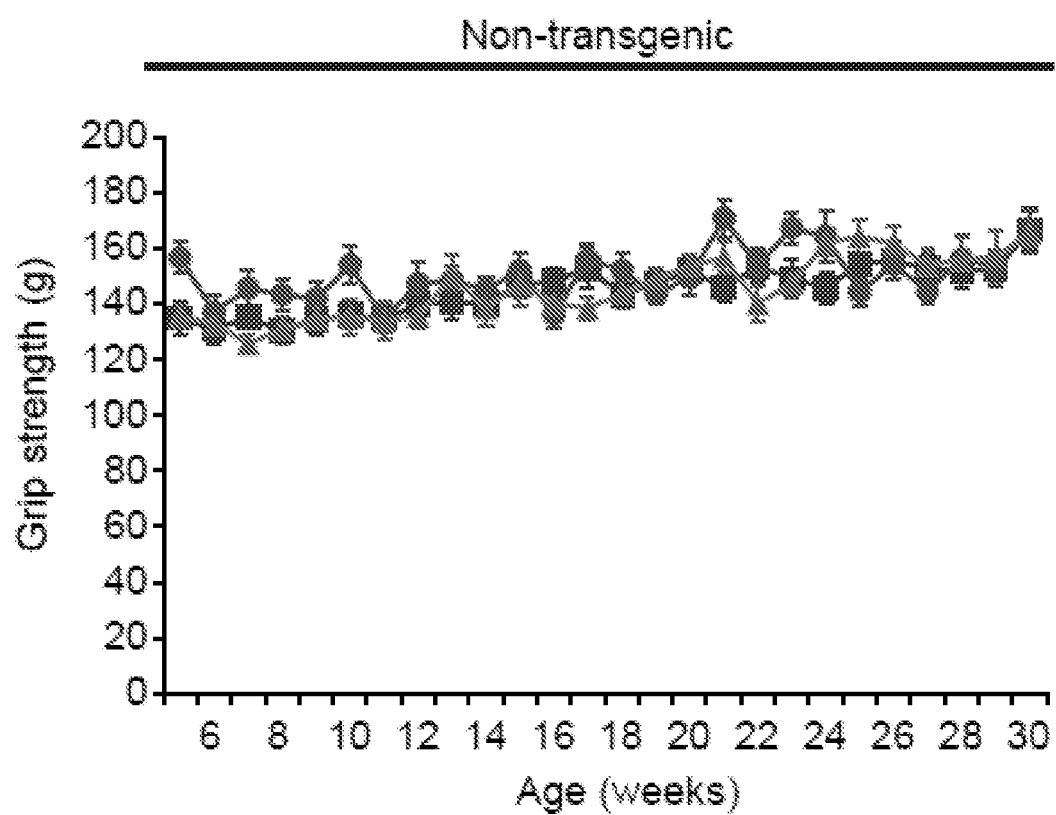
Figure 4F:
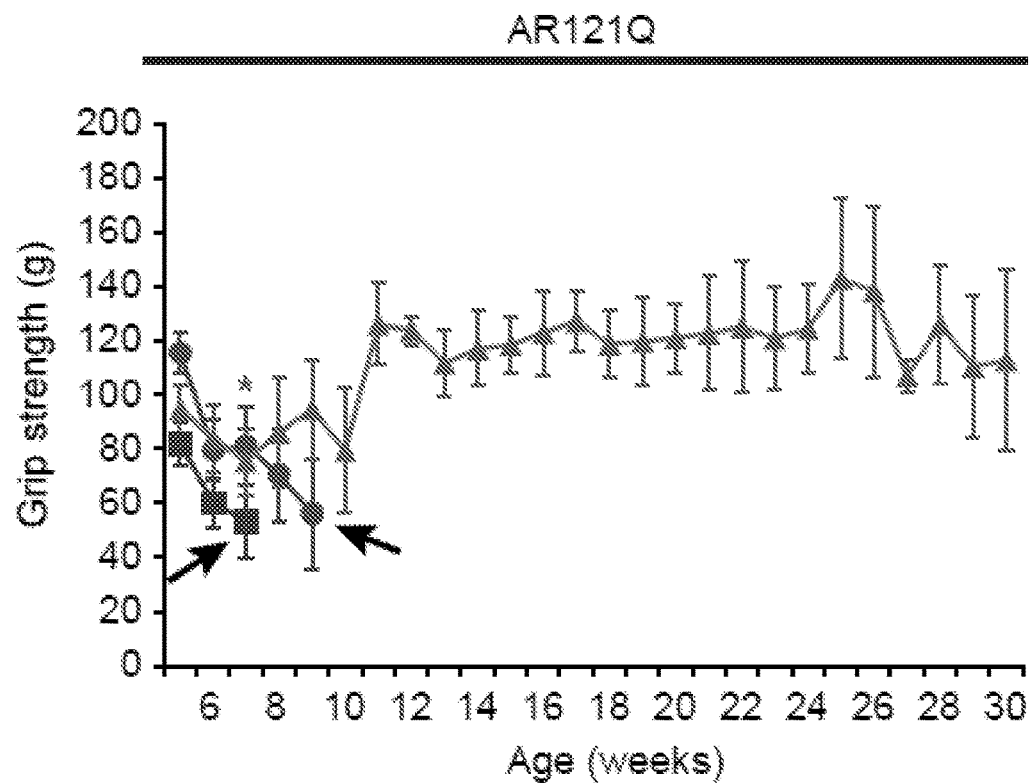
Figure 4G:
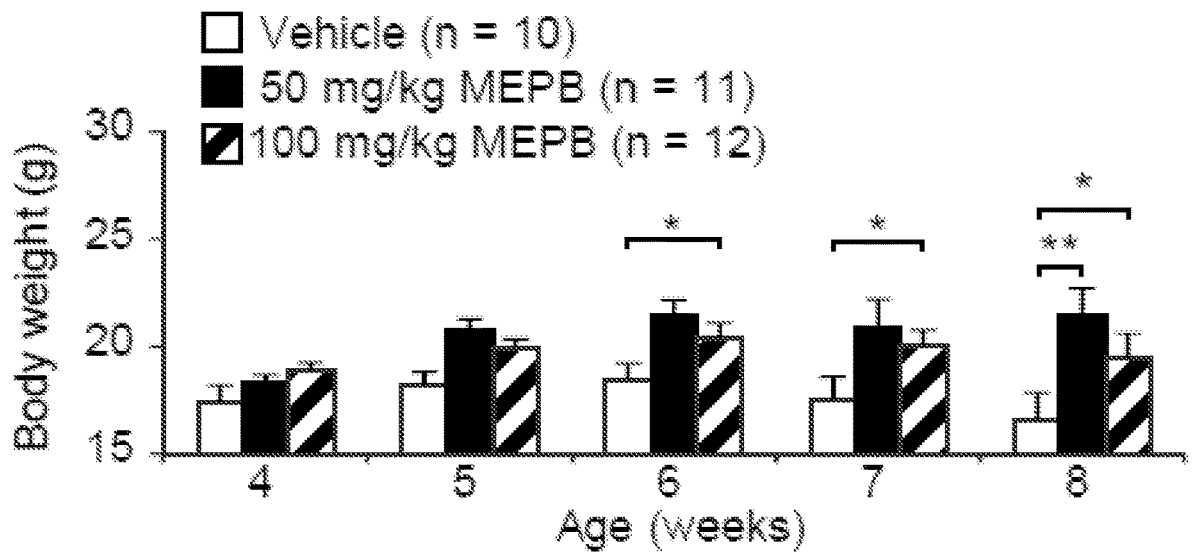
Figure 4H:
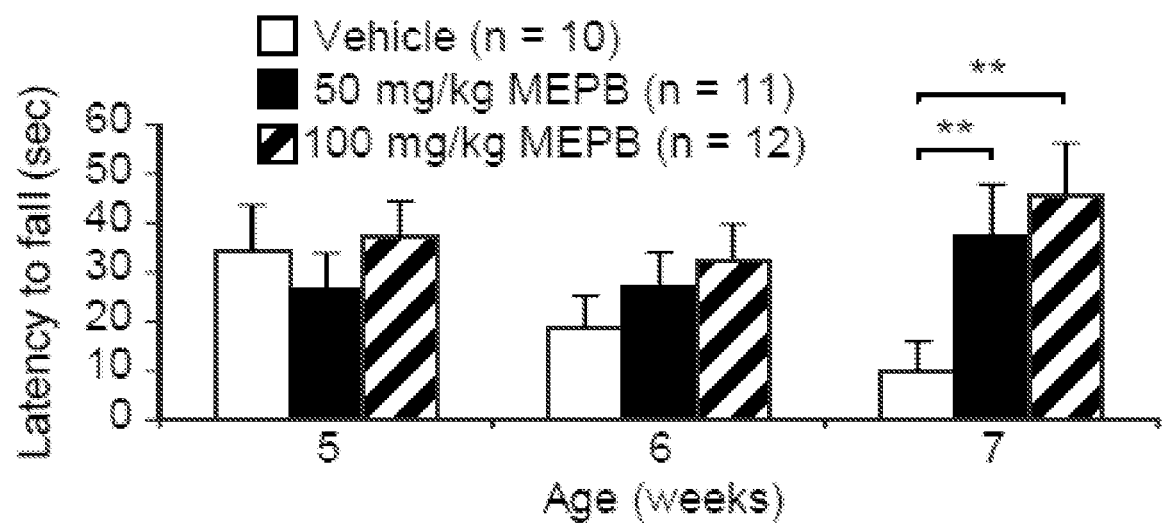
Figure 4I:
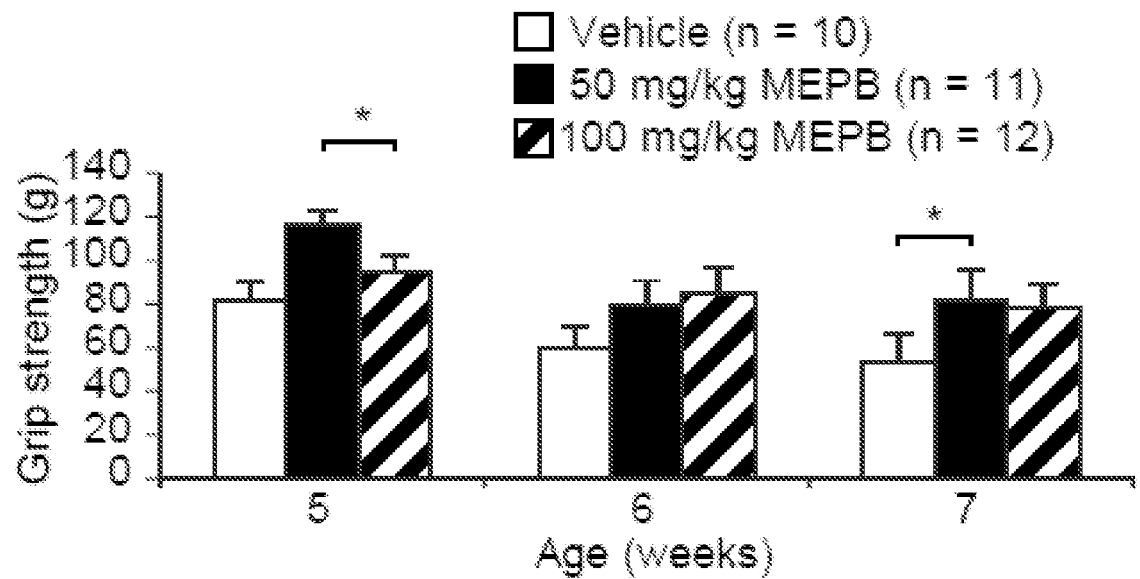
Figure 4J:
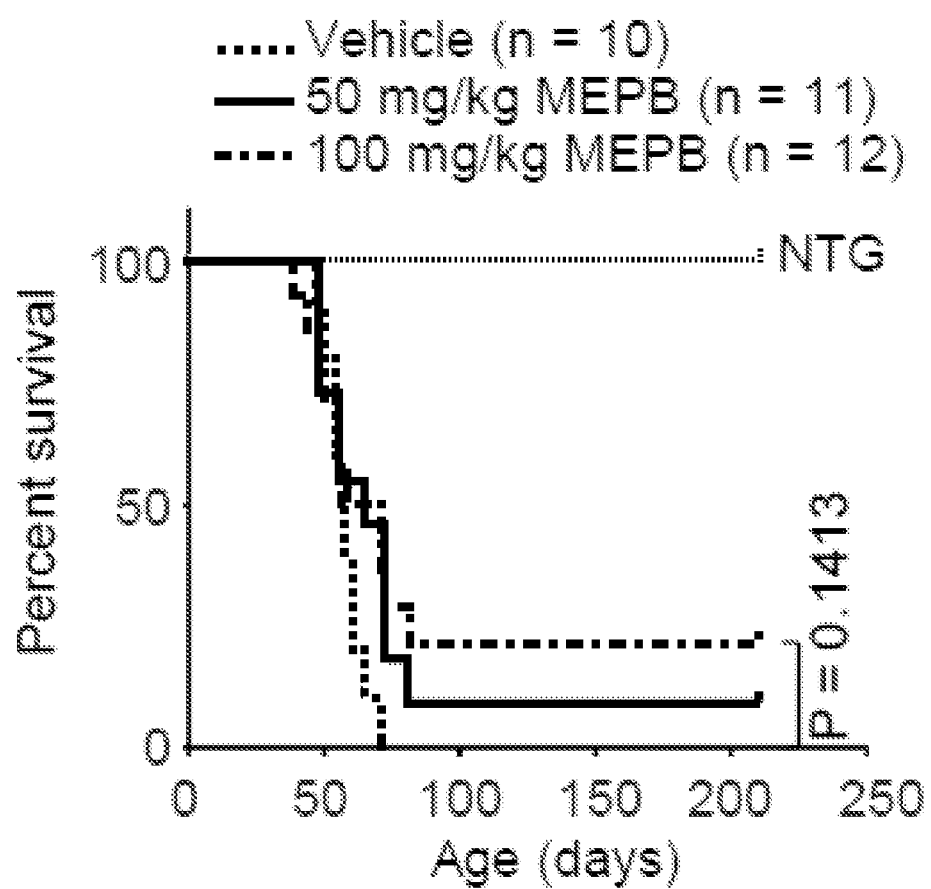
Figure 4K:
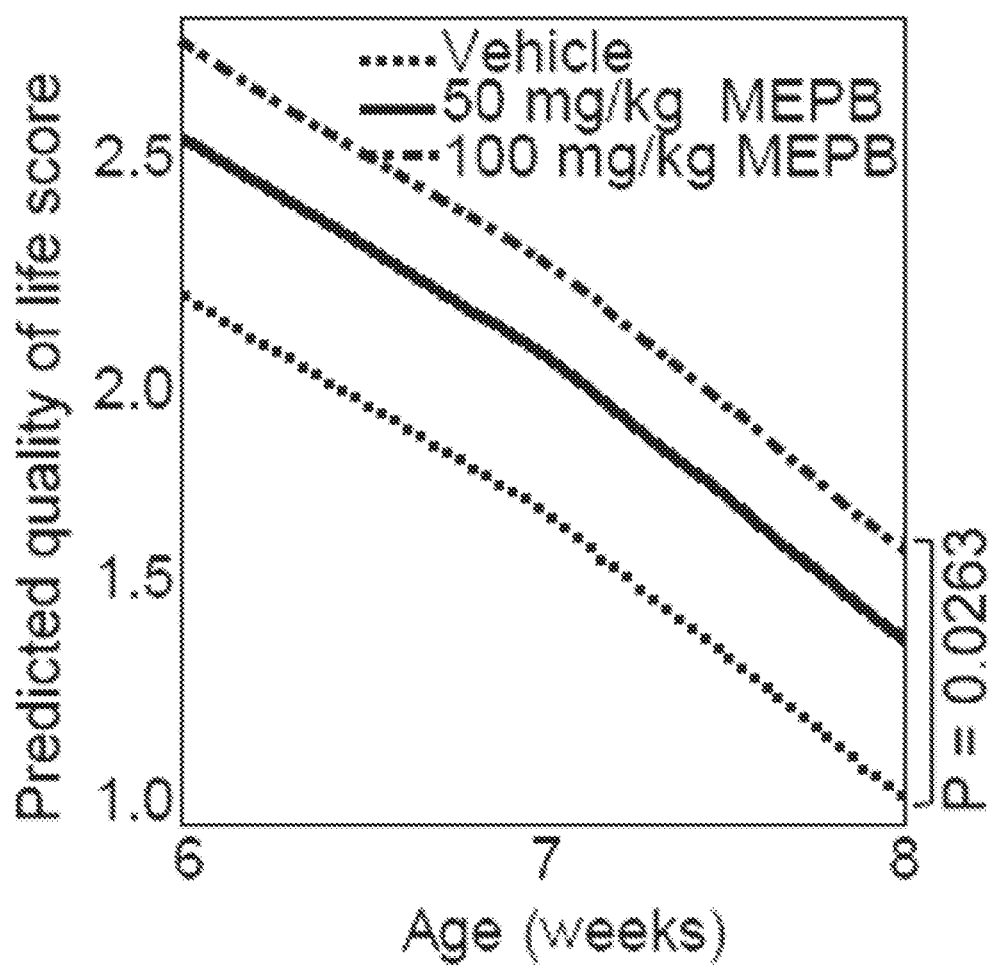
Figure 11G:
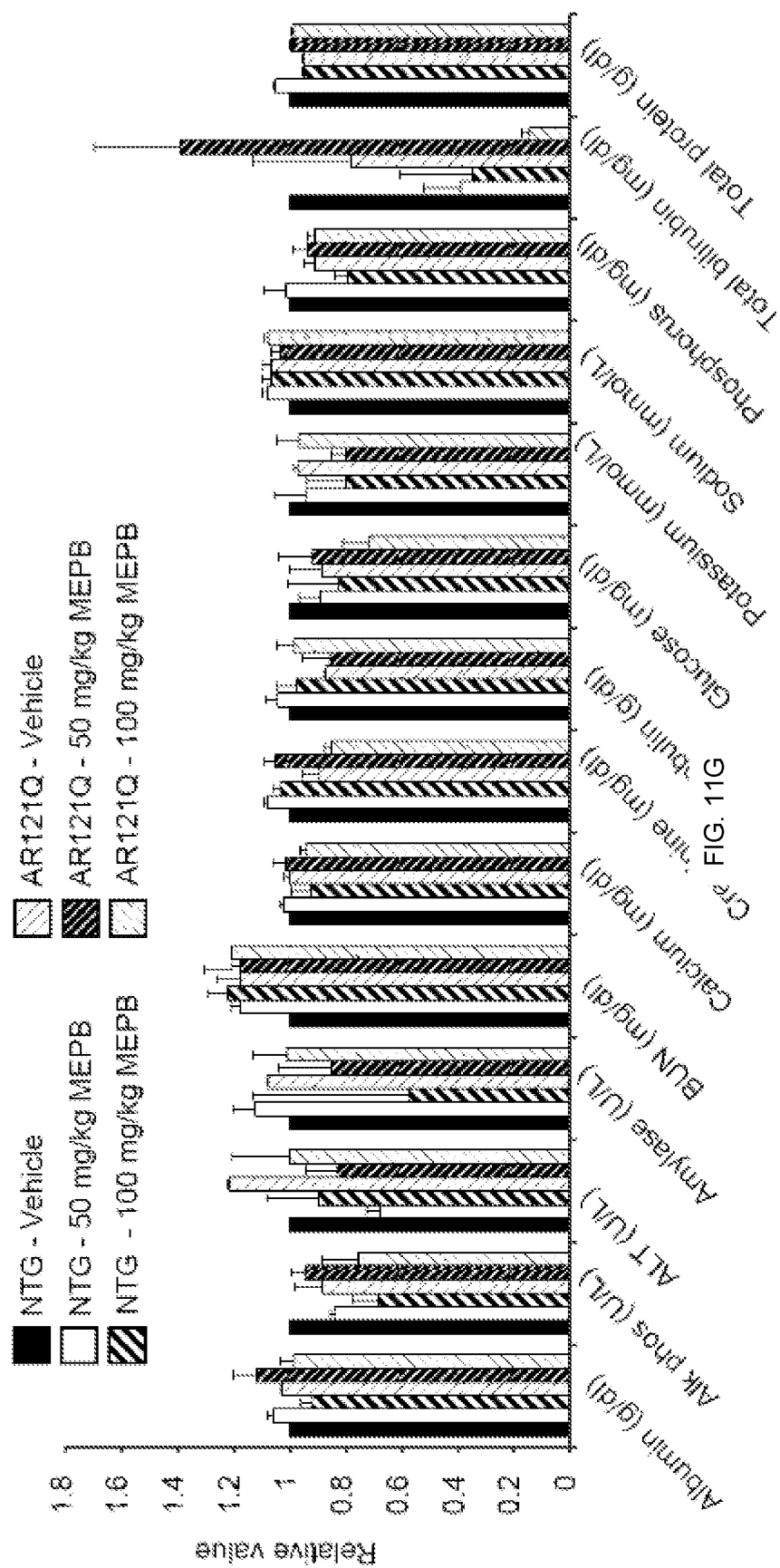
Figure 11H:
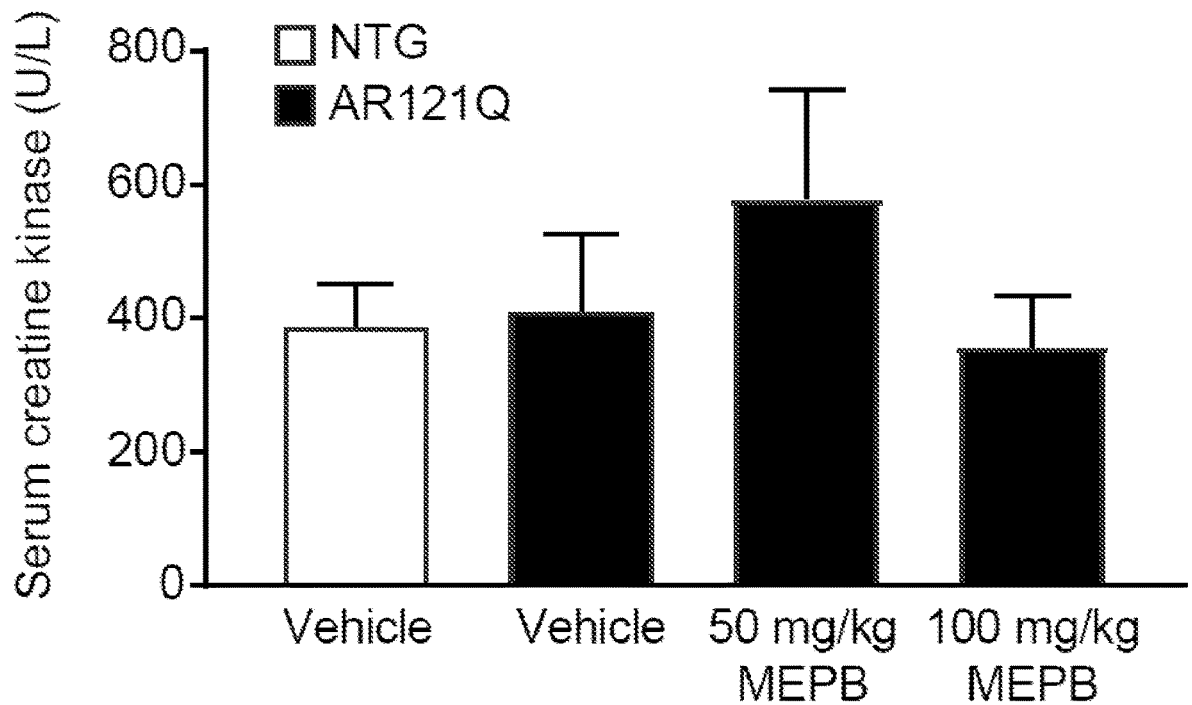
Figure 11I:
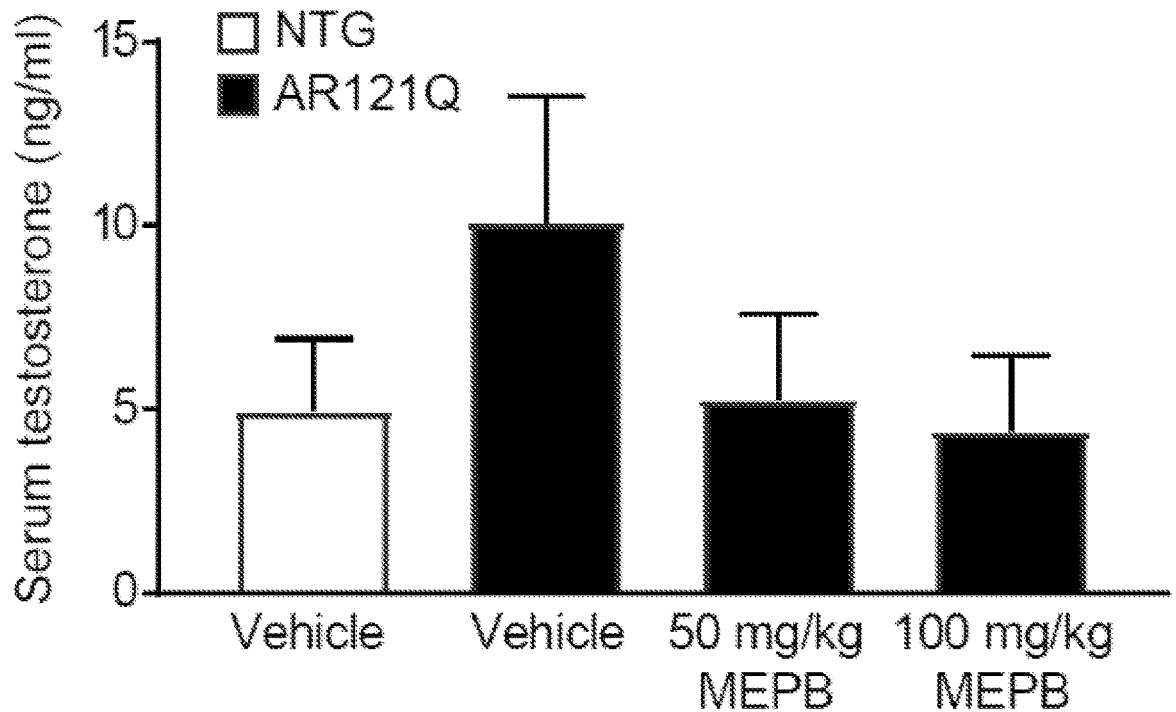

Neither low-dose nor high-dose MEPB treatment significantly altered survival of SBMA mice, although a dose-dependent trend in increased survival was present (FIG. 4J). It should be noted that measurement of mouse "survival" in this trial were confounded by protocol guidelines designed to minimize morbidity in experimental animals. Mice were checked daily by our veterinary staff and recommendations to euthanize individual animals were made based on loss of 10% body weight or subjective signs of hindlimb weakness that might be severe enough to limit an animal's ability to reach the feeder. However, when other phenotypic measurements (viz., body weight, rotarod activity, and grip strength) were compiled along with survival data to generate a QOL score, high-dose MEPB treatment significantly improved the QOL of SBMA mice (FIG. 4K). Furthermore, MEPB treatment (low-dose or high-dose) did not significantly change blood chemistry of either NTG or SBMA mice (FIGS. 11G-11I), and MEPB treatment (low-dose or high-dose) had no measurable effect on any assays of neuromuscular function in NTG control mice, suggesting minimal MEPB-induced toxicity (FIGS. 4A-4K and FIG. 11B). Together, these findings demonstrate that AF2 modulation by MEPB in SBMA mice improves multiple primary outcomes associated with reduced QOL in patients with SBMA, such as attenuated muscle strength, diminished coordination, and loss of body mass, without apparent adverse effects.

Figure 6A:
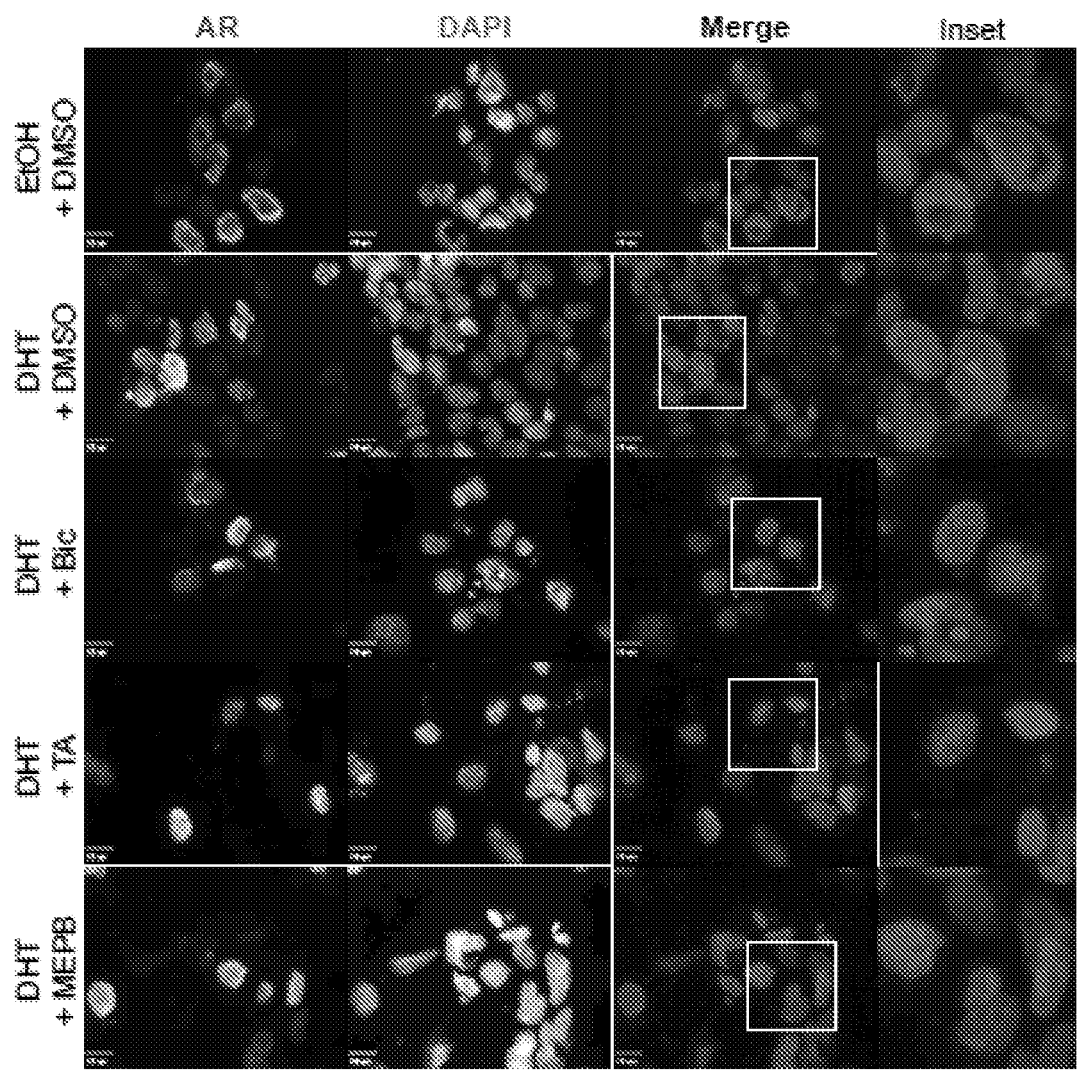
FIGS. 6A-6E demonstrate AF2 modulation does not inhibit AR functional activity.
Figure 6B:
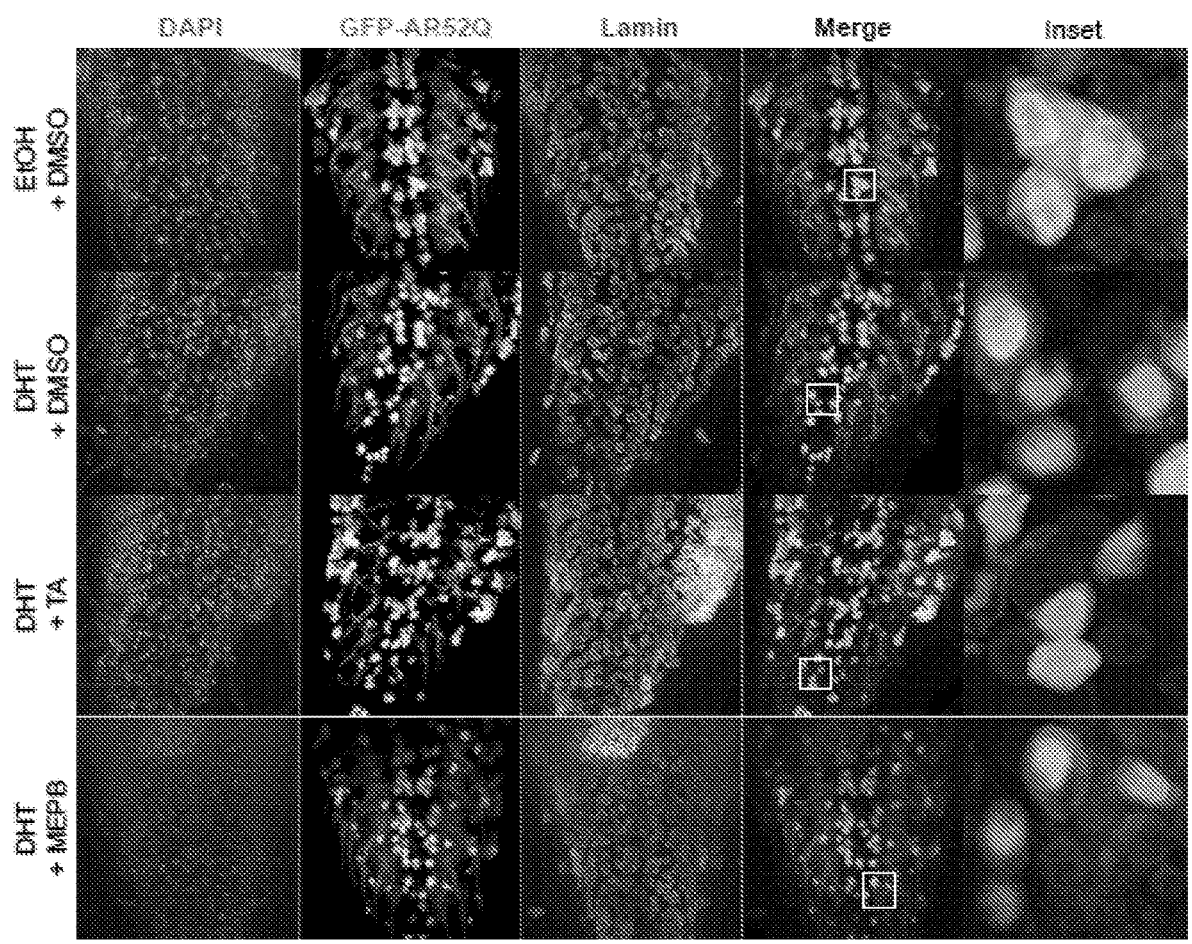
Figure 6C:
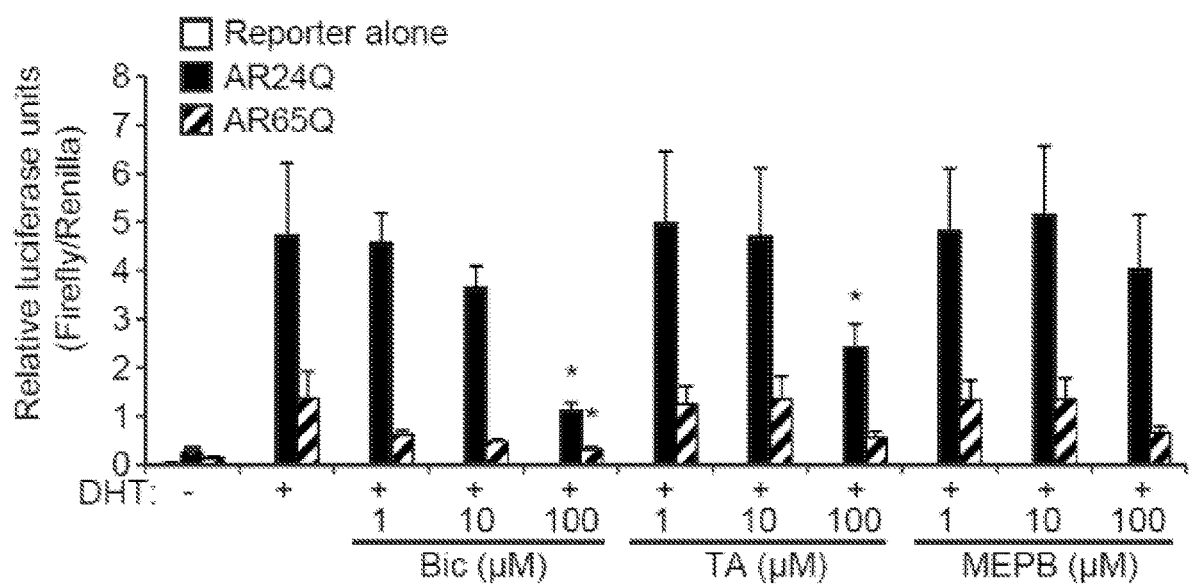
Figure 6D:
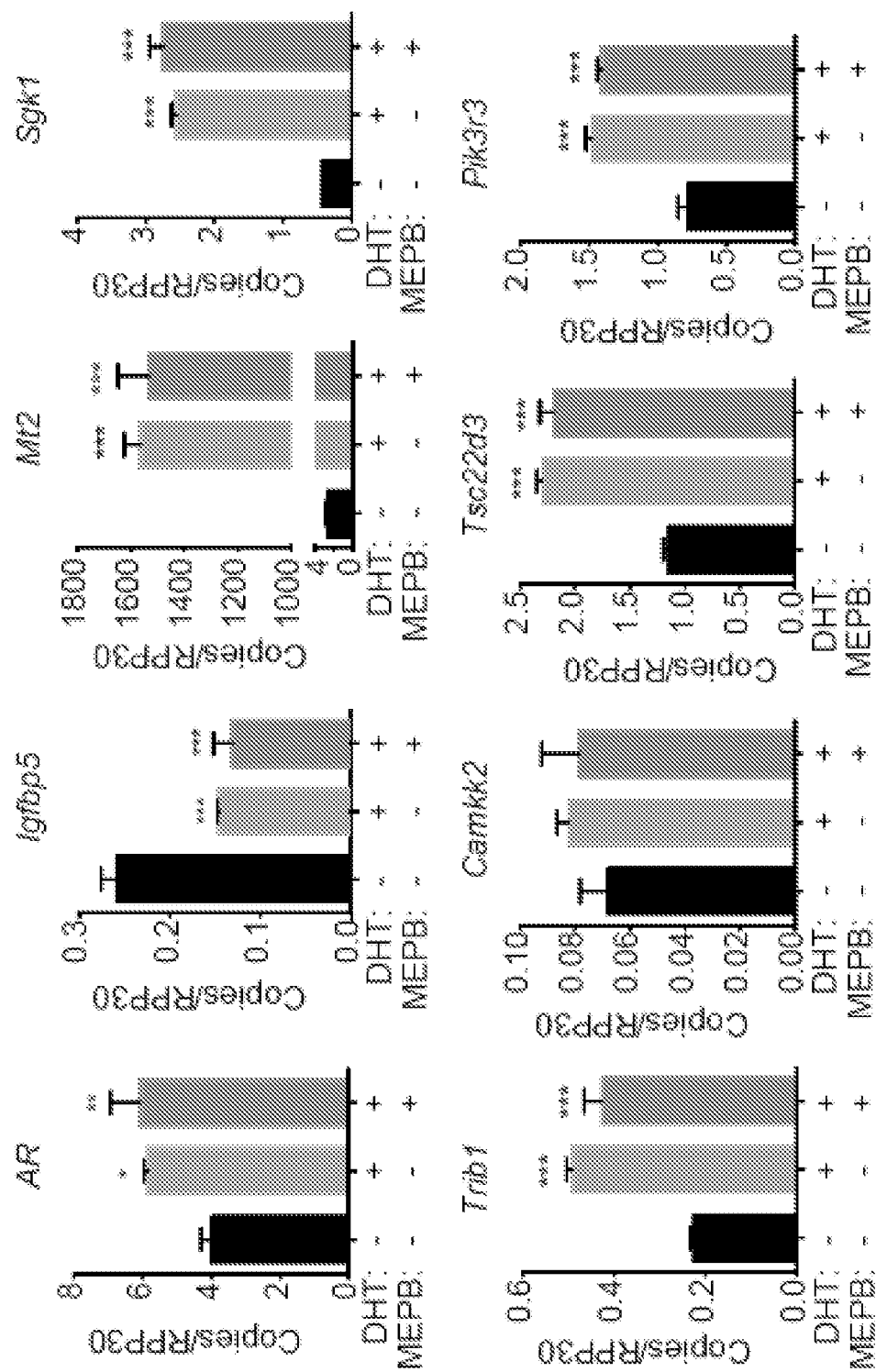
Figure 6E:
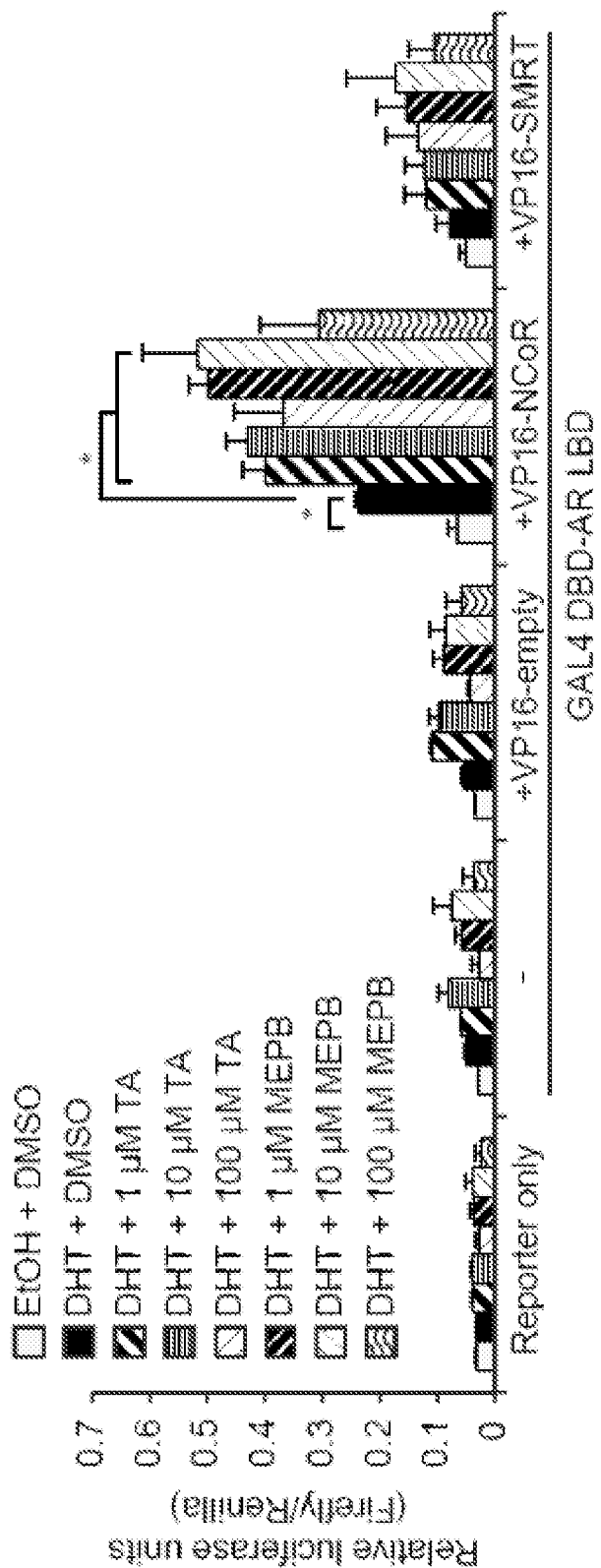
Figure 7A:
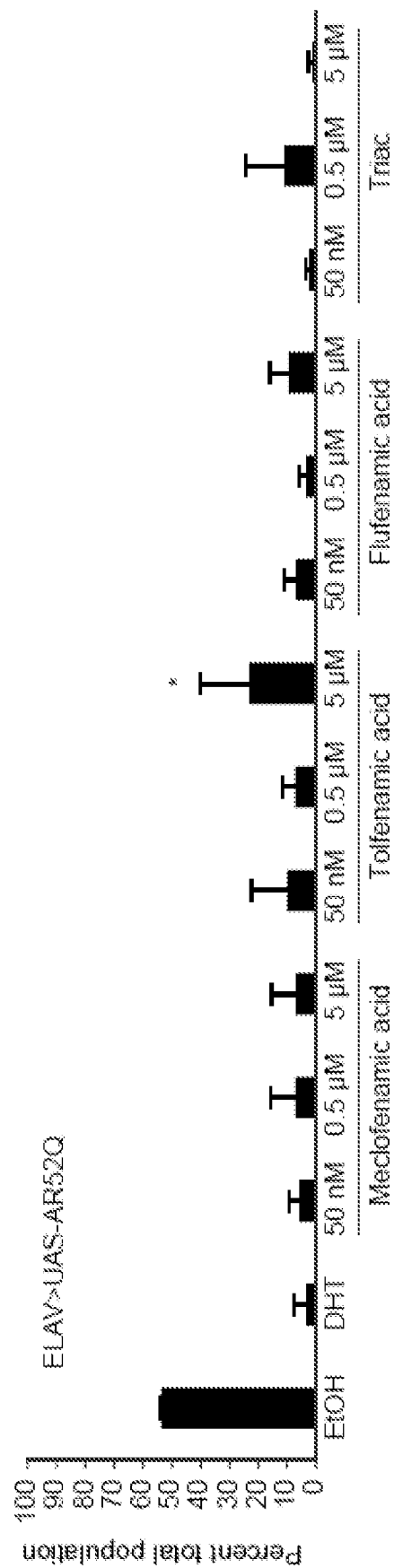
FIGS. 7A-7F demonstrate screening of AF2-modulating compounds in a Drosophila model of SBMA.
Figure 7B:
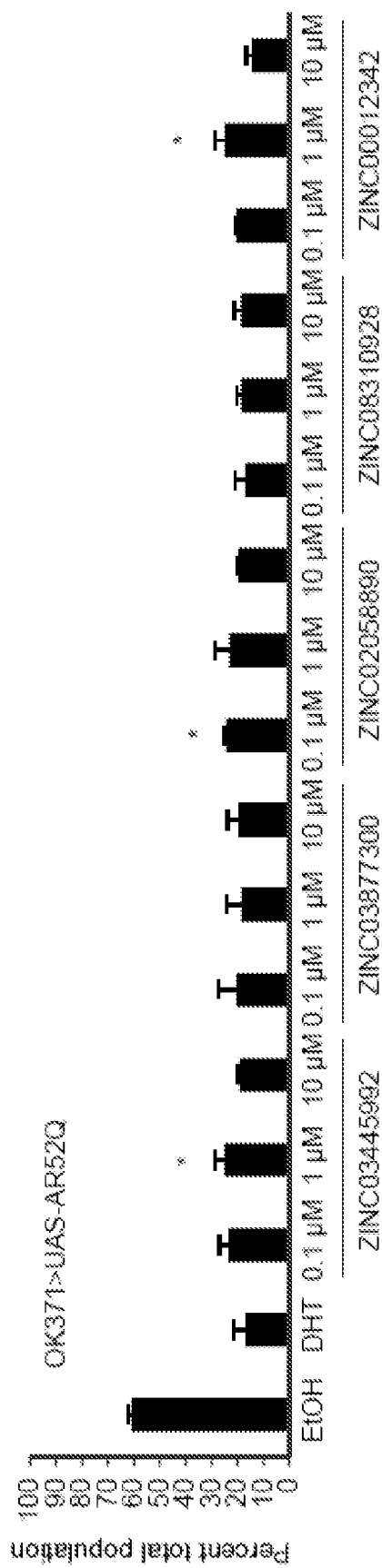
Figure 7C:
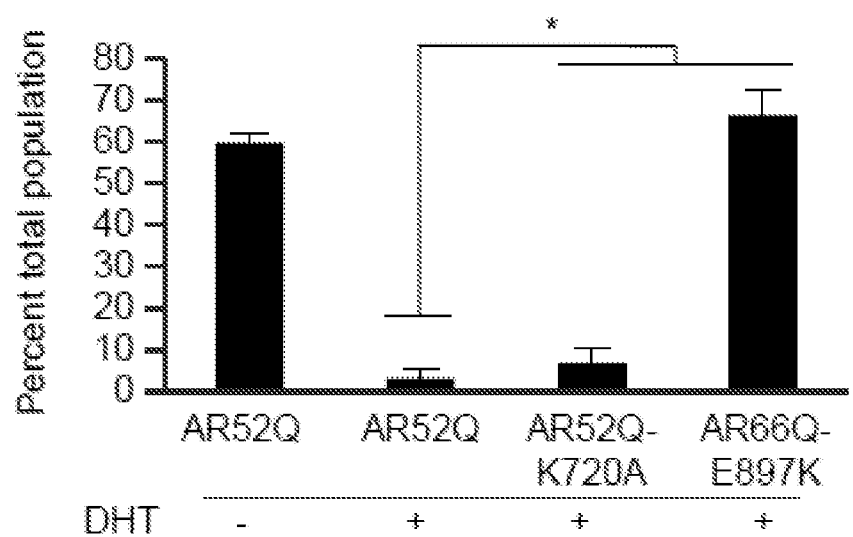
Figure 7D:
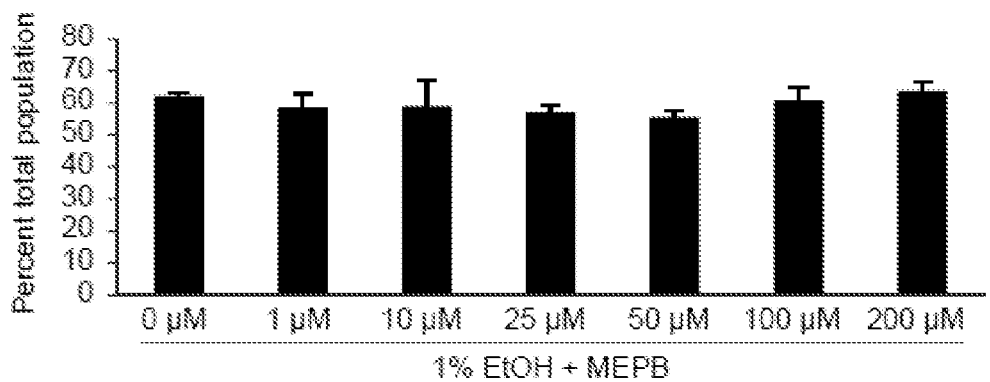
Figure 7E:
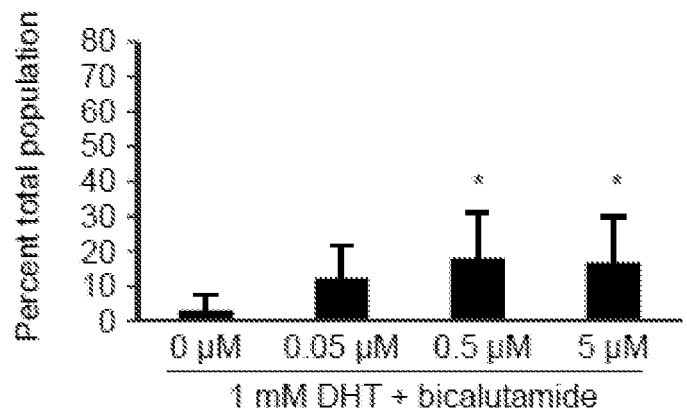
Figure 7F:
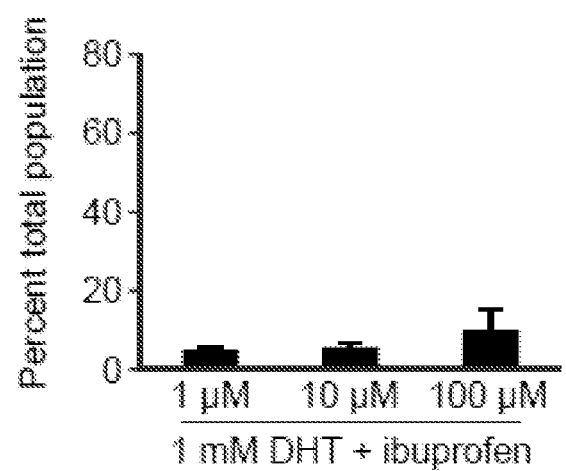
Figure 12A:
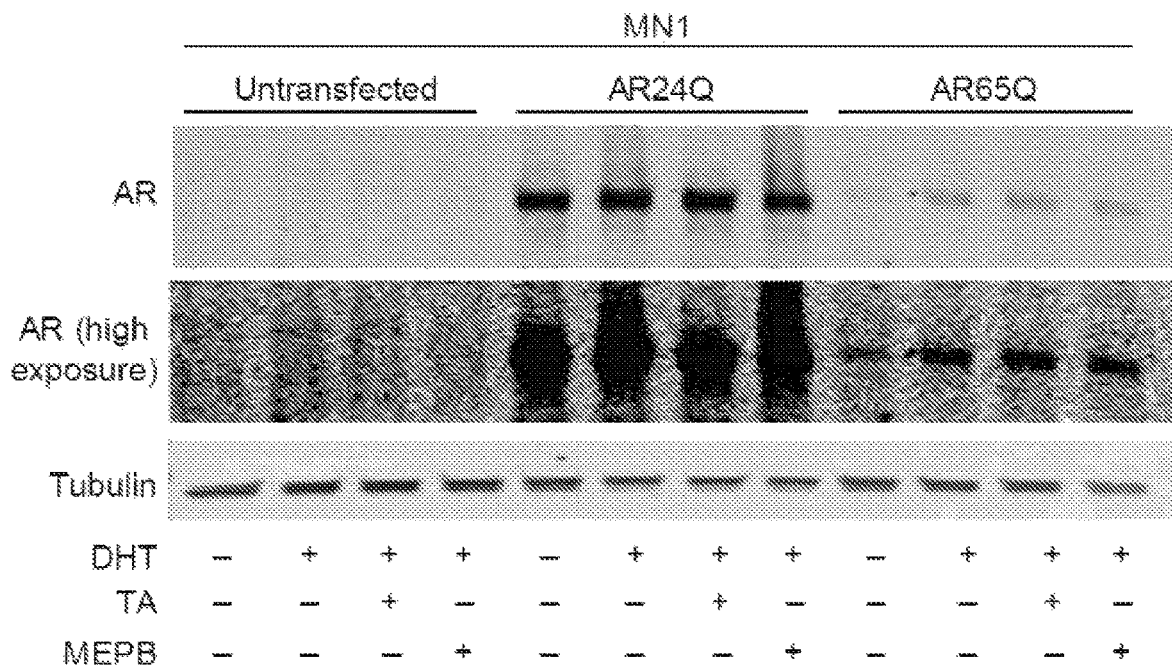
FIGS. 12A-12F demonstrate the effect of AF2 modulators on AR protein levels in MN1 and HEK293T cells.
Figure 12B:
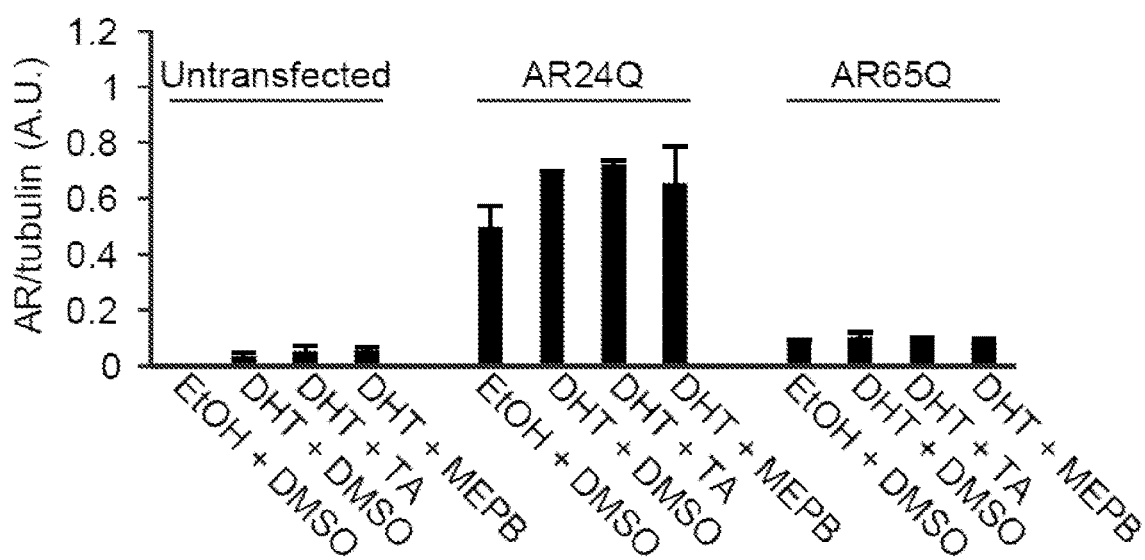
Figure 12C:
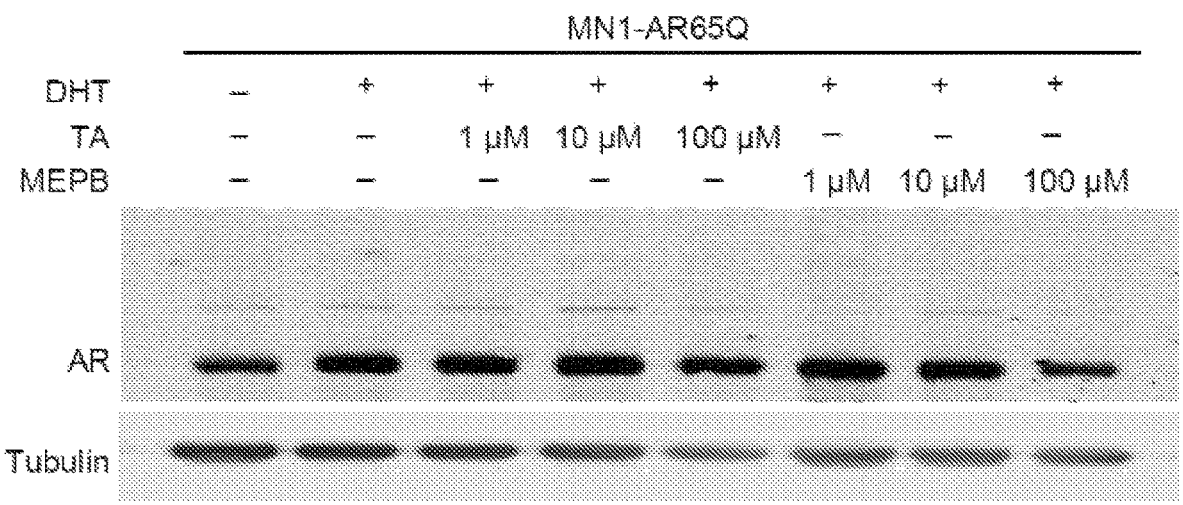
Figure 12D:
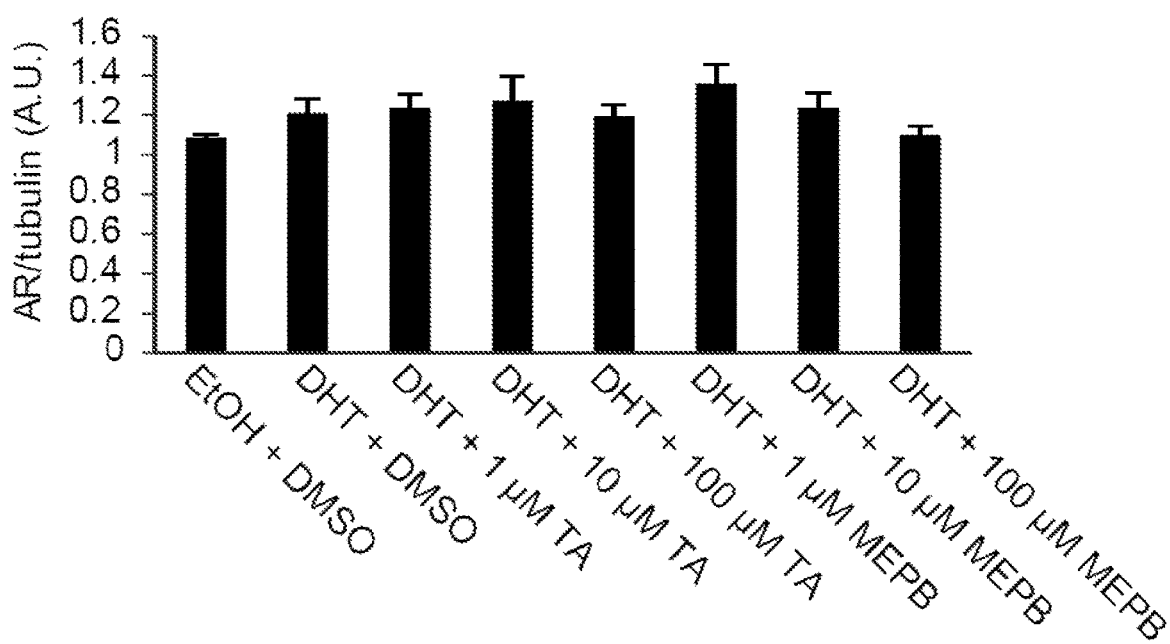
Figure 12E:
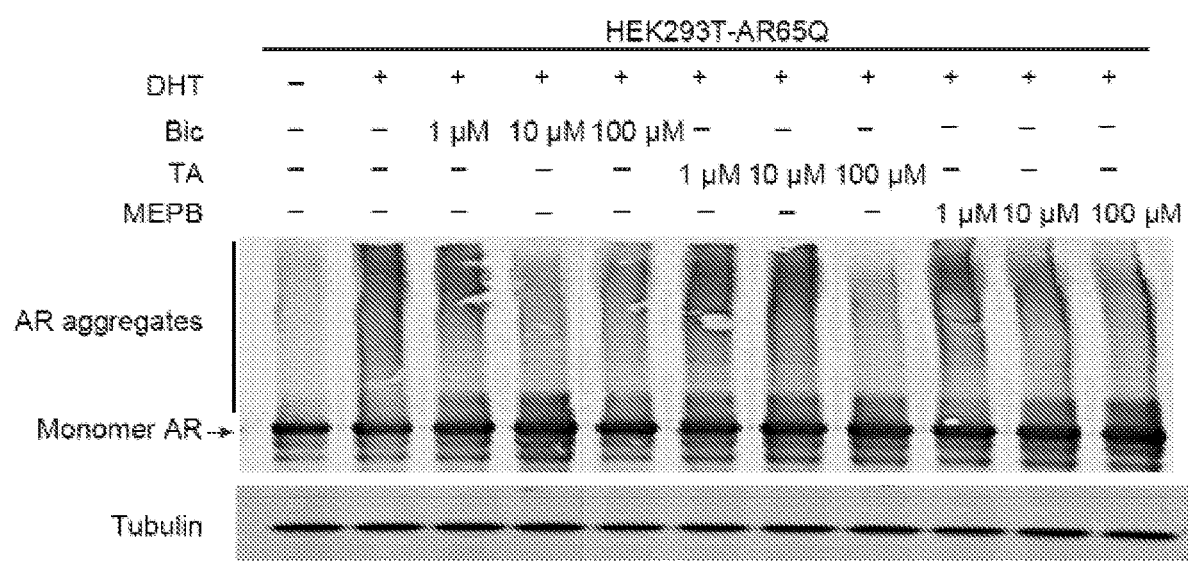
Figure 12F:
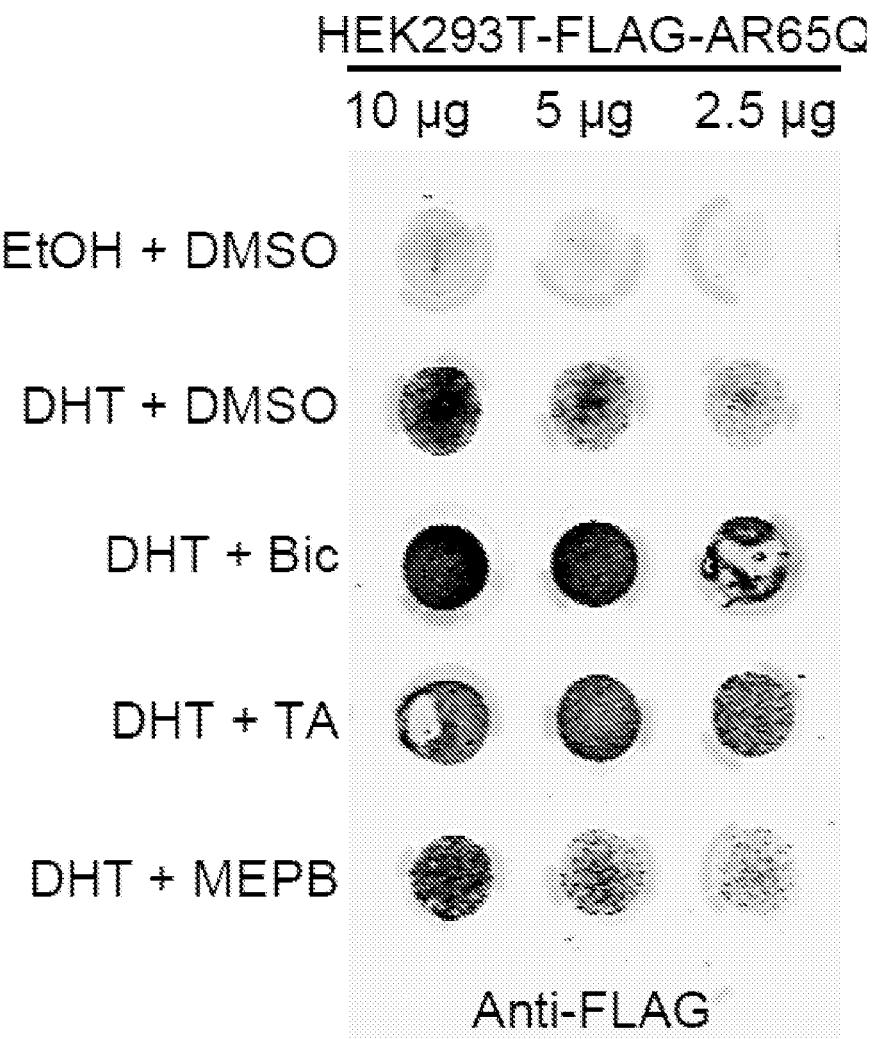
Figure 13A:
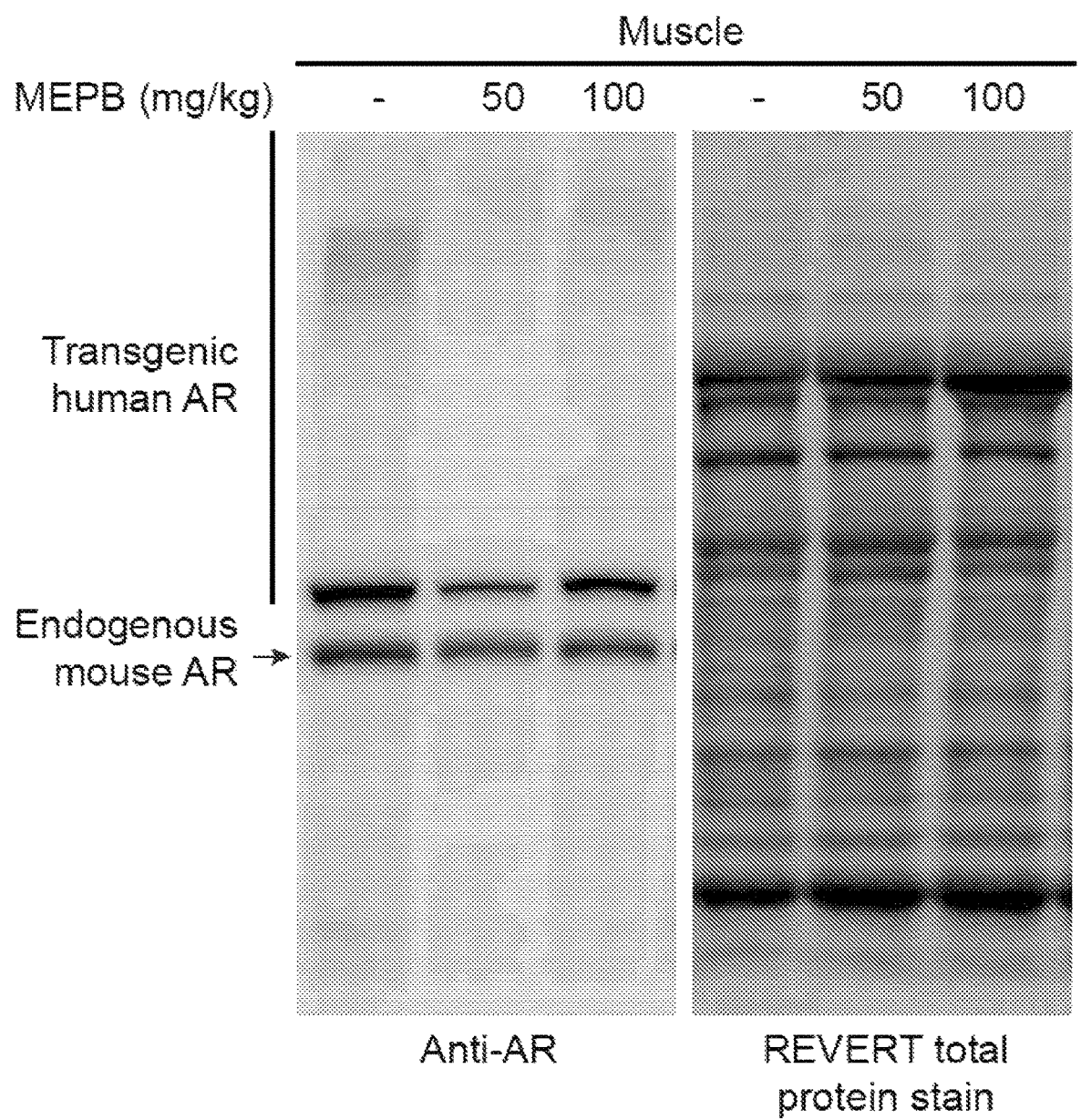
FIGS. 13A-13D demonstrate the effect of AF2 modulators on AR protein levels in AR121Q mice.
Figure 13B:
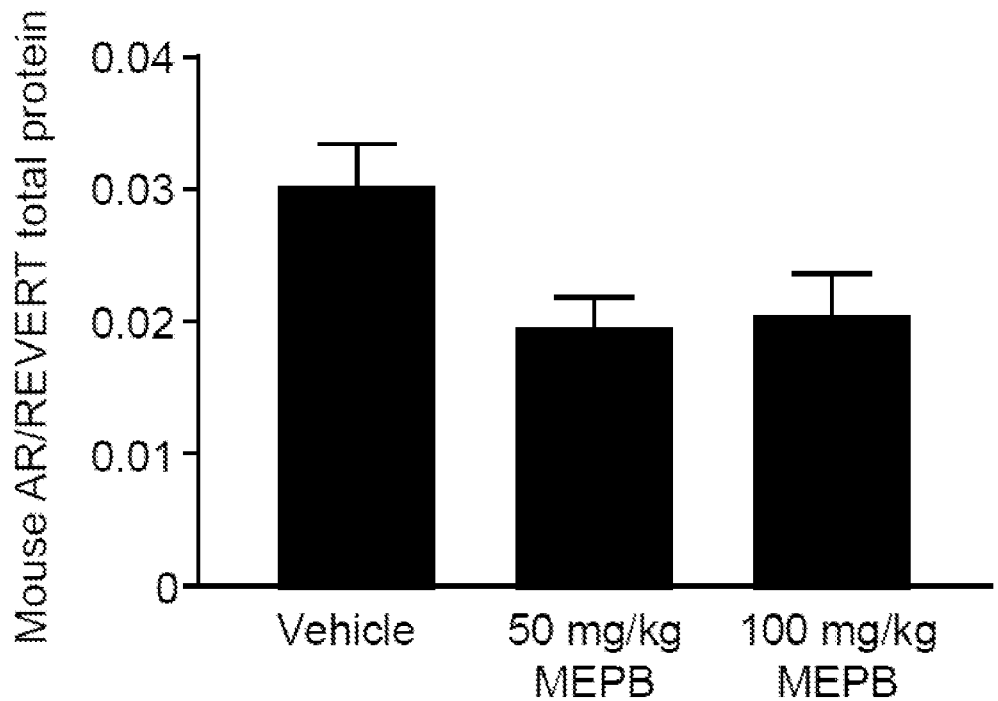
Figure 13B:
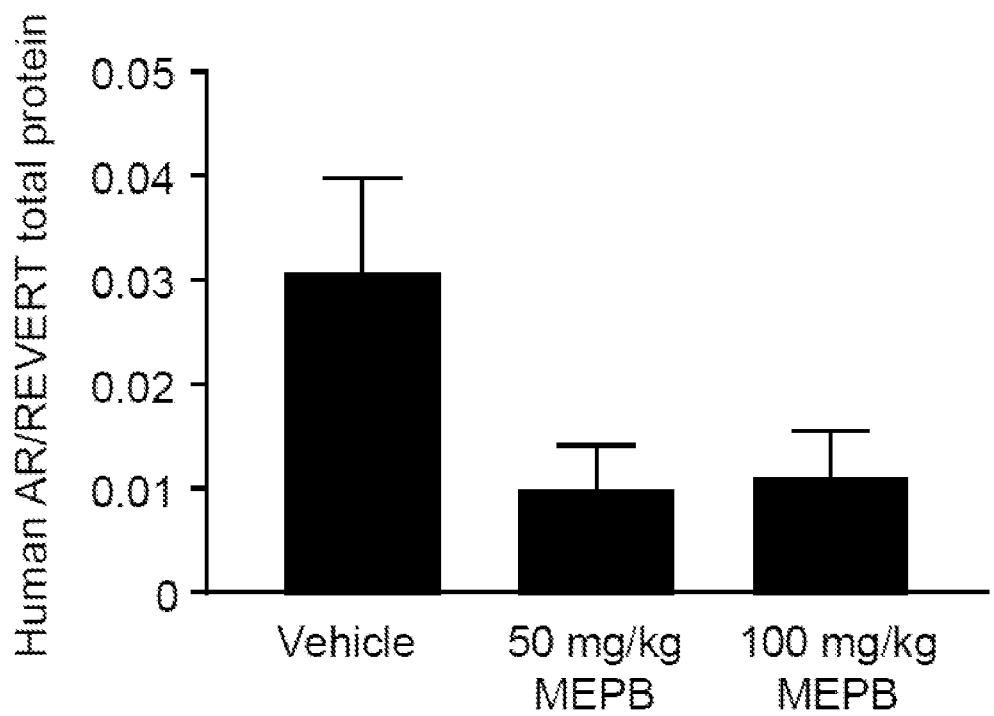
Figure 13C:
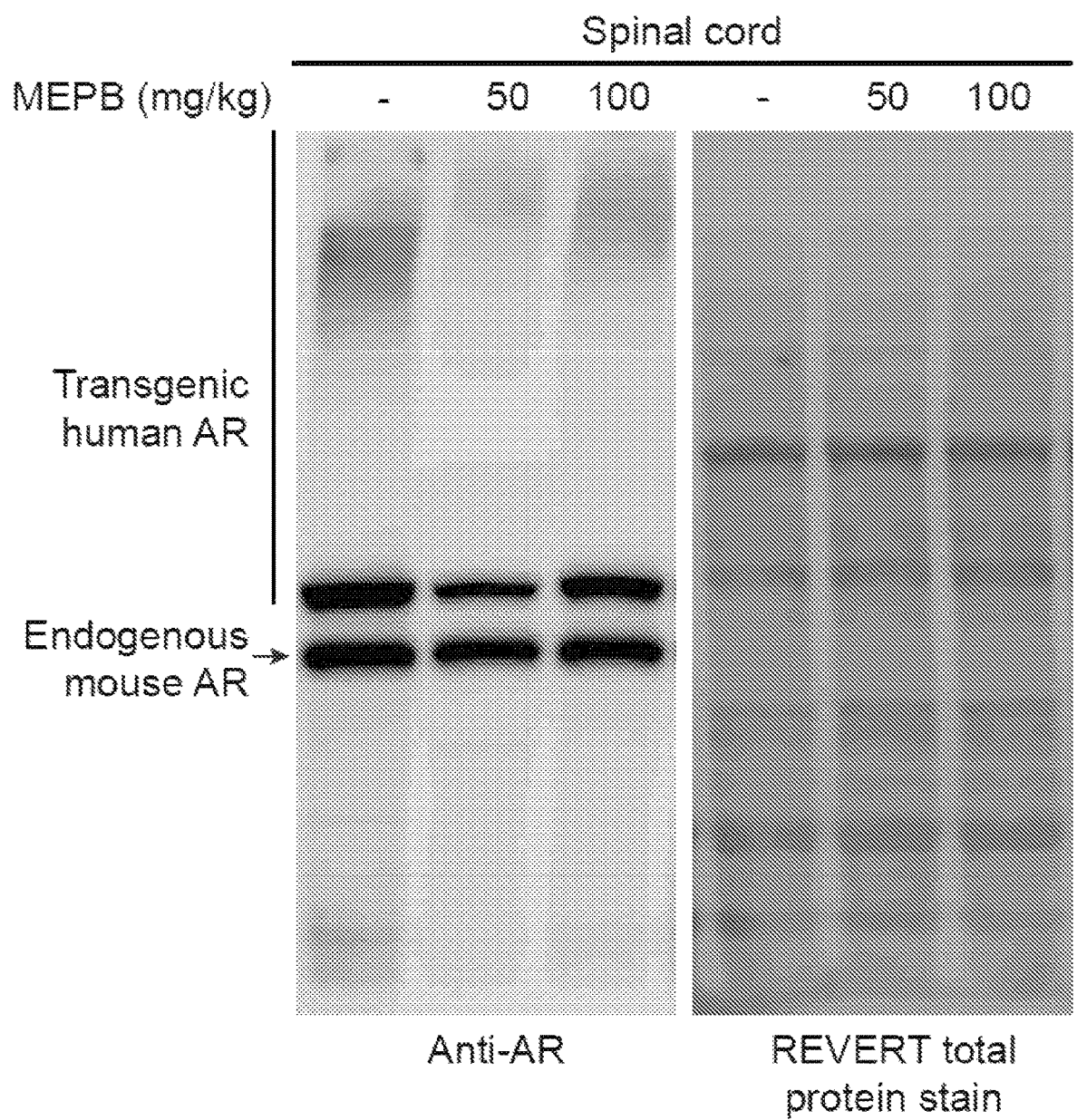
Figure 13D:
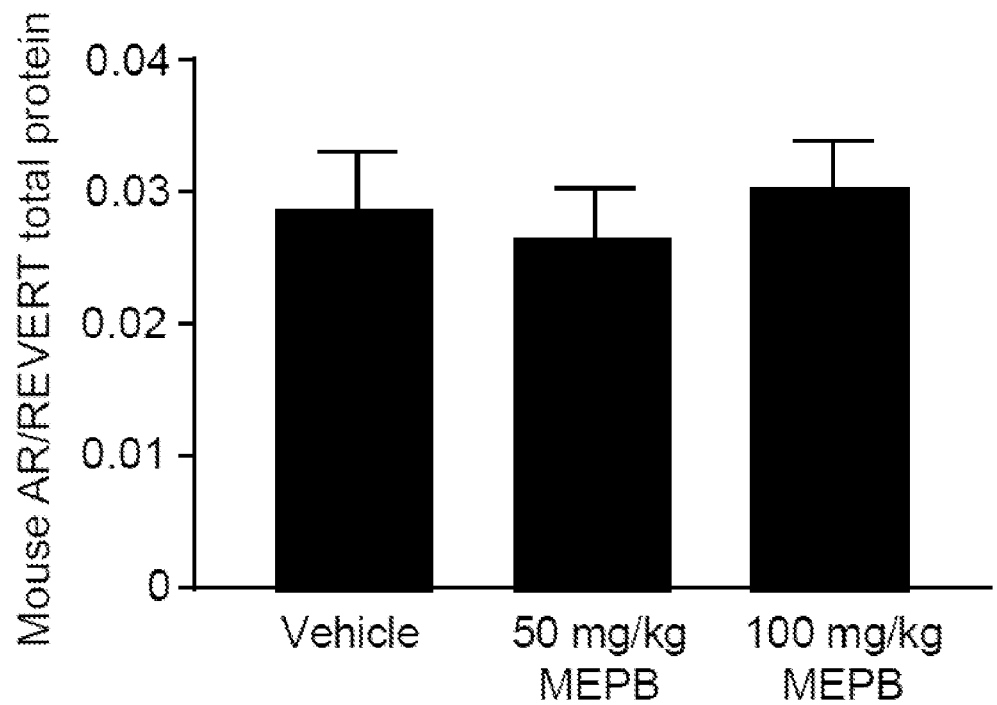
Figure 13D:
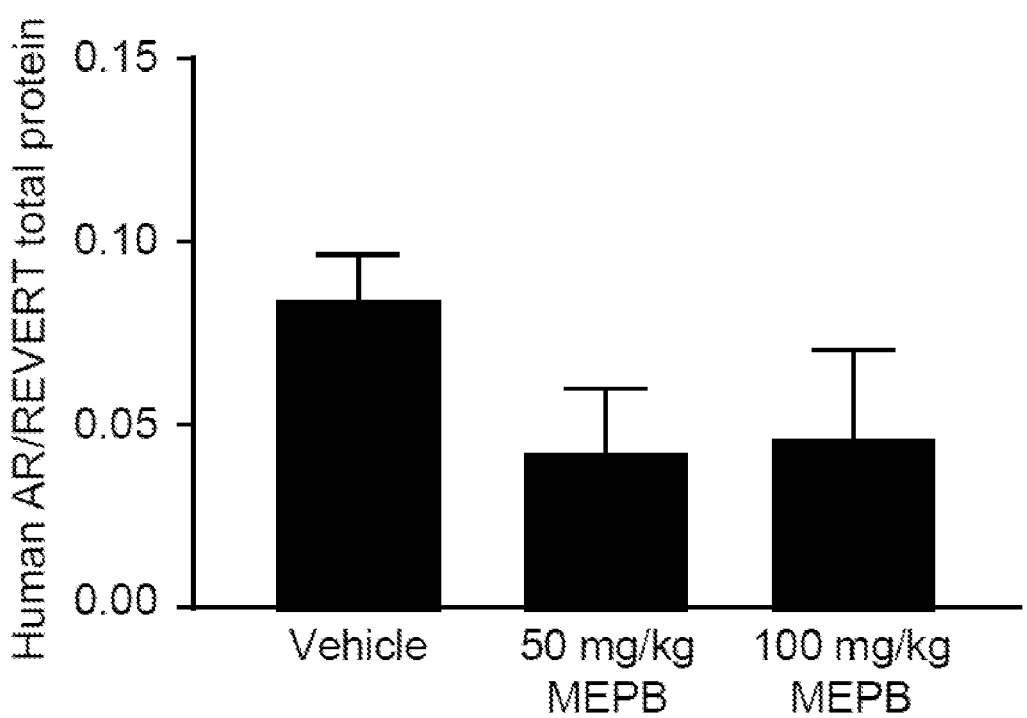

AF2 Modulators Do Not Affect Normal AR
Signaling Function, but Promote Corepressor
Binding To assess the mechanism by which AF2 modulation attenuates SBMA-associated phenotypes, we performed analyses of polyQ-expanded AR activity in response to TA and MEPB (FIGS. 6A-6E and FIGS. 12A-12F). Neither TA nor MEPB treatment reduced steady state levels of polyQ-expanded AR protein in stably transfected motor neuron (MN1) cells or transiently transfected HEK293T cells (FIGS. 12A-12E), indicating that reduced SBMA-associated toxicity as a result of TA and MEPB treatment is not simply due to enhanced degradation of the AR. In addition, the presence of high-molecular weight, multimeric AR complexes and aggregates were unchanged in response to TA and MEPB treatment in HEK293T cells (FIG. 12E and FIG. 12F). Consistent with these observations, MEPB treatment did not statistically significantly change the expression level of endogenous mouse AR or transgenic human AR in the muscle and spinal cords of AR121Q mice (FIGS. 13A-13D). Similarly, neither MEPB nor TA treatment significantly changed the expression of transgenic AR in Drosophila (FIG. 8D and FIG. 8E), suggesting that TA- and MEPB-mediated attenuation of toxicity occurs independently of AR aggregation. Moreover, neither MEPB nor TA treatment significantly altered DHT-dependent nuclear translocation of polyQ-expanded AR in HEK293T cells and Drosophila (FIGS. 6A-6B). A dual luciferase reporter assay demonstrated that the transactivational capacity of polyQ-expanded AR was not significantly altered by TA or MEPB treatment, although a trend of reduced transcriptional activity was present in cells treated with high concentrations (100 µM) of either TA or MEPB (FIG. 6C). Finally, we selected eight AR-responsive genes expressed in motor neurons (Igfbp5, Mt2, Sgk1, Trib1, Camkk2, Tsc22d3, PIk3r3, and AR) and assessed the impact of MEPB on response to ligand-dependent changes in transcription in MN1 cells that stably express human AR (MN1-AR24Q cells). We confirmed ligand-dependent changes in transcription for seven of the eight target genes but found no impact of MEPB (FIG. 6D). These results indicate that although the AR signaling pathway remains intact, AF2 modulation by SARMs selectively alters AR activity, reducing the toxicity associated with polyQ-expanded AR but leaving other aspects of AR responsiveness intact. Indeed, the reversal of testicular atrophy in the SBMA mice upon treatment with MEPB is consistent with this conclusion.

Because the AR has been well characterized to repress as well as activate transcription of its target genes and these repressor/activator activities are dependent on binding of a specific complement of coactivators and corepressors to the AF2 domain[10], we hypothesized that SARM treatment may specifically promote recruitment of corepressors to the AF2 domain rather than block coactivator binding. This would potentially lead to repression of selected target genes driving SBMA-associated toxicity, while allowing transcriptional activation of other target genes. To determine whether association between the AR LBD and steroid receptor corepressors is augmented in response to AF2 modulation by TA or MEPB, we performed a mammalian two-hybrid assay, whereby increased association between the AR LBD and a given coregulator drives luciferase reporter activity. Consistent with our hypothesis, binding between the AR LBD and nuclear receptor corepressor-1 (NCoR) was specifically increased by TA and MEPB treatment, whereas binding of silencing mediator for retinoic acid and thyroid hormone receptors (SMRT) was unchanged (FIG. 6E), suggesting that modulation of the AF2 domain by TA and MEPB occurs by a selective and precisely controlled mechanism.

Discussion

Recent advances in prostate cancer research have led to the discovery of many SARM compounds that specifically bind to and modulate coregulator binding to the AR AF2 domain[17-22]. Interestingly, a reciprocal relationship between prostate cancer and SBMA has been suggested to be mediated by polyQ length, as prostate cancer risk appears to be elevated in individuals whose AR gene contains fewer than ten CAG repeats[28]. Increased transactivational activity of the AR is also inversely correlated with CAG repeat length[29,30], and polyQ expansion has been suggested to augment intrinsic disorder within the N-terminal domain, reducing coactivator binding to the AR LBD through an unknown mechanism[31,32]. To avoid the proliferative effects of increased AR transactivation, compounds that reduce coactivator binding or recruit corepressor binding to the AF2 domain have been sought for prostate cancer therapy. The seminal discovery of the BF3 regulatory pocket as an allosteric regulator of the AF2 domain by Estebanez-Perpina et al. (2007) was an unexpected revelation in the search for such drugs[19]. The development of several compounds that specifically target the BF3 pocket have since been reported[20-22].

A recent report by Jehle et al. (2014) demonstrated the importance of the BF3 domain in prostate cancer and the role that BF3 modulation may play in therapeutic treatment[33]. Specifically, ectopic expression of the co-chaperone Bag-1L in the prostate secretory epithelium may be associated with tumorigenesis by stimulating AR activation via interaction between a duplicated GARRPR hexapeptide motif within Bag-1L and the AR BF3 binding pocket. Interestingly, the binding of LXXLL-bearing coactivators to the AF2 domain was inhibited by Bag-1L binding to the BF3 pocket, further demonstrating the allosteric regulation that BF3 imparts upon the AF2 domain. Moreover, BF3-Bag-1L binding was inhibited by the MEPB analog 2-((2-(2,6-dimethylphenoxy)ethyl)thio)-1H-benzimidazole (compound 49 or CPD49)[20,33], suggesting that modulation of the interaction between the AR and Bag-1L by CPD49 may provide a promising approach to mitigate the oncogenic program initiated by androgen signaling in prostate cancer.

We previously showed that coactivator binding to the AF2 domain is required for polyQ-expanded AR toxicity in *Drosophila*[8]. Despite the apparent reciprocal relationship between prostate cancer and SBMA, we reasoned that targeting the BH3 interaction surface to modulate coregulator binding to the AF2 domain may represent a common strategy for treatment of both SBMA and prostate cancer. Therefore, we initiated a *Drosophila*-based screen to determine whether any previously described BF3-binding compounds may be advantageous for the treatment of SBMA. As expected, several compounds either had no effect on, or even exacerbated, SBMA toxicity (data not shown), suggesting that some compounds may be more effective in the treatment of prostate cancer whereas others may be more effective for SBMA. Nevertheless, two promising compounds (TA and MEPB) emerged that ameliorated polyQ-expanded AR toxicity in flies and became candidate therapeutics for a preclinical trial in a mammalian model of SBMA.

TA is a well-known and well-studied compound belonging to the nonsteroidal anti-inflammatory drug family of small molecules[34-37]. Although it has been approved for treatment of migraines in the United Kingdom by the National Health Service and is available as a general analgesic for humans and animals in several countries in Europe, Latin America, and Asia, it has not been approved for any use in the United States. This compound was found to have poor bioavailability in mouse brain, spinal cord, and muscle and no significant effect in a pilot trial in AR121Q mice, and was subsequently not pursued in this study.

MEPB was first described by Lack et al. (2011) through virtual screening for BF3-binding compounds[21]. X-ray crystallography revealed MEPB to specifically bind the BF3 pocket of the AR, where the benzimidazole moiety of MEPB is oriented toward the interior of the BF3 pocket and is stabilized by strong hydrophobic interactions with Pro723, Phe673, and Tyr834 and an arene-arene conjugation between a benzene ring of MEPB and Phe826. MEPB was shown unequivocally to bind to the BF3 domain and as a consequence modulate AF2 binding to coregulators. MEPB was found to have good bioavailability in mouse brain, spinal cord and muscle and, after showing a beneficial effect in a pilot trial in SBMA mice, was selected for further evaluation. In a blinded, multi-dose preclinical trial in male SBMA mice, MEPB treatment was found to significantly augment body weight, reduce hindlimb clasping, and improve rotarod activity, grip strength, gait, and QOL score. Consistent with improvement in the behavioral phenotype, MEPB treatment rescued motor neuron loss and neurogenic atrophy. Finally, MEPB treatment was found to reverse testicular atrophy in the SBMA mice, a finding that underscores the selective activity of MEPB. Prior in vitro analyses found that MEPB binding to BF3 enhances AF2 interaction with coregulators bearing an extended LXXLL motif (termed the "corepressor nuclear receptor box"), such as that found in the corepressor NCoR[38,39]. This observation is consistent with our observation that NCoR was recruited to the AR LBD by MEPB, and suggests that MEPB may relieve polyQ-expanded AR-mediated toxicity by promoting the binding of corepressors to the AF2 domain.

Altogether, these results provide considerable evidence for the utility of AR AF2 domain modulation by BF3-binding compounds as a paradigm for SBMA therapy. Subtle modulation of coregulator binding, and thus AR functional activity, rather than ablation of the entire androgen signaling pathway, may provide therapeutic relief of neurodegenerative symptoms in patients with SBMA. Such a targeted approach may reduce or potentially even reverse adverse effects of androgen insensitivity and improve the QOL of patients with SBMA.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

REFERENCES

1. Kennedy, W. R., Alter, M. & Sung, J. H. Progressive proximal spinal and bulbar muscular atrophy of late onset. A sex-linked recessive trait. *Neurology* 18, 671-680 (1968).

2. Chahin, N., Klein, C., Mandrekar, J. & Sorenson, E. Natural history of spinal-bulbar muscular atrophy. *Neurology* 70, 1967-1971 (2008).
3. Poletti, A., Negri-Cesi, P. & Martini, L. Reflections on the diseases linked to mutations of the androgen receptor. *Endocrine* 28, 243-262 (2005).
4. Fratta, P., et al. Correlation of clinical and molecular features in spinal bulbar muscular atrophy. *Neurology* 82, 2077-2084 (2014).
5. La Spada, A. R., Wilson, E. M., Lubahn, D. B., Harding, A. E. & Fischbeck, K. H. Androgen receptor gene mutations in X-linked spinal and bulbar muscular atrophy. *Nature* 352, 77-79 (1991).
6. Soraru, G., et al. Spinal and bulbar muscular atrophy: skeletal muscle pathology in male patients and heterozygous females. *J Neurol Sci* 264, 100-105 (2008).
7. Finsterer, J. Perspectives of Kennedy's disease. *J Neurol Sci* 298, 1-10 (2010).
8. Nedelsky, N. B., et al. Native functions of the androgen receptor are essential to pathogenesis in a *Drosophila* model of spinobulbar muscular atrophy. *Neuron* 67, 936-952 (2010).
9. Smith, C. L. & O'Malley, B. W. Coregulator function: a key to understanding tissue specificity of selective receptor modulators. *Endocr Rev* 25, 45-71 (2004).
10. Askew, E. B., Gampe, R. T., Jr., Stanley, T. B., Faggart, J. L. & Wilson, E. M. Modulation of androgen receptor activation function 2 by testosterone and dihydrotestosterone. *J Biol Chem* 282, 25801-25816 (2007).
11. Chevalier-Larsen, E. S., et al. Castration restores function and neurofilament alterations of aged symptomatic males in a transgenic mouse model of spinal and bulbar muscular atrophy. *J Neurosci* 24, 4778-4786 (2004).
12. Katsuno, M., et al. Testosterone reduction prevents phenotypic expression in a transgenic mouse model of spinal and bulbar muscular atrophy. *Neuron* 35, 843-854 (2002).
13. Katsuno, M., et al. Leuprorelin rescues polyglutamine-dependent phenotypes in a transgenic mouse model of spinal and bulbar muscular atrophy. *Nat Med* 9, 768-773 (2003).
14. Katsuno, M., et al. Efficacy and safety of leuprorelin in patients with spinal and bulbar muscular atrophy (JASMITT study): a multicentre, randomised, double-blind, placebo-controlled trial. *Lancet Neurol* 9, 875-884 (2010).
15. Yang, Z., et al. ASC-J9 ameliorates spinal and bulbar muscular atrophy phenotype via degradation of androgen receptor. *Nat Med* 13, 348-353 (2007).
16. Banno, H., et al. Phase 2 trial of leuprorelin in patients with spinal and bulbar muscular atrophy. *Ann Neurol* 65, 140-150 (2009).
17. Axerio-Cilies, P., et al. Inhibitors of androgen receptor activation function-2 (AF2) site identified through virtual screening. *J Med Chem* 54, 6197-6205 (2011).
18. Ban, F., et al. Discovery of 1H-indole-2-carboxamides as novel inhibitors of the androgen receptor binding function 3 (BF3). *J Med Chem* 57, 6867-6872 (2014).
19. Estebanez-Perpina, E., et al. A surface on the androgen receptor that allosterically regulates coactivator binding. *Proc Natl Acad Sci USA* 104, 16074-16079 (2007).
20. Munuganti, R. S., et al. Targeting the binding function 3 (BF3) site of the androgen receptor through virtual screening. 2. development of 2-((2-phenoxyethyl) thio)-1H-benzimidazole derivatives. *J Med Chem* 56, 1136-1148 (2013).
21. Lack, N. A., et al. Targeting the binding function 3 (BF3) site of the human androgen receptor through virtual screening. *J Med Chem* 54, 8563-8573 (2011).
22. Munuganti, R. S., et al. Identification of a potent antiandrogen that targets the BF3 site of the androgen receptor and inhibits enzalutamide-resistant prostate cancer. *Chem Biol* 21, 1476-1485 (2014).
23. Rocchi, A., et al. Glycolytic-to-oxidative fiber-type switch and mTOR signaling activation are early-onset features of SBMA muscle modified by high-fat diet. *Acta Neuropathol* 132, 127-144 (2016).
24. Cashman, N. R., Covault, J., Wollman, R. L. & Sanes, J. R. Neural cell adhesion molecule in normal, denervated, and myopathic human muscle. *Ann Neurol* 21, 481-489 (1987).
25. Gosztonyi, G., Naschold, U., Grozdanovic, Z., Stoltenburg-Didinger, G. & Gossrau, R. Expression of Leu-19 (CD56, N-CAM) and nitric oxide synthase (NOS) I in denervated and reinnervated human skeletal muscle. *Microsc Res Tech* 55, 187-197 (2001).
26. Marbini, A., et al. Immunohistochemical study of muscle biopsy in children with cerebral palsy. *Brain Dev* 24, 63-66 (2002).
27. Yu, Z., et al. Abnormalities of germ cell maturation and sertoli cell cytoskeleton in androgen receptor 113 CAG knock-in mice reveal toxic effects of the mutant protein. *Am J Pathol* 168, 195-204 (2006).
28. Sun, J. H. & Lee, S. A. Association between CAG repeat polymorphisms and the risk of prostate cancer: a meta-analysis by race, study design and the number of (CAG)n repeat polymorphisms. *Int J Mol Med* 32, 1195-1203 (2013).
29. Albertelli, M. A., et al. Glutamine tract length of human androgen receptors affects hormone-dependent and -independent prostate cancer in mice. *Hum Mol Genet* 17, 98-110 (2008).
30. Robins, D. M., Albertelli, M. A. & O'Mahony, O. A. Androgen receptor variants and prostate cancer in humanized AR mice. *J Steroid Biochem Mol Biol* 108, 230-236 (2008).
31. Buchanan, G., et al. Structural and functional consequences of glutamine tract variation in the androgen receptor. *Hum Mol Genet* 13, 1677-1692 (2004).
32. Buchanan, G., et al. Corepressor effect on androgen receptor activity varies with the length of the CAG encoded polyglutamine repeat and is dependent on receptor/corepressor ratio in prostate cancer cells. *Mol Cell Endocrinol* 342, 20-31 (2011).
33. Jehle, K., et al. Coregulator control of androgen receptor action by a novel nuclear receptor-binding motif. *J Biol Chem* 289, 8839-8851 (2014).
34. Corell, T. Pharmacology of tolfenamic acid. *Pharmacol Toxicol* 75 Suppl 2, 14-21 (1994).
35. Hendel, J. The overall safety of tolfenamic acid. *Pharmacol Toxicol* 75 Suppl 2, 53-55 (1994).
36. Hendel, L., Larsen, E. & Bonnevie, O. A comparative study of the influence of tolfenamic acid (Clotam) and diclofenac sodium (Voltaren) on the gastrointestinal mucosa in patients with a history of NSAID-related dyspeptic symptoms. *Pharmacol Toxicol* 75 Suppl 2, 49-50 (1994).
37. Pedersen, S. B. Biopharmaceutical aspects of tolfenamic acid. *Pharmacol Toxicol* 75 Suppl 2, 22-32 (1994).
38. Yuan, H., et al. Suppression of the androgen receptor function by quercetin through protein-protein interactions of Sp1, c-Jun, and the androgen receptor in human prostate cancer cells. *Mol Cell Biochem* 339, 253-262 (2010).
39. Hodgson, M. C., Shen, H. C., Hollenberg, A. N. & Balk, S. P. Structural basis for nuclear receptor corepressor recruitment by antagonist-liganded androgen receptor. *Mol Cancer Ther* 7, 3187-3194 (2008).

40. Bott, L. C., et al. A small-molecule Nrf1 and Nrf2 activator mitigates polyglutamine toxicity in spinal and bulbar muscular atrophy. *Hum Mol Genet* 25, 1979-1989 (2016).

41. Glynn, M. W. & Glover, T. W. Incomplete processing of mutant lamin A in Hutchinson-Gilford progeria leads to nuclear abnormalities, which are reversed by farnesyltransferase inhibition. *Hum Mol Genet* 14, 2959-2969 (2005).

42. Schindelin, J., et al. Fiji: an open-source platform for biological-image analysis. *Nat Methods* 9, 676-682 (2012).

43. Perrier, D. & Gibaldi, M. General derivation of the equation for time to reach a certain fraction of steady state. *J Pharm Sci* 71, 474-475 (1982).

44. Brooks, B. P., et al. Characterization of an expanded glutamine repeat androgen receptor in a neuronal cell culture system. *Neurobiol Dis* 3, 313-323 (1997).

The present disclosure will be better understood upon review of the following features, which should not be confused with the claims.

Feature 1. A pharmaceutical formulation for treating spinobulbar muscular atrophy in a subject in need thereof, the pharmaceutical formulation comprising: a therapeutically effective amount of a small molecule, a derivative thereof, a prodrug thereof, or a salt thereof; wherein the small molecule has a structure according to the following formula

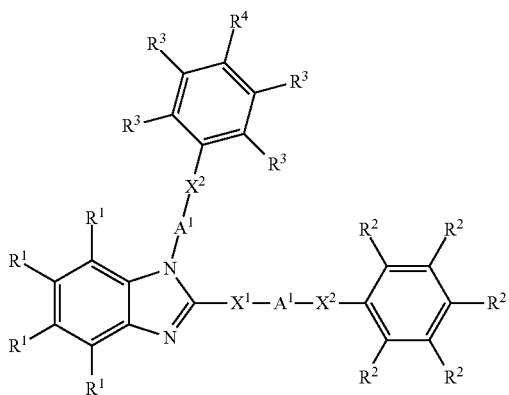

wherein each occurrence of $R^1$, $R^2$, $R^3$, and $R^4$ is independently a hydrogen, a hydroxyl, a halogen, or a substituted or unsubstituted $C_1$-$C_6$ alkyl or alkoxy; wherein each occurrence of $X^1$ and $X^2$ is independently O or S; wherein each occurrence of $A^1$ is independently none or a substituted or unsubstituted $C_1$-$C_6$ alkyl diradical; and wherein the therapeutically effective amount is effective to ameliorate one or more symptoms of spinobulbar muscular atrophy in the subject.

Feature 2. The pharmaceutical formulation according to any one of Features 1-23, wherein each occurrence of $R^1$ is a hydrogen.

Features 3. The pharmaceutical formulation according to any one of Features 1-23, wherein each occurrence of $R^2$ is a hydrogen.

Features 4. The pharmaceutical formulation according to any one of Features 1-23, wherein each occurrence of $R^3$ is a hydrogen.

Features 5. The pharmaceutical formulation according to any one of Features 1-23, wherein $R^4$ is a hydrogen, methyl, ethyl, isopropyl, or t-butyl.

Features 6. The pharmaceutical formulation according to any one of Features 1-23, wherein $X^1$ is S.

Features 7. The pharmaceutical formulation according to any one of Features 1-23, wherein each occurrence of $X^2$ is O.

Features 8. The pharmaceutical formulation according to any one of Features 1-23, wherein each occurrence of Al is an unsubstituted $C_1$-$C_3$ alkyl diradical.

Features 9. The pharmaceutical formulation according to any one of Features 1-23, wherein the small molecule is 1-[2-(4-methylphenoxy)ethyl]-2-[(2-phenoxyethyl)sulfanyl]-1H-benzimidazole having a structure according to the following formula

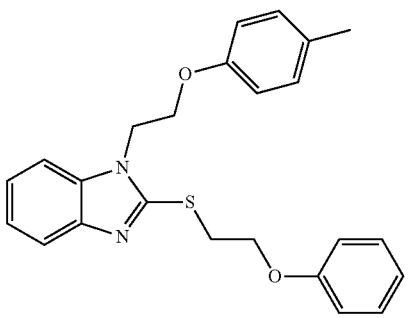

Features 10. The pharmaceutical formulation according to any one of Features 1-23, wherein the pharmaceutical formulation comprises the derivative of the small molecule; and wherein the derivative is selected from the group consisting of ester and amide derivatives of the small molecule, pegylated derivatives of the small molecule, and N-oxides of the small molecule.

Features 11. The pharmaceutical formulation according to any one of Features 1-23, wherein the pharmaceutical formulation comprises the prodrug of the small molecule; and wherein the prodrug is an amide, carbamate, imide, ester, anhydride, thioester, or thioanhydride of the small molecule.

Features 12. The pharmaceutical formulation according to any one of Features 1-23, wherein the pharmaceutical formulation comprises the derivative of the small molecule, and wherein the derivative comprises a substituent selected from the group consisting of a halogen, an azide, an alkyl, an aralkyl, an alkenyl, an alkynyl, a cycloalkyl, a hydroxyl, an alkoxyl, an amino, a nitro, a sulfhydryl, an imino, an amido, a phosphonate, a phosphinate, a carbonyl, a carboxyl, a silyl, an ether, an alkylthio, a sulfonyl, a sulfonamido, a ketone, an aldehyde, a thioketone, an ester, a heterocyclyl, a —CN, an aryl, an aryloxy, a perhaloalkoxy, an aralkoxy, a heteroaryl, a heteroaryloxy, a heteroarylalkyl, a heteroaralkoxy, an azido, an alkylthio, an oxo, an acylalkyl, a carboxy esters, a carboxamido, an acyloxy, an aminoalkyl, an alkylaminoaryl, an alkylaryl, an alkylaminoalkyl, an alkoxyaryl, an arylamino, an aralkylamino, an alkylsulfonyl, a carboxamidoalkylaryl, a carboxamidoaryl, a hydroxyalkyl, a haloalkyl, an alkylaminoalkylcarboxy, an aminocarboxamidoalkyl, a cyano, an alkoxyalkyl, a perhaloalkyl, and an arylalkyloxyalkyl.

Features 13. The pharmaceutical formulation according to any one of Features 1-23, wherein the pharmaceutical formulation comprises the salt of the small molecule, and either (i) the salt is a pharmaceutically acceptable acid addition salt comprising an anion selected from the group consisting of a sulfate, a citrate, matate, an acetate, an oxalate, a chloride, a bromide, an iodide, a nitrate, a sulfate, a bisulfate, a phosphate, an acid phosphate, an isonicotinate, an acetate, a lactate, a salicylate, a tartrate, an oleate, a tannate, a pantothenate, a bitartrate, an ascorbate, a succinate, a maleate, a gentisinate, a fumarate, a gluconate, a glucaronate, a saccharate, a formate, a benzoate, a glutamate, a methanesulfonate, an ethanesulfonate, a benzenesulfonate, a p-toluenesulfonate and a pamoate (i.e., 1,1'-methylene-bis-(2-hydroxy-3-naphthoate)); or (ii) the salt is a pharmaceutically acceptable base addition salt comprising a cation selected from the group consisting alkali metals and alkaline earth metals, such as calcium, magnesium, sodium, lithium, zinc, potassium, and iron.

Features 14. A pharmaceutical formulation for treating spinobulbar muscular atrophy in a subject in need thereof, the pharmaceutical formulation comprising a therapeutically effective amount of a selective androgen receptor modulator, wherein the therapeutically effective amount is effective to ameliorate one or more symptoms of spinobulbar muscular atrophy in the subject.

Features 15. The pharmaceutical formulation according to any one of Features 1-23, wherein the selective androgen receptor modulator alters a co-regulator binding to the activation function-2 (AF2) domain of the androgen receptor.

Features 16. The pharmaceutical formulation according to any one of Features 1-23, wherein the selective androgen receptor selectively binds to the binding function-3 (BF3) domain of the androgen receptor.

Features 17. The pharmaceutical formulation according to any one of Features 1-23, wherein the selective androgen receptor modulator is selected from the group consisting of 17α-methyl-17β-hydroxy-2-oxa-5α-androstan-3-one and derivatives thereof, testosterone and derivatives thereof, 4,5α-dihydrotestosterone and derivatives thereof, ((2S)-3-(4-cyanophenoxy)-N-[4-cyano-3-(trifluoromethyl)phenyl]-2-hydroxy-2-methylpropanamide) and a derivative thereof, and a combination thereof.

Features 18. The pharmaceutical formulation according to any one of Features 1-23, wherein the formulation is a parenteral formulation selected from a solution, a suspension, an emulsion, and a solid form suitable to prepare an injectable solution or suspension upon the addition of a reconstitution medium.

Features 19. The pharmaceutical formulation according to any one of Features 1-23, wherein the formulation is an enteral formulation selected from a tablet, a capsule, a solution, a suspension, a syrup, and a lozenge.

Features 20. The pharmaceutical formulation according to any one of Features 1-23, wherein the effective amount is effective to prevent or delay loss of body weight, a loss of mobility, and/or a loss of physical strength in the subject.

Features 21. The pharmaceutical formulation according to any one of Features 1-23, wherein the effective amount is effective to prevent or delay neurogenic atrophy and/or to prevent a loss of spinal cord motor neurons in the subject.

Features 22. The pharmaceutical formulation according to any one of Features 1-23, wherein the effective amount is effective to restore the frequency of type I myofibers to normal levels for a healthy subject.

Features 23. The pharmaceutical formulation according to any one of Features 1-22, wherein the effective amount is effective to reverse testicular atrophy in the subject.

Feature 24. A method of treating spinobulbar muscular atrophy in a subject in need thereof, the method comprising administering a therapeutically effective amount of a small molecule, a derivative thereof, a prodrug thereof, or a salt thereof to the subject, wherein the small molecule has a structure according to the following formula

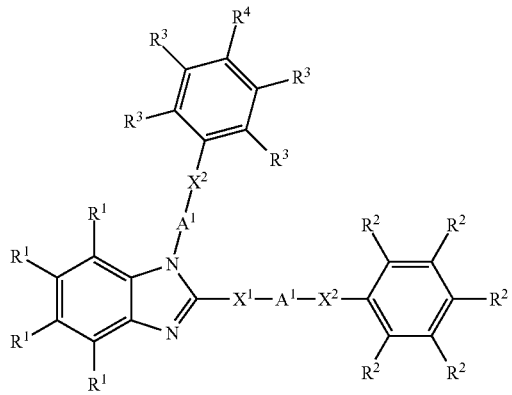

wherein each occurrence of $R^1$, $R^2$, $R^3$, and $R^4$ is independently a hydrogen, a hydroxyl, a halogen, or a substituted or unsubstituted $C_1$-$C_6$ alkyl or alkoxy; wherein each occurrence of $X^1$ and $X^2$ is independently O or S; wherein each occurrence of $A^1$ is independently none or a substituted or unsubstituted $C_1$-$C_6$ alkyl diradical; and wherein the therapeutically effective amount is effective to ameliorate one or more symptoms of spinobulbar muscular atrophy in the subject.

Feature 25. A method of treating spinobulbar muscular atrophy in a subject in need thereof, the method comprising administering a therapeutically effective amount of a selective androgen receptor modulator to the subject, wherein the therapeutically effective amount is effective to ameliorate one or more symptoms of spinobulbar muscular atrophy in the subject.

Feature 26. The method according to any one of Features 24-35, wherein the selective androgen receptor modulator alters a co-regulator binding to the activation function-2 (AF2) domain of the androgen receptor.

Feature 27. The method according to any one of Features 24-35, wherein the selective androgen receptor selectively binds to the binding function-3 (BF3) domain of the androgen receptor.

Feature 28. The method according to any one of Features 24-35, wherein the selective androgen receptor modulator is selected from the group consisting of 17α-methyl-17β-hydroxy-2-oxa-5α-androstan-3-one and derivatives thereof, testosterone and derivatives thereof, 4,5α-dihydrotestosterone and derivatives thereof, ((2S)-3-(4-cyanophenoxy)-N-[4-cyano-3-(trifluoromethyl)phenyl]-2-hydroxy-2-methylpropanamide) and a derivative thereof, and a combination thereof.

Feature 29. The method according to any one of Features 24-35, wherein the method comprises administering a pharmaceutical formulation according to any one of claims 1-23.

Feature 30. The method according to any one of Features 24-35, wherein the effective amount is effective to prevent or delay loss of body weight, a loss of mobility, and/or a loss of physical strength in the subject.

Feature 31. The method according to any one of Features 24-35, wherein the effective amount is effective to prevent or delay neurogenic atrophy and/or to prevent a loss of spinal cord motor neurons in the subject.

Feature 32 The method according to any one of Features 24-35, wherein the effective amount is effective to restore the frequency of type I myofibers to normal levels for a healthy subject.

Feature 33. The method according to any one of Features 24-35, wherein the effective amount is effective to reverse testicular atrophy in the subject.

Feature 34. The method according to any one of Features 24-35, wherein the subject is a human.

Feature 35. The method according to any one of Features 24-34, wherein the method comprises intravenous injection, intradermal injection, intramuscular injection, subcutaneous injection, infusion, or a combination thereof.

I claim:

1. A method of treating spinobulbar muscular atrophy in a subject in need thereof, the method comprising administering to the subject a therapeutically effective amount of a small molecule
having a structure according to the following formula:

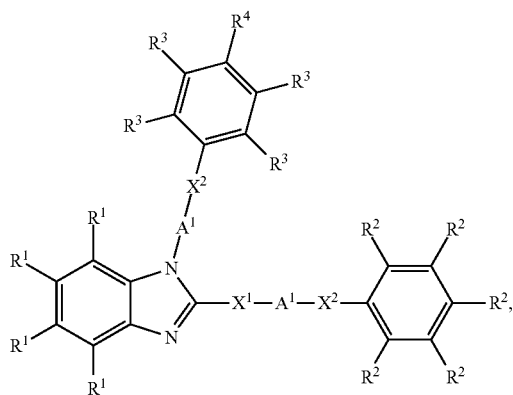

or a derivative thereof, a prodrug thereof, or a salt thereof;
wherein each occurrence of $R^1$, $R^2$, $R^3$, and $R^4$ is independently a hydrogen, a hydroxyl, a halogen, or a substituted or unsubstituted $C_1$-$C_6$ alkyl or alkoxy;
wherein each occurrence of $X^1$ and $X^2$ is independently O or S;
wherein each occurrence of Al is independently none or a substituted or unsubstituted $C_1$-$C_6$ alkyl diradical;
wherein the derivative of the small molecule is selected from the group consisting of ester and amide derivatives of the small molecule, pegylated derivatives of the small molecule, and N-oxides of the small molecule;
wherein the subject has been diagnosed with a need for selective modulation of androgen receptor function;
wherein the selective modulation of androgen receptor function comprises decreasing toxicity associated with polyQ-expanded androgen receptor while leaving androgen receptor signaling activity essentially intact; and
wherein the therapeutically effective amount is effective to ameliorate one or more symptoms of spinobulbar muscular atrophy in the subject.

2. The method according to claim 1, wherein the small molecule is 1-[2-(4-methylphenoxy)ethyl]-2-[(2-phenoxyethyl)sulfanyl]-1H-benzimidazole having a structure according to the following formula

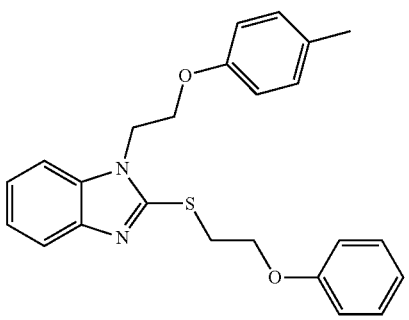

3. The method according to claim 1, wherein the effective amount is effective to prevent or delay loss of body weight, a loss of mobility, and/or a loss of physical strength in the subject.

4. The method according to claim 1, wherein the effective amount is effective to prevent or delay neurogenic atrophy and/or to prevent a loss of spinal cord motor neurons in the subject.

5. The method according to claim 1, wherein the effective amount is effective to restore the frequency of type I myofibers to normal levels for a healthy subject.

6. The method according to claim 1, wherein the effective amount is effective to reverse testicular atrophy in the subject.

7. The method of claim 1, wherein the administering a therapeutically effective amount of the small molecule, or a derivative, prodrug or salt thereof, comprises administering a pharmaceutical formulation comprising the small molecule, or a derivative, prodrug or salt thereof, and a pharmaceutically acceptable excipient.

8. The method of claim 7, wherein the pharmaceutical formulation comprises the derivative of the small molecule.

9. The method of claim 7, wherein the pharmaceutical formulation comprises the prodrug of the small molecule; and
wherein the prodrug is an amide, carbamate, imide, ester, anhydride, thioester, or thioanhydride of the small molecule.

10. The method of claim 7, wherein the pharmaceutical formulation comprises the derivative of the small molecule; and
wherein the derivative is a substituent selected from the group consisting of a halogen, an azide, an alkyl, an aralkyl, an alkenyl, an alkynyl, a cycloalkyl, a hydroxyl, an alkoxyl, an amino, a nitro, a sulfhydryl, a cyano, an aryl, an aryloxy, a perhaloalkoxy, an aralkoxy, a heteroaryl, a heteroaryloxy, a heteroarylalkyl, a heteroaralkoxy, an azido, an alkylthio, an acylalkyl, a carboxy esters, a carboxamido, an acyloxy, an aminoalkyl, an alkylaminoaryl, an alkylaryl, an alkylaminoalkyl, an alkoxyaryl, an arylamino, an aralkylamino, an alkylsulfonyl, a hydroxyalkyl, a haloalkyl, an alkylaminoalkylcarboxy, an aminocarboxamidoalkyl, an alkoxyalkyl, a perhaloalkyl, and an arylalkyloxyalkyl.

11. The method of claim 7, wherein the pharmaceutical formulation comprises the derivative of the small molecule; and either
(i) the salt is a pharmaceutically acceptable acid addition salt which is an anion an anion selected from the group consisting of a sulfate, a citrate, matate, an acetate, an oxalate, a chloride, a bromide, an iodide, a nitrate, a sulfate, a bisulfate, a phosphate, an acid phosphate, an isonicotinate, an acetate, a lactate, a salicylate, a tartrate, an oleate, a tannate, a pantothenate, a bitartrate, an ascorbate, a succinate, a maleate, a gentisinate, a fumarate, a gluconate, a glucaronate, a saccharate, a formate, a benzoate, a glutamate, a methanesulfonate, an ethanesulfonate, a benzenesulfonate, a p-toluenesulfonate and a pamoate; or (ii) the salt is a pharmaceutically acceptable base addition salt which is a cation selected from the group consisting of alkali metals and alkaline earth metals.

12. The method of claim 1, wherein each occurrence of $R^1$ is a hydrogen.

13. The method of claim 1, wherein each occurrence of $R^2$ is a hydrogen.

14. The method of claim 1, wherein each occurrence of $R^3$ is a hydrogen.

15. The method of claim 1, wherein $R^4$ is a hydrogen, methyl, ethyl, isopropyl, or t-butyl.

16. The method of claim 1, wherein Al is an unsubstituted $C_1$-$C_3$ alkyl diradical.

17. The method of claim 1, wherein the subject is a human.

18. The method of claim 1, wherein the method comprises intravenous injection, intradermal injection, intramuscular injection, subcutaneous injection, infusion, or a combination thereof.

19. The method of claim 11, wherein the cation is selected from the group consisting of calcium, magnesium, sodium, lithium, zinc, potassium, and iron.

* * * * *